US009393300B2

(12) United States Patent
Barnett et al.

(10) Patent No.: US 9,393,300 B2
(45) Date of Patent: Jul. 19, 2016

(54) IMMUNOGENIC COMPLEXES OF POLYANIONIC CARBOMERS AND ENV POLYPEPTIDES AND METHODS OF MANUFACTURE AND USE THEREOF

(71) Applicant: NOVARTIS AG, Basel (CH)

(72) Inventors: Susan W. Barnett, San Francisco, CA (US); Antu Dey, Cary, NC (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/357,270

(22) PCT Filed: Nov. 14, 2012

(86) PCT No.: PCT/US2012/065113
§ 371 (c)(1),
(2) Date: May 9, 2014

(87) PCT Pub. No.: WO2013/074696
PCT Pub. Date: May 23, 2013

(65) Prior Publication Data

US 2014/0314703 A1 Oct. 23, 2014

Related U.S. Application Data

(60) Provisional application No. 61/559,512, filed on Nov. 14, 2011.

(51) Int. Cl.

| | |
|---|---|
| ***A61K 39/385*** | (2006.01) |
| ***A61K 39/21*** | (2006.01) |
| ***A61K 39/12*** | (2006.01) |
| *A61K 39/00* | (2006.01) |

(52) U.S. Cl.
CPC ............... *A61K 39/385* (2013.01); *A61K 39/12* (2013.01); *A61K 39/21* (2013.01); *A61K 2039/53* (2013.01); *A61K 2039/545* (2013.01); *A61K 2039/55566* (2013.01); *A61K 2039/6093* (2013.01); *A61K 2039/70* (2013.01); *C12N 2740/16134* (2013.01)

(58) Field of Classification Search
CPC .................... A61K 39/21; A61K 2039/55566; A61K 2039/70; C12N 2740/16134
USPC ....................................... 424/78.18; 525/54.1
See application file for complete search history.

(56) References Cited

U.S. PATENT DOCUMENTS

| | | | |
|---|---|---|---|
| 5,840,313 A | 11/1998 | Vahlne et al. | |
| 5,846,546 A | 12/1998 | Hurwitz et al. | |
| 5,876,731 A | 3/1999 | Sia et al. | |
| 2012/0177668 A1* | 7/2012 | Jackson ............. | A61K 38/1793 424/184.1 |

OTHER PUBLICATIONS

Zifflab, Title: HBS (Hepes Buffer Saline). Downloaded from http://www.med.nyu.edu/zifflab/protocols/buffers/2xhbs.html on Sep. 11, 2015.*

Raharjo et al, title: A compltete HIV-1Env coding sequence from HIV isolated in central Java, Indonesia; ISSN 2413-0877, vol. 2, published 2015 (the 3rd ICBS-2013).*

Lewis et al., "Phase I randomised clinical trial of an HIV-1CN54, clade C, trimeric envelope vaccine candidate delivered vaginally," PLOS One, 6(9):e25165 (2011).

Cranage et al., "Repeated vaginal administration of trimeric HIV-1 clade C gp140 induces serum and mucosal antibody responses," Mucosal Immunology, 3(1):57-68 (2009).

Cranage et al., "Antibody responses after intravaginal immunisation with trimeric HIV-1 clade C gp140 in carbopol gel are augmented by systemic priming or boosting with an adjuvanted formulation," Vaccine, 29(7):1421-1430 (2010).

Donnelly et al., "Intravaginal immunization using the recombinant HIV-1 clade C trimeric envelope glycoprotein CN54gp140 formulated within lyophilized solid dosage forms," Vaccine, 29(27):4512-4520 (2011).

Krashias et al., "Potent adaptive immune responses induced against HIV-1 gp140 and influenza virus HA by a polyanionic carbomer," Vaccine, 28(13):2482-2489 (2010).

Dey et al., "Use of a polyanionic carbomer, Carbopol971P, in combination with MF59, improves antibody responses to HIV-1 envelope glycoprotein," Vaccine, 30(17):2749-2759 (2012).

International Preliminary Report on Patentability and Written Opinion for International Application No. PCT/US2012/065113, dated May 20, 2014.

Curran et al., "Vaginal delivery of the recombinant HIV-1 clade-C trimeric gp140 envelope protein CN54gp140 within novel rheologically structured vehicles elicits specific immune responses," Vaccine, 27:6791-6798 (2009).

Arias et al., "Carnauba wax nanoparticles enhance strong systemic and mucosal cellular and humoral immune responses to HIV-gp140 antigen," Vaccine, 29:1258-1269 (2011).

* cited by examiner

*Primary Examiner* — Ali Soroush
*Assistant Examiner* — Yanzhi Zhang
(74) *Attorney, Agent, or Firm* — Helen Lee; Virginia Campen

(57) ABSTRACT

The present invention relates to immunogenic complexes formed between polyanionic carbomers and Env polypeptides. Uses of the immunogenic complexes in applications including inducing an immune response and immunization generally are described. Methods of forming and manufacture of the immunogenic complexes are also described. The present invention also relates to immunogenic compositions including low viscosity, polyanionic carbomers and Env polypeptides. Uses of such immunogenic compositions in applications including inducing an immune response and immunization generally are described. Methods of manufacture of such immunogenic compositions are also described.

20 Claims, 60 Drawing Sheets

(A)

1. Mol. weight marker
2. 0hr incubation
3. 1hr incubation
4. 2hrs incubation
5. 3hrs incubation
6. 4hrs incubation (B)

1. Mol. Weight Marker
2. gp140ΔV2 – Carbopol (4°C)
3. gp140ΔV2 – Carbopol (20°C)
4. gp140ΔV2 – PBS (RT)
5. Mol. Weight Marker
6. gp140ΔV2 – Carbopol (30°C)
7. gp140ΔV2 – Carbopol (37°C)
8. gp140ΔV2 – PBS (37°C)

Figure 8A

| | | Tier 1a | | | Tier 1b | |
|---|---|---|---|---|---|---|
| | Rabbit | MW965.26 | SF162 | MN.3 | TV1c21 | Bal.26 |
| Du422.1 | 1 | 507 | <20 | <20 | 31 | <20 |
| | 2 | 401 | <20 | 25 | <20 | <20 |
| | 3 | 278 | <20 | <20 | 32 | <20 |
| | 4 | 1008 | 124 | 40 | 32 | <20 |
| | 5 | 213 | <20 | <20 | 30 | <20 |
| Du156.12 | 6 | 231 | 31 | <20 | 44 | <20 |
| | 7 | 332 | 56 | <20 | 37 | <20 |
| | 8 | 179 | 20 | <20 | 21 | <20 |
| | 9 | 299 | 30 | <20 | 28 | <20 |
| | 10 | 914 | 90 | 49 | 37 | <20 |
| CAP45.2.00.G3 | 11 | 605 | 140 | 55 | 39 | <20 |
| | 12 | 390 | <20 | <20 | <20 | <20 |
| | 13 | 516 | 360 | 406 | 22 | 23 |
| | 14 | 396 | 28 | <20 | <20 | <20 |
| | 15 | 466 | 34 | <20 | 39 | <20 |
| ZM249M.PL1 | 16 | 876 | <20 | 54 | <20 | <20 |
| | 17 | 444 | 129 | 88 | 50 | <20 |
| | 18 | 2481 | 323 | 44 | 80 | 25 |
| | 19 | 410 | 102 | <20 | 26 | <20 |
| | 20 | 2927 | 91 | 242 | 55 | <20 |
| EF117272 | 21 | 5602 | 217 | <20 | 127 | <20 |
| | 22 | 4163 | 789 | 37 | 88 | 27 |
| | 23 | 4837 | 121 | <20 | 28 | 21 |
| | 24 | 353 | 161 | <20 | 47 | <20 |
| | 25 | 6311 | 207 | 57 | 60 | <20 |
| EF203982 | 26 | 224 | <20 | <20 | 24 | <20 |
| | 27 | 546 | 52 | 21 | 34 | <20 |
| | 28 | 233 | 44 | 49 | <20 | <20 |
| | 29 | 579 | <20 | <20 | <20 | <20 |
| | 30 | 732 | 148 | 162 | <20 | <20 |
| EF203983 | 31 | 233 | 437 | 216 | 34 | 28 |
| | 32 | 373 | 110 | 79 | <20 | <20 |
| | 33 | 431 | 464 | 134 | 32 | <20 |
| | 34 | 418 | 206 | 198 | <20 | <20 |
| | 35 | 1372 | 2043 | 1898 | 93 | 88 |
| ZM249.PL1 + EF203983 + Du422.1 | 36 | 289 | 69 | 85 | 45 | <20 |
| | 37 | 2042 | 294 | 144 | 27 | <20 |
| | 38 | 381 | 48 | 134 | <20 | <20 |
| | 39 | 34 | 90 | 1676 | 33 | <20 |
| | 40 | 42 | 82 | 21 | 29 | <20 |
| ZM249.PL1 + EF203983 + Du422.1 + CARBOPOL(TM) | 41 | 3749 | 272 | 63 | 20 | <20 |
| | 42 | 1996 | 342 | 261 | 33 | <20 |
| | 43 | 2497 | 1984 | 44 | 28 | 40 |
| | 44 | 2116 | 100 | 110 | 26 | <20 |
| | 45 | 1583 | 166 | 58 | <20 | <20 |
| TV1 | 46 | 2186 | 1808 | 449 | 55 | 70 |
| | 47 | 401 | 228 | 307 | 29 | <20 |
| | 48 | 2953 | 475 | 210 | 42 | 23 |
| | 49 | 1243 | 148 | 109 | 37 | <20 |
| | 50 | 795 | 163 | 67 | 31 | <20 |

Figure 8B

| | | Tier 2 | | | | |
|---|---|---|---|---|---|---|
| | Rabbit | Du156.12 | ZM249M.PL1 | Du422.1 | TV1c8.2 | EF203983 |
| Du422.1 | 1 | 64 | <20 | <20 | <40 | <40 |
| | 2 | 36 | <20 | <20 | <40 | <40 |
| | 3 | 29 | <20 | <20 | <40 | <40 |
| | 4 | 51 | <20 | <20 | <40 | <40 |
| | 5 | 56 | 23 | <20 | <40 | <40 |
| Du156.12 | 6 | 59 | 21 | 21 | <40 | <40 |
| | 7 | 67 | 23 | 23 | <40 | <40 |
| | 8 | 72 | <20 | <20 | <40 | <40 |
| | 9 | 40 | <20 | <20 | <40 | <40 |
| | 10 | 99 | 22 | <20 | <40 | <40 |
| CAP45.2.00.G3 | 11 | 40 | <20 | 21 | <40 | <40 |
| | 12 | 30 | <20 | <20 | <40 | <40 |
| | 13 | 28 | <20 | <20 | <40 | <40 |
| | 14 | 32 | <20 | <20 | <40 | <40 |
| | 15 | 44 | 21 | 22 | <40 | <40 |
| ZM249M.PL1 | 16 | 22 | <20 | <20 | <40 | <40 |
| | 17 | 33 | 44 | 39 | <40 | <40 |
| | 18 | 50 | 67 | 44 | <40 | <40 |
| | 19 | 23 | <20 | 21 | <40 | <40 |
| | 20 | 58 | 50 | 80 | <40 | <40 |
| EF117272 | 21 | 99 | 82 | 87 | >40 | <40 |
| | 22 | 78 | 30 | 49 | >40 | <40 |
| | 23 | 21 | <20 | <20 | <40 | <40 |
| | 24 | 52 | 29 | 43 | <40 | <40 |
| | 25 | 38 | 22 | 48 | <40 | <40 |
| EF203982 | 26 | 30 | <20 | 39 | <40 | <40 |
| | 27 | <20 | 21 | <20 | <40 | <40 |
| | 28 | <20 | <20 | <20 | <40 | <40 |
| | 29 | <20 | <20 | <20 | <40 | <40 |
| | 30 | <20 | <20 | 20 | <40 | <40 |
| EF203983 | 31 | 35 | 34 | 26 | <40 | <40 |
| | 32 | 22 | 21 | 26 | <40 | <40 |
| | 33 | 52 | 38 | 32 | <40 | <40 |
| | 34 | <20 | 21 | 21 | <40 | <40 |
| | 35 | 44 | 46 | 64 | >40 | <40 |
| ZM249.PL1 + EF203983 + Du422.1 | 36 | 30 | 39 | 37 | <40 | <40 |
| | 37 | 29 | 25 | <20 | >40 | <40 |
| | 38 | 32 | 48 | <20 | <40 | <40 |
| | 39 | 50 | 39 | <20 | <40 | <40 |
| | 40 | 23 | 135 | <20 | <40 | <40 |
| ZM249.PL1 + EF203983 + Du422.1 + CARBOPOL(TM) | 41 | 22 | 33 | <20 | >40 | <40 |
| | 42 | 22 | <20 | <20 | >40 | <40 |
| | 43 | 21 | <20 | <20 | >40 | <40 |
| | 44 | <20 | 33 | <20 | >40 | <40 |
| | 45 | <20 | <20 | <20 | <40 | <40 |
| TV1 | 46 | 41 | 37 | <20 | >40 | <40 |
| | 47 | 21 | <20 | <20 | >40 | <40 |
| | 48 | <20 | 27 | <20 | >40 | <40 |
| | 49 | <20 | 25 | <20 | <40 | <40 |
| | 50 | 21 | <20 | <20 | <40 | <40 |

| | | Tier 1a | | | Tier 1b | |
|---|---|---|---|---|---|---|
| | Rabbit | MW965.26 | SF162 | MN.3 | Bal.26 | TV1.21 |
| Du156.1 | 1 | 5007 | 159 | 111 | <20 | 69 |
| | 2 | 3655 | 539 | 436 | 31 | 70 |
| | 3 | 3708 | 1959 | 492 | 56 | 67 |
| | 4 | 3346 | 399 | 54 | <20 | 35 |
| | 5 | 31205 | 668 | 32 | <20 | 43 |
| Du422.1 | 6 | 7809 | 545 | 23 | <20 | 26 |
| | 7 | 1209 | 154 | 48 | <20 | 54 |
| | 8 | 1143 | 377 | 105 | <20 | 31 |
| | 9 | 1578 | 440 | 39 | <20 | <20 |
| | 10 | 6289 | 118 | 56 | <20 | 47 |
| ZM249.PL1 | 11 | 19659 | 1412 | 302 | 30 | 96 |
| | 12 | 1651 | 880 | 152 | <20 | <20 |
| | 13 | 5449 | 1277 | 135 | 39 | 50 |
| | 14 | 2214 | 1471 | 193 | 23 | 38 |
| | 15 | 7623 | 1250 | 175 | <20 | 73 |
| EF203983 | 16 | 25038 | 17849 | 1731 | 422 | 165 |
| | 17 | 18495 | 7344 | 556 | 175 | 126 |
| | 18 | 4954 | 2018 | 590 | 47 | 88 |
| | 19 | 4758 | 4136 | 292 | 186 | 107 |
| | 20 | 2678 | 526 | 171 | <20 | 41 |
| TV1 | 21 | 1603 | 2199 | 2362 | 51 | 113 |
| | 22 | 4740 | 5663 | 232 | 92 | 90 |
| | 23 | 8716 | 2415 | 342 | 51 | 138 |
| | 24 | 12082 | 3056 | 882 | 39 | 199 |
| | 25 | 4962 | 2661 | 2930 | 86 | 117 |
| TV1 DV2 | 26 | 9517 | 3200 | 2892 | 95 | 70 |
| | 27 | 17855 | 6563 | 2476 | 143 | 157 |
| | 28 | 25924 | 2759 | 3671 | 139 | 134 |
| | 29 | 11161 | 2276 | 413 | 117 | 105 |
| | 30 | 19638 | 1091 | 769 | 33 | 87 |
| SF162 DV2 | 31 | 3599 | 5980 | 5710 | 266 | 50 |
| | 32 | 1682 | 4619 | 966 | 102 | 36 |
| | 33 | 2193 | 2189 | 1178 | 32 | 28 |
| | 34 | 3518 | 2515 | 1445 | 55 | 42 |
| | 35 | 10654 | 4533 | 3214 | 81 | 62 |
| TV1 + ZM249.PL1 + EF203983 + Du422.1 | 46 | 2808 | 1271 | 1060 | 40 | 65 |
| | 47 | 6293 | 1853 | 120 | <20 | 95 |
| | 48 | 6764 | 4742 | 1224 | 107 | 74 |
| | 49 | 9185 | 2859 | 291 | 49 | 91 |
| | 50 | >43740 | 2514 | 860 | 50 | 178 |
| 1. EF203983; 2. Du422.1; 3. ZM249.PL1; 4. TV1 | 51 | 5783 | 2568 | 84 | 50 | 55 |
| | 52 | 13819 | 3684 | 171 | 133 | 76 |
| | 53 | 6670 | 1419 | 353 | 34 | 88 |
| | 54 | 2283 | 485 | 70 | <20 | 37 |
| | 55 | NA | NA | NA | NA | NA |

Figure 12B

| | Rabbit | Tier 2 DU156.12 | Tier 2 DU422.1 | Tier 2 ZM249M.PL1 |
|---|---|---|---|---|
| Du156.1 | 1 | <20 | <20 | <20 |
| | 2 | 21 | 22 | <20 |
| | 3 | 78 | <20 | <20 |
| | 4 | <20 | <20 | <20 |
| | 5 | <20 | <20 | <20 |
| Du422.1 | 6 | <20 | <20 | <20 |
| | 7 | 25 | 22 | <20 |
| | 8 | <20 | <20 | <20 |
| | 9 | <20 | <20 | <20 |
| | 10 | <20 | <20 | <20 |
| ZM249.PL1 | 11 | <20 | <20 | 28 |
| | 12 | <20 | <20 | <20 |
| | 13 | <20 | <20 | <20 |
| | 14 | <20 | <20 | <20 |
| | 15 | 24 | <20 | 21 |
| EF203983 | 16 | <20 | <20 | <20 |
| | 17 | <20 | <20 | <20 |
| | 18 | <20 | <20 | <20 |
| | 19 | <20 | <20 | <20 |
| | 20 | <20 | <20 | <20 |
| TV1 | 21 | 21 | 21 | <20 |
| | 22 | 31 | 27 | 23 |
| | 23 | 30 | 24 | 23 |
| | 24 | 54 | 34 | 37 |
| | 25 | 22 | <20 | <20 |
| TV1 DV2 | 26 | <20 | <20 | <20 |
| | 27 | <20 | <20 | <20 |
| | 28 | <20 | <20 | <20 |
| | 29 | <20 | <20 | <20 |
| | 30 | <20 | <20 | <20 |
| SF162 DV2 | 31 | <20 | <20 | <20 |
| | 32 | <20 | <20 | <20 |
| | 33 | <20 | <20 | <20 |
| | 34 | <20 | <20 | <20 |
| | 35 | <20 | <20 | <20 |
| TV1 + ZM249.PL1 + EF203983 + Du422.1 | 46 | <20 | 24 | 21 |
| | 47 | <20 | <20 | <20 |
| | 48 | <20 | <20 | <20 |
| | 49 | 30 | 20 | <20 |
| | 50 | 40 | <20 | <20 |
| 1. EF203983; 2. Du422.1; 3. ZM249.PL1; 4. TV1 | 51 | <20 | <20 | <20 |
| | 52 | <20 | <20 | <20 |
| | 53 | <20 | <20 | <20 |
| | 54 | <20 | <20 | <20 |
| | 55 | NA | NA | NA |

Figure 13A

| | Rabbit | MW965.26 | SF162 | MN | TV1c8.2 | TV1c21 |
|---|---|---|---|---|---|---|
| Du156.12 | 1 | 2266 | 120 | 138 | 252 | 59 |
| | 2 | 2177 | 222 | 455 | 274 | 104 |
| | 3 | 1244 | 406 | 608 | 134 | 49 |
| | 4 | 1963 | 190 | 187 | 189 | 100 |
| | 5 | 5567 | 296 | 268 | 331 | 219 |
| Du422.1 | 6 | 2973 | 418 | 32 | 146 | 51 |
| | 7 | 1687 | 187 | 195 | 109 | 80 |
| | 8 | 890 | 193 | 189 | 70 | 59 |
| | 9 | 5603 | 1802 | 810 | 480 | 79 |
| | 10 | 3807 | 543 | 93 | 369 | 106 |
| ZM249.PL1 | 11 | 7671 | 884 | 324 | 374 | 80 |
| | 12 | 3518 | 1905 | 608 | 401 | 49 |
| | 13 | 3531 | 938 | 130 | 349 | 39 |
| | 14 | 3401 | 1474 | 303 | 174 | 80 |
| | 15 | 6086 | 1304 | 300 | 177 | 180 |
| EF203983 | 16 | 10957 | 6907 | 728 | 388 | 77 |
| | 17 | 8321 | 4230 | 739 | 738 | 194 |
| | 18 | 2975 | 866 | 639 | 384 | 99 |
| | 19 | 6719 | 6536 | 1269 | 644 | 166 |
| | 20 | 4145 | 1513 | 670 | 391 | 142 |
| TV1 | 21 | 4624 | 4339 | 5244 | 485 | 154 |
| | 22 | 3669 | 3152 | 372 | 267 | 119 |
| | 23 | 6484 | 1397 | 607 | 463 | 184 |
| | 24 | 8310 | 1428 | 410 | 471 | 245 |
| | 25 | 10838 | 2336 | 2084 | 335 | 168 |
| TV1 DV2 | 26 | 6812 | 3030 | 1238 | 416 | 74 |
| | 27 | 5383 | 6088 | 7218 | 705 | 189 |
| | 28 | 10300 | 3779 | 5734 | 590 | 196 |
| | 29 | 6668 | 2239 | 1125 | 596 | 200 |
| | 30 | 4422 | 1180 | 799 | 352 | 152 |
| SF162 DV2 | 31 | 2571 | 4166 | 4067 | 339 | 97 |
| | 32 | 1171 | 2215 | 1683 | 256 | 47 |
| | 33 | 2309 | 3059 | 3629 | 320 | 58 |
| | 34 | 2638 | 2006 | 2786 | 195 | 79 |
| | 35 | 2738 | 3496 | 3112 | 295 | 85 |
| TV1 + ZM249.PL1 + EF203983 + Du422.1 | 46 | 1497 | 585 | 380 | 153 | 39 |
| | 47 | 5200 | 993 | 226 | 233 | 119 |
| | 48 | 3956 | 904 | 785 | 420 | 78 |
| | 49 | 4377 | 1139 | 323 | 257 | 81 |
| | 50 | 8601 | 1146 | 602 | 386 | 205 |
| 1. EF203983; 2. Du422.1; 3. ZM249M.PL1; 4. TV1 | 51 | 5509 | 2255 | 91 | 393 | 142 |
| | 52 | 18895 | 6510 | 1093 | 657 | 182 |
| | 53 | 3212 | 1448 | 791 | 223 | 123 |
| | 54 | 4569 | 1219 | 249 | 331 | 133 |

| | Rabbit | DU156.12 | DU422.1 | ZM249M.PL1 | EF203960 | EF203983 |
|---|---|---|---|---|---|---|
| Du156.12 | 1 | <20 | 37 | 30 | <20 | <20 |
| | 2 | 46 | 26 | 24 | <20 | <20 |
| | 3 | 383 | 45 | 43 | 35 | <20 |
| | 4 | 36 | 62 | 66 | 37 | <20 |
| | 5 | 193 | 90 | 96 | 31 | 36 |
| Du422.1 | 6 | 27 | <20 | <20 | 37 | <20 |
| | 7 | 38 | 81 | 75 | 54 | <20 |
| | 8 | 20 | 29 | 38 | <20 | <20 |
| | 9 | <20 | <20 | <20 | <20 | <20 |
| | 10 | 26 | 29 | 28 | 40 | <20 |
| ZM249.PL1 | 11 | 23 | 23 | 143 | 40 | <20 |
| | 12 | <20 | <20 | 35 | 33 | <20 |
| | 13 | <20 | <20 | 50 | 26 | <20 |
| | 14 | 54 | 54 | 47 | <20 | <20 |
| | 15 | 42 | <20 | 37 | 48 | <20 |
| EF203983 | 16 | <20 | <20 | <20 | 37 | <20 |
| | 17 | <20 | 44 | 42 | 61 | <20 |
| | 18 | <20 | <20 | <20 | <20 | <20 |
| | 19 | 25 | <20 | <20 | <20 | <20 |
| | 20 | <20 | <20 | <20 | 37 | <20 |
| TV1 | 21 | <20 | 35 | 39 | <20 | <20 |
| | 22 | <20 | 33 | 40 | <20 | <20 |
| | 23 | 38 | 39 | 50 | <20 | <20 |
| | 24 | 36 | 52 | 66 | 67 | <20 |
| | 25 | <20 | 40 | 40 | 43 | 38 |
| TV1 DV2 | 26 | <20 | 23 | 23 | 37 | <20 |
| | 27 | <20 | 36 | 27 | 77 | <20 |
| | 28 | <20 | 34 | 30 | 77 | <20 |
| | 29 | <20 | 31 | 25 | 54 | <20 |
| | 30 | 25 | 57 | 40 | 200 | <20 |
| SF162 DV2 | 31 | 27 | 50 | 41 | 264 | <20 |
| | 32 | <20 | 37 | 35 | 207 | <20 |
| | 33 | <20 | 35 | 39 | 40 | <20 |
| | 34 | <20 | 41 | 33 | <20 | <20 |
| | 35 | <20 | <20 | <20 | <20 | <20 |
| TV1 + ZM249.PL1 + EF203983 + Du422.1 | 46 | <20 | 27 | 28 | <20 | <20 |
| | 47 | 33 | 28 | 34 | <20 | <20 |
| | 48 | 22 | 39 | 30 | <20 | <20 |
| | 49 | 23 | 44 | 43 | 31 | <20 |
| | 50 | 54 | 71 | 80 | 263 | <20 |
| 1. EF203983; 2. Du422.1; 3. ZM249M.PL1; 4. TV1 | 51 | <20 | 33 | 28 | 219 | <20 |
| | 52 | <20 | 33 | 35 | 259 | <20 |
| | 53 | 37 | 72 | 98 | 312 | <20 |
| | 54 | 23 | 38 | 29 | 194 | <20 |

Figure 13B

| | Rabbit | EF203982 | EF203963 | EF203985 | EF203970 | EF117272 |
|---|---|---|---|---|---|---|
| Du156.12 | 1 | <20 | <20 | <20 | <20 | <20 |
| | 2 | <20 | <20 | <20 | <20 | <20 |
| | 3 | <20 | <20 | <20 | <20 | <20 |
| | 4 | <20 | <20 | <20 | <20 | <20 |
| | 5 | <20 | <20 | <20 | <20 | <20 |
| Du422.1 | 6 | <20 | <20 | <20 | <20 | <20 |
| | 7 | <20 | <20 | <20 | <20 | <20 |
| | 8 | <20 | <20 | <20 | <20 | <20 |
| | 9 | <20 | <20 | <20 | <20 | <20 |
| | 10 | <20 | <20 | <20 | <20 | <20 |
| ZM249.PL1 | 11 | <20 | <20 | <20 | <20 | <20 |
| | 12 | <20 | <20 | <20 | <20 | <20 |
| | 13 | <20 | <20 | <20 | <20 | <20 |
| | 14 | <20 | <20 | <20 | <20 | <20 |
| | 15 | <20 | <20 | <20 | <20 | <20 |
| EF203983 | 16 | <20 | <20 | <20 | <20 | <20 |
| | 17 | <20 | <20 | <20 | <20 | <20 |
| | 18 | <20 | <20 | <20 | <20 | <20 |
| | 19 | <20 | <20 | <20 | <20 | <20 |
| | 20 | <20 | <20 | <20 | <20 | <20 |
| TV1 | 21 | <20 | <20 | <20 | <20 | <20 |
| | 22 | <20 | <20 | <20 | <20 | <20 |
| | 23 | <20 | <20 | <20 | <20 | <20 |
| | 24 | <20 | <20 | <20 | <20 | <20 |
| | 25 | <20 | <20 | <20 | <20 | <20 |
| TV1 DV2 | 26 | <20 | <20 | <20 | <20 | <20 |
| | 27 | <20 | <20 | <20 | <20 | <20 |
| | 28 | <20 | <20 | <20 | <20 | <20 |
| | 29 | <20 | <20 | <20 | <20 | <20 |
| | 30 | <20 | <20 | <20 | <20 | <20 |
| SF162 DV2 | 31 | <20 | <20 | <20 | <20 | <20 |
| | 32 | <20 | <20 | <20 | <20 | <20 |
| | 33 | <20 | <20 | <20 | <20 | <20 |
| | 34 | <20 | <20 | <20 | <20 | <20 |
| | 35 | <20 | <20 | <20 | <20 | <20 |
| TV1 + ZM249.PL1 + EF203983 + Du422.1 | 46 | <20 | <20 | <20 | <20 | <20 |
| | 47 | <20 | <20 | <20 | <20 | <20 |
| | 48 | <20 | <20 | <20 | <20 | <20 |
| | 49 | <20 | <20 | <20 | <20 | <20 |
| | 50 | <20 | <20 | <20 | <20 | <20 |
| 1. EF203983; 2. Du422.1; 3. ZM249M.PL1; 4. TV1 | 51 | <20 | <20 | <20 | <20 | <20 |
| | 52 | <20 | <20 | <20 | <20 | <20 |
| | 53 | <20 | <20 | <20 | <20 | <20 |
| | 54 | <20 | <20 | <20 | <20 | <20 |

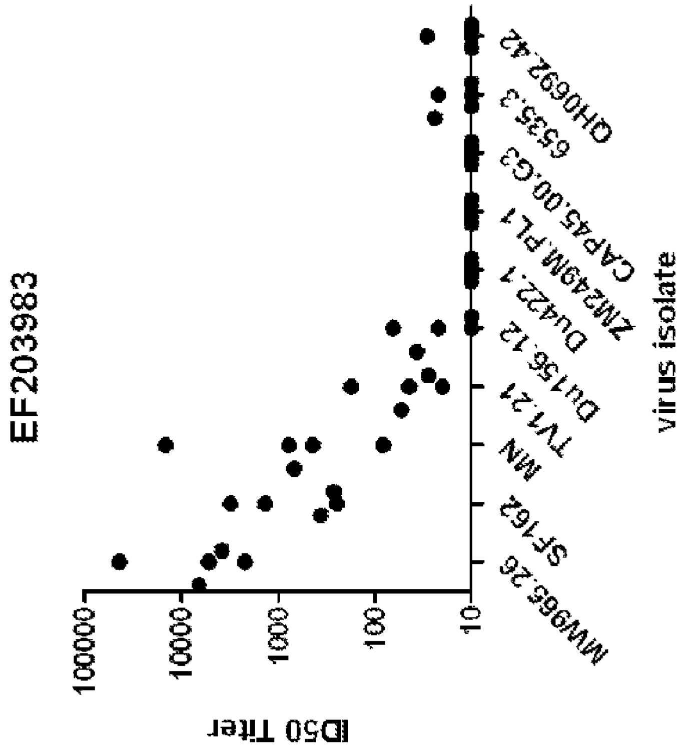
Figure 17C
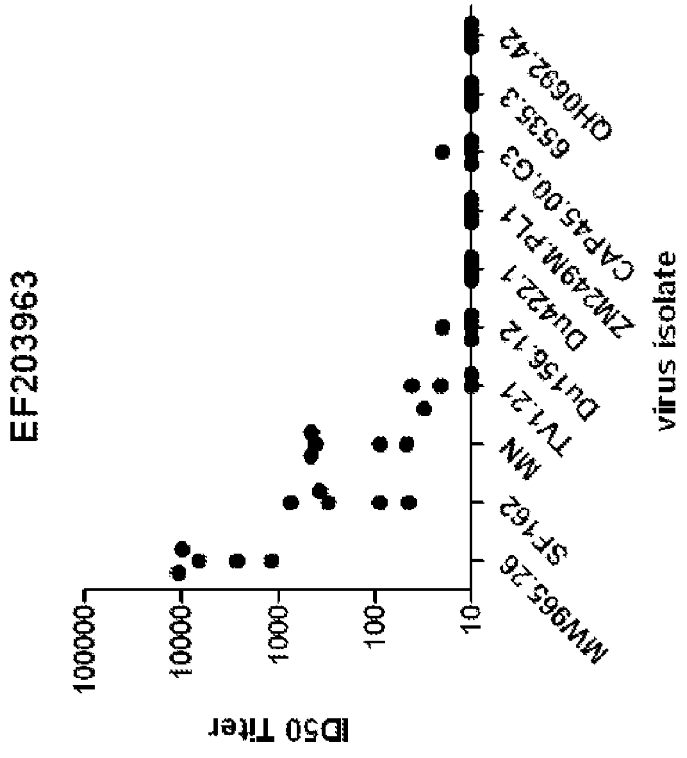

Figure 18A

| | Rabbit | Tier 1A: MW965.26 | Tier 1A: SF162 | Tier 1A: MN |
|---|---|---|---|---|
| Du156.12 | 1 | 13123 | 344 | 153 |
| | 2 | 19721 | 111 | 37 |
| | 3 | 7959 | 274 | 102 |
| | 4 | 5129 | 147 | 57 |
| | 5 | 4044 | 291 | <20 |
| Du422.1 | 6 | 789 | <20 | 20 |
| | 7 | 1862 | <20 | <20 |
| | 8 | 6649 | <20 | <20 |
| | 9 | 5392 | 82 | <20 |
| | 10 | 4681 | 103 | <20 |
| ZM249.PL1 | 11 | >43740 | 1156 | 235 |
| | 12 | 27551 | 1268 | 450 |
| | 13 | 10978 | 191 | 128 |
| | 14 | >43740 | 1898 | 346 |
| | 15 | >43740 | 2971 | 7889 |
| EF203960 | 16 | 4907 | 1227 | 1015 |
| | 17 | 23043 | 5120 | 6179 |
| | 18 | 6523 | 484 | 1130 |
| | 19 | 5040 | 761 | 1928 |
| | 20 | 24679 | 3502 | 269 |
| EF203963 | 21 | 9862 | 306 | 461 |
| | 22 | 10718 | 88 | 88 |
| | 23 | 6656 | 745 | 458 |
| | 24 | 1181 | 45 | 47 |
| | 25 | 2661 | 375 | 405 |
| EF203983 | 26 | 6613 | 1360 | 83 |
| | 27 | 5246 | 3122 | 443 |
| | 28 | >43740 | 367 | 14457 |
| | 29 | 3857 | 246 | 779 |
| | 30 | 2208 | 268 | 684 |
| TV1 | 31 | >43740 | 332 | 1822 |
| | 32 | 5100 | 184 | 51 |
| | 33 | 6298 | 51 | 480 |
| | 34 | 4420 | 81 | 150 |
| | 35 | 233 | 27 | 33 |

| | | Tier 2 | | | | | | |
|---|---|---|---|---|---|---|---|---|
| | Rabbit | TV1.21 | DU156.12 | DU422.1 | ZM249M.PL1 | CAP45.00.G3 | 6535.3 | QH0692.42 |
| Du156.12 | 1 | 32 | <20 | <20 | <20 | <20 | <20 | <20 |
| | 2 | <20 | <20 | <20 | <20 | <20 | <20 | <20 |
| | 3 | 72 | 27 | <20 | <20 | <20 | 39 | 39 |
| | 4 | <20 | <20 | <20 | <20 | <20 | <20 | <20 |
| | 5 | <20 | <20 | <20 | <20 | <20 | <20 | <20 |
| Du422.1 | 6 | <20 | <20 | <20 | <20 | <20 | <20 | <20 |
| | 7 | <20 | <20 | <20 | <20 | <20 | <20 | <20 |
| | 8 | <20 | <20 | <20 | <20 | <20 | <20 | <20 |
| | 9 | <20 | <20 | <20 | <20 | <20 | <20 | <20 |
| | 10 | <20 | <20 | <20 | <20 | <20 | <20 | <20 |
| ZM249.PL1 | 11 | 28 | <20 | <20 | <20 | <20 | <20 | <20 |
| | 12 | 57 | 25 | <20 | <20 | <20 | <20 | 21 |
| | 13 | 21 | <20 | <20 | <20 | <20 | <20 | <20 |
| | 14 | 40 | <20 | <20 | <20 | <20 | <20 | <20 |
| | 15 | 48 | <20 | <20 | 35 | <20 | <20 | <20 |
| EF203960 | 16 | 21 | <20 | <20 | <20 | 110 | <20 | <20 |
| | 17 | 47 | <20 | <20 | <20 | <20 | <20 | <20 |
| | 18 | 36 | <20 | <20 | <20 | <20 | <20 | <20 |
| | 19 | 28 | <20 | <20 | <20 | <20 | <20 | <20 |
| | 20 | 25 | <20 | <20 | <20 | 68 | <20 | <20 |
| EF203963 | 21 | <20 | <20 | <20 | <20 | <20 | <20 | <20 |
| | 22 | 42 | 20 | <20 | <20 | <20 | <20 | <20 |
| | 23 | 31 | <20 | <20 | <20 | <20 | <20 | <20 |
| | 24 | <20 | <20 | <20 | <20 | 20 | <20 | <20 |
| | 25 | 21 | <20 | <20 | <20 | <20 | <20 | <20 |
| EF203983 | 26 | 20 | <20 | <20 | <20 | <20 | <20 | <20 |
| | 27 | 28 | <20 | <20 | <20 | <20 | <20 | <20 |
| | 28 | 177 | 65 | <20 | <20 | <20 | 22 | 29 |
| | 29 | 44 | 37 | <20 | <20 | <20 | <20 | <20 |
| | 30 | 53 | 22 | <20 | <20 | <20 | 24 | <20 |
| TV1 | 31 | 137 | 28 | <20 | <20 | <20 | 39 | 22 |
| | 32 | 66 | 31 | <20 | <20 | <20 | 20 | <20 |
| | 33 | 57 | 46 | <20 | <20 | <20 | <20 | <20 |
| | 34 | 50 | 40 | <20 | <20 | <20 | <20 | <20 |
| | 35 | <20 | <20 | <20 | <20 | <20 | <20 | <20 |

| Epitope | mAb | Du156 | | | | | Du422 | | | | ZM249 | | | | |
|---|---|---|---|---|---|---|---|---|---|---|---|---|---|---|---|
| | | 1 | 2 | 3 | 4 | 5 | 6 | 7 | 8 | 10 | 11 | 12 | 13 | 14 | 15 |
| CD4bs | A32 | 90.68 | 87.37 | 93.73 | 92.45 | 83.72 | 93.23 | 79.72 | 91.20 | 98.01 | 61.41 | 78.61 | 67.25 | 78.17 | 73.89 |
| V3 | 2557 | 22.79 | 34.31 | 26.04 | 9.26 | 12.91 | 63.69 | 50.31 | 35.05 | 41.62 | 19.02 | 15.02 | 34.59 | 16.34 | 8.31 |
| CD4i | E51 | 44.54 | 48.25 | 49.99 | 35.80 | 47.10 | 80.77 | 64.99 | 70.02 | 64.32 | 22.26 | 21.43 | 34.11 | 18.85 | 10.87 |
| C1-C4 | EH21 | 79.95 | 89.39 | 87.08 | 89.94 | 75.83 | 100.27 | 116.05 | 103.57 | 100.83 | 73.81 | 106.00 | 84.22 | 82.56 | 74.91 |

| Epitope | mAb | EF203960 | | | | | EF203963 | | | | | EF203983 | | | | |
|---|---|---|---|---|---|---|---|---|---|---|---|---|---|---|---|---|
| | | 16 | 17 | 18 | 19 | 20 | 21 | 22 | 23 | 24 | 25 | 26 | 27 | 28 | 29 | 30 |
| CD4bs | A32 | 70.03 | 74.08 | 82.43 | 50.22 | 69.54 | 70.16 | 74.88 | 87.88 | 84.91 | 83.58 | 94.24 | 92.97 | 78.76 | 93.64 | 88.10 |
| V3 | 2557 | 20.83 | 10.97 | 30.01 | 13.99 | 11.47 | 27.08 | 33.42 | 23.90 | 58.43 | 44.69 | 33.31 | 22.09 | 9.96 | 21.48 | 30.56 |
| CD4i | E51 | 32.33 | 19.09 | 53.40 | 11.29 | 28.12 | 22.64 | 28.74 | 50.81 | 63.92 | 57.10 | 55.50 | 35.23 | 42.11 | 51.45 | 56.15 |
| C1-C4 | EH21 | 81.64 | 75.48 | 84.01 | 112.85 | 118.33 | 118.21 | 91.21 | 103.47 | 81.91 | 92.56 | 92.81 | 92.79 | 92.30 | 90.92 | 101.40 |

| Epitope | mAb | TV1 | | | | | SF162 | | | | |
|---|---|---|---|---|---|---|---|---|---|---|---|
| | | 31 | 32 | 33 | 34 | 35 | 36 | 37 | 38 | 39 | 40 |
| CD4bs | A32 | 46.24 | 70.42 | 51.80 | 45.39 | 66.48 | 42.09 | 40.64 | 83.43 | 61.24 | 48.39 |
| V3 | 2557 | 7.70 | 15.05 | 22.09 | 30.40 | 61.06 | 49.24 | 27.91 | 64.51 | 46.50 | 32.34 |
| CD4i | E51 | 9.56 | 19.11 | 8.49 | 4.09 | 35.12 | 5.53 | 3.20 | 14.64 | 17.33 | 10.78 |
| C1-C4 | EH21 | 57.46 | 59.03 | 59.53 | 63.24 | 73.42 | 72.47 | 66.24 | 92.11 | 95.80 | 86.02 |

0 - 15 %
16 - 30 %
31 - 50 %
51 - 75 %
> 75 %

| Epitope | mAb | TV1-gp140 | | | | | SF162-gp140 | | | | | EF203983 / Du422 / ZM249 / TV1 | | | | |
|---|---|---|---|---|---|---|---|---|---|---|---|---|---|---|---|---|
| | | 41 | 42 | 43 | 44 | 45 | 46 | 47 | 48 | 49 | 50 | 51 | 52 | 53 | 54 | 55 |
| CD4bs | A32 | 33.12 | 34.13 | 49.27 | 47.58 | 50.30 | 65.49 | 65.18 | 41.45 | 72.96 | 40.78 | 102.17 | 79.74 | 89.47 | 89.38 | 83.92 |
| V3 | 2557 | 7.20 | 15.93 | 21.26 | 15.42 | 9.11 | 59.19 | 73.97 | 40.77 | 78.76 | 71.51 | 31.87 | 12.49 | 26.16 | 43.33 | 19.04 |
| CD4i | E51 | 4.85 | 5.42 | 5.51 | 8.35 | 5.88 | 19.50 | 20.22 | 7.96 | 31.58 | 8.00 | 58.72 | 40.86 | 53.23 | 55.47 | 53.88 |
| C1-C4 | EH21 | 55.31 | 61.29 | 65.17 | 75.35 | 63.51 | 77.91 | 84.30 | 74.27 | 89.13 | 66.47 | 83.48 | 86.81 | 89.92 | 100.63 | 95.50 |

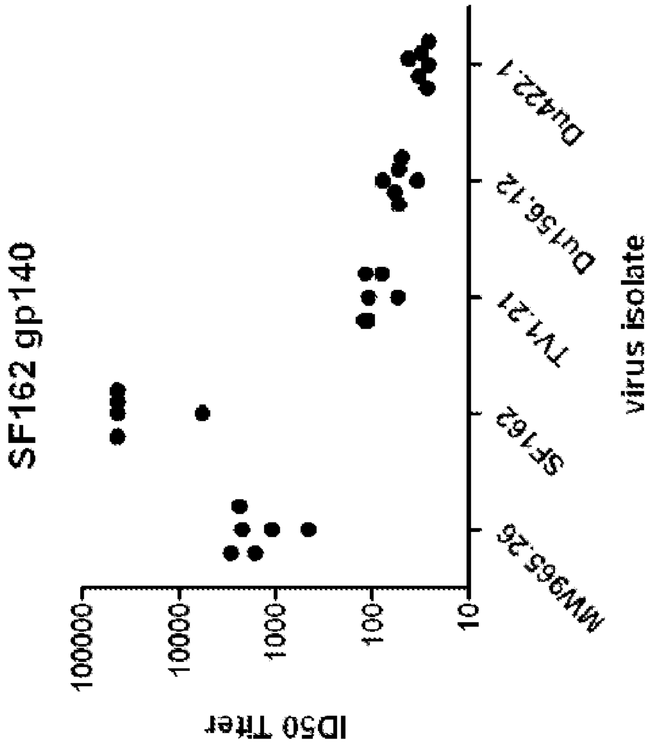
Figure 20E
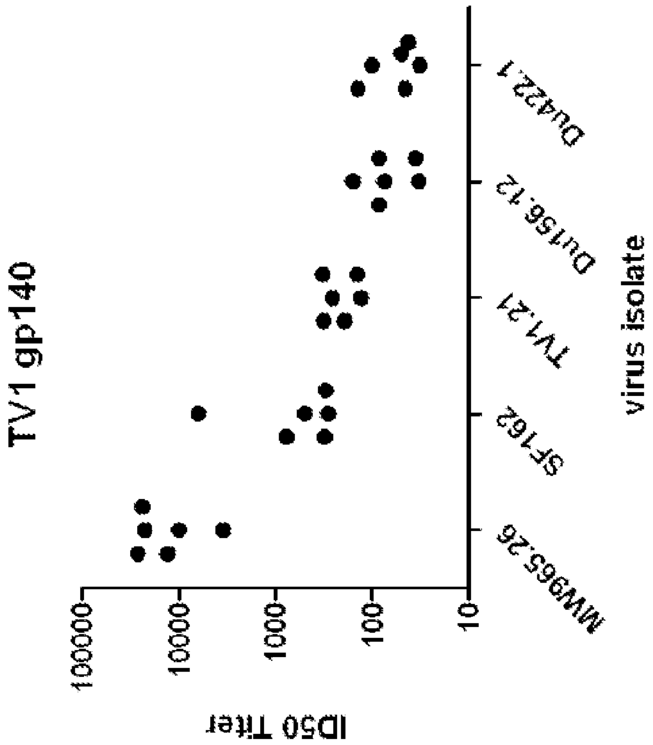

|  |  | Tier 1A |  | Tier 2 |  |  |
|---|---|---|---|---|---|---|
|  | Guinea pig | MW965.26 | SF162 | TV1.21 | DU156.12 | DU422.1 |
| Du156.12 | 1 | 12687 | 312 | 67 | <20 | 20 |
|  | 2 | 7085 | <20 | 29 | <20 | <20 |
|  | 3 | 11155 | 48 | 42 | <20 | <20 |
|  | 4 | 24319 | <20 | 58 | <20 | <20 |
|  | 5 | 31156 | 77 | 140 | <20 | <20 |
|  | 6 | 16636 | 75 | 65 | <20 | <20 |
| Du422.1 | 7 | 42086 | 1856 | 114 | 20 | <20 |
|  | 8 | 21717 | 21 | 51 | <20 | <20 |
|  | 9 | 43070 | 1875 | 64 | <20 | <20 |
|  | 10 | 41233 | 453 | 137 | <20 | 20 |
|  | 11 | 23440 | 69 | 81 | <20 | 29 |
|  | 12 | >43740 | 62 | 169 | <20 | 22 |
| ZM249.PL1 | 13 | >43740 | 3902 | 238 | <20 | <20 |
|  | 14 | >43740 | 7296 | 345 | 32 | 46 |
|  | 15 | >43740 | 8848 | 306 | 20 | 21 |
|  | 16 | >43740 | 5270 | 235 | <20 | 21 |
|  | 17 | >43740 | 698 | 44 | <20 | <20 |
|  | 18 | >43740 | 2939 | 272 | 28 | 30 |
| EF203960 | 19 | 7647 | 1641 | 53 | <20 | <20 |
|  | 20 | 5771 | 368 | 46 | <20 | 23 |
|  | 21 | 12665 | 1461 | 60 | <20 | <20 |
|  | 22 | 19599 | 2152 | 102 | <20 | 21 |
|  | 23 | 40830 | 3451 | 177 | <20 | <20 |
|  | 24 | 26302 | 3866 | 136 | <20 | <20 |
| EF203963 | 25 | 33090 | 2559 | 109 | <20 | <20 |
|  | 26 | 22260 | 671 | 97 | 27 | 27 |
|  | 27 | >43740 | 2113 | 88 | <20 | <20 |
|  | 28 | 7066 | 181 | <20 | <20 | <20 |
|  | 29 | >43740 | 1840 | 108 | <20 | <20 |
|  | 30 | >43740 | 1116 | 105 | <20 | <20 |
| EF203983 | 31 | >43740 | 1988 | 148 | 21 | <20 |
|  | 32 | >43740 | 2978 | 117 | <20 | <20 |
|  | 33 | >43740 | 10356 | 123 | <20 | <20 |
|  | 34 | >43740 | 372 | 75 | <20 | <20 |
|  | 35 | >43740 | 3149 | 415 | 69 | 26 |
|  | 36 | >3740 | 458 | 91 | <20 | <20 |
| TV1 | 37 | 456 | 28 | 22 | <20 | <20 |
|  | 38 | >43740 | 2499 | 95 | <20 | <20 |
|  | 39 | 273 | 759 | 44 | <20 | <20 |
|  | 40 | >43740 | 306 | 110 | 26 | NA |
|  | 41 | 35 | 266 | 54 | 29 | 27 |
|  | 42 | 1584 | 645 | 183 | 49 | 66 |

| Epitope | mAb | Du156.12 gp120 | | | | | | Du422.1 gp120 | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| CD4bs | A32 | 85.60 | 86.47 | 83.86 | 81.86 | 83.28 | 84.46 | 73.61 | 85.21 | 74.21 | 72.12 | 79.58 | 77.94 |
| V3 | 2557 | 13.72 | 20.49 | 14.04 | 15.38 | 6.06 | 9.36 | 6.82 | 13.76 | 6.11 | 5.95 | 10.75 | 11.95 |
| CD4i | E51 | 46.98 | 54.46 | 35.80 | 74.91 | 34.58 | 30.00 | 23.69 | 33.70 | 27.64 | 31.55 | 37.45 | 37.65 |
| C1-C4 | EH21 | 81.08 | 84.10 | 98.72 | 93.99 | 89.26 | 90.52 | 110.43 | 96.20 | 85.05 | 82.04 | 105.06 | 81.19 |

| Epitope | mAb | ZM249M.PL1 gp120 | | | | | | EF203960 gp120 | | | | | |
|---|---|---|---|---|---|---|---|---|---|---|---|---|---|
| | | 13 | 14 | 15 | 16 | 17 | 18 | 19 | 20 | 21 | 22 | 23 | 24 |
| CD4bs | A32 | 70.08 | 72.13 | 77.13 | 71.98 | 80.44 | 72.38 | 87.60 | 87.07 | 78.40 | 76.58 | Serum Exhausted | 78.57 |
| V3 | 2557 | 4.96 | 7.66 | 6.49 | 7.58 | 13.45 | 6.77 | 13.76 | 20.15 | 11.12 | 9.80 | | 10.64 |
| CD4i | E51 | 31.75 | 36.55 | 19.32 | 29.44 | 32.27 | 22.70 | 38.91 | 40.31 | 33.40 | 37.11 | | 42.21 |
| C1-C4 | EH21 | 77.28 | 96.14 | 82.50 | 87.24 | 83.87 | 74.06 | 82.72 | 88.28 | 70.03 | 83.84 | | 79.94 |

| Epitope | mAb | EF203963 gp120 | | | | | | EF203983 gp120 | | | | | |
|---|---|---|---|---|---|---|---|---|---|---|---|---|---|
| | | 25 | 26 | 27 | 28 | 29 | 30 | 31 | 32 | 33 | 34 | 35 | 36 |
| CD4bs | A32 | 85.36 | 83.64 | 82.19 | 83.57 | 85.07 | 89.14 | 90.84 | 87.30 | 77.72 | 80.91 | 75.98 | 86.84 |
| V3 | 2557 | 8.24 | 12.30 | 6.62 | 19.81 | 6.22 | 7.31 | 9.44 | 6.67 | 6.72 | 9.21 | 4.59 | 9.07 |
| CD4i | E51 | 35.68 | 40.97 | 29.41 | 42.25 | 37.35 | 30.27 | 41.46 | 38.02 | 35.65 | 39.25 | 40.11 | 43.92 |
| C1-C4 | EH21 | 90.33 | 85.05 | 82.29 | 88.87 | 90.09 | 84.68 | 89.87 | 92.32 | 82.05 | 92.97 | 81.98 | 89.12 |

| Epitope | mAb | TV1 gp120 | | | | | | SF162 gp120 | | | | | |
|---|---|---|---|---|---|---|---|---|---|---|---|---|---|
| | | 37 | 38 | 39 | 40 | 41 | 42 | 43 | 44 | 45 | 46 | 47 | 48 |
| CD4bs | A32 | 83.98 | 71.29 | 77.50 | Serum Exhausted | 91.75 | 70.45 | 82.30 | 75.10 | 86.30 | 66.01 | 77.84 | 84.13 |
| V3 | 2557 | 29.38 | 14.32 | 16.05 | | 42.94 | 13.48 | 75.00 | 85.39 | 87.45 | 43.23 | 32.04 | 78.35 |
| CD4i | E51 | 53.34 | 44.03 | 41.10 | | 73.31 | 26.72 | 46.14 | 40.27 | 18.78 | 26.68 | 17.70 | 21.04 |
| C1-C4 | EH21 | 83.63 | 89.39 | 86.10 | | 87.85 | 78.27 | 78.02 | 103.62 | 80.03 | 112.23 | 82.49 | 74.98 |

| Epitope | mAb | TV1 gp140 | | | | | | SF162 gp140 | | | | | |
|---|---|---|---|---|---|---|---|---|---|---|---|---|---|
| | | 49 | 50 | 51 | 52 | 53 | 54 | 55 | 56 | 57 | 58 | 59 | 60 |
| CD4bs | A32 | 64.98 | 58.93 | 55.98 | 49.34 | 58.17 | 52.23 | 73.36 | 83.24 | 69.92 | 89.82 | 94.12 | 91.54 |
| V3 | 2557 | 6.05 | 7.75 | 10.30 | 5.38 | 9.94 | 9.35 | 30.04 | 63.65 | 30.58 | 61.73 | 56.84 | 25.29 |
| CD4i | E51 | 15.79 | 10.72 | 13.30 | 5.48 | 8.80 | 9.92 | 7.15 | 6.14 | 14.09 | 15.86 | 13.50 | 6.13 |
| C1-C4 | EH21 | 79.77 | 81.26 | 79.01 | 49.01 | 63.73 | 71.79 | 86.22 | 83.61 | 102.24 | 87.68 | 94.01 | 90.65 |

Figure 23

| Epitope | mAb | Du156.12 gp120 | | | | | | Du422.1 gp120 | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| CD4bs | A32 | 82.67 | 91.62 | 74.22 | 85.07 | 83.09 | 96.94 | 70.14 | 79.08 | 70.49 | 68.70 | 83.32 | 69.66 |
| V3 | 2557 | 4.99 | 15.28 | 8.35 | 7.65 | 3.55 | 3.52 | 3.54 | 8.02 | 4.63 | 4.07 | 10.52 | 7.41 |
| CD4i | E51 | 43.15 | 56.48 | 28.10 | 56.70 | 36.95 | 30.66 | 21.60 | 33.99 | 32.99 | 35.49 | 44.68 | 31.18 |
| C1-C4 | EH21 | 83.61 | 65.26 | 102.29 | 94.62 | 81.48 | 76.87 | 108.82 | 95.84 | 76.90 | 81.54 | 106.28 | 76.35 |

| Epitope | mAb | ZM249M.PL1 gp120 | | | | | | EF203960 gp120 | | | | | |
|---|---|---|---|---|---|---|---|---|---|---|---|---|---|
| | | 13 | 14 | 15 | 16 | 17 | 18 | 19 | 20 | 21 | 22 | 23 | 24 |
| CD4bs | A32 | 63.40 | 66.71 | 68.14 | 66.31 | 73.31 | 63.72 | 80.16 | 76.50 | 67.54 | 67.00 | 69.40 | 81.07 |
| V3 | 2557 | 4.11 | 6.54 | 4.54 | 5.71 | 10.16 | 5.59 | 7.15 | 10.82 | 8.78 | 6.05 | 4.90 | 6.15 |
| CD4i | E51 | 31.17 | 17.24 | 12.03 | 11.41 | 25.31 | 20.53 | 26.57 | 31.31 | 24.58 | 20.46 | 25.15 | 37.45 |
| C1-C4 | EH21 | 77.53 | 77.57 | 83.21 | 82.25 | 76.10 | 53.10 | 77.24 | 86.60 | 66.58 | 85.26 | 79.11 | 88.50 |

| Epitope | mAb | EF203963 gp120 | | | | | | EF203983 gp120 | | | | | |
|---|---|---|---|---|---|---|---|---|---|---|---|---|---|
| | | 25 | 26 | 27 | 28 | 29 | 30 | 31 | 32 | 33 | 34 | 35 | 36 |
| CD4bs | A32 | 84.86 | 83.35 | 71.69 | 83.08 | 72.71 | 82.72 | 78.38 | 80.32 | 74.01 | 78.35 | 72.04 | 83.51 |
| V3 | 2557 | 6.79 | 10.12 | 5.85 | 9.50 | 5.35 | 5.86 | 8.14 | 5.13 | 4.02 | 6.47 | 3.94 | 10.68 |
| CD4i | E51 | 38.78 | 32.71 | 23.68 | 35.33 | 34.12 | 31.33 | 34.79 | 33.91 | 35.68 | 27.16 | 30.32 | 38.70 |
| C1-C4 | EH21 | 95.54 | 90.11 | 95.07 | 85.60 | 86.50 | 84.39 | 106.63 | 81.80 | 77.88 | 88.04 | 80.13 | 81.40 |

| Epitope | mAb | TV1 gp120 | | | | | | SF162 gp120 | | | | | |
|---|---|---|---|---|---|---|---|---|---|---|---|---|---|
| | | 37 | 38 | 39 | 40 | 41 | 42 | 43 | 44 | 45 | 46 | 47 | 48 |
| CD4bs | A32 | 74.85 | 68.30 | 69.58 | 58.14 | 84.52 | 63.68 | 63.75 | 68.76 | 90.44 | 62.16 | 69.55 | 93.05 |
| V3 | 2557 | 33.02 | 10.85 | 13.84 | 14.66 | 29.04 | 9.55 | 71.77 | 90.44 | 91.94 | 28.12 | 23.13 | 87.30 |
| CD4i | E51 | 45.64 | 31.28 | 31.37 | 15.58 | 71.35 | 22.38 | 19.90 | 36.84 | 16.57 | 13.48 | 15.83 | 32.33 |
| C1-C4 | EH21 | 83.63 | 71.28 | 107.68 | 69.82 | 87.31 | 72.25 | 88.61 | 107.72 | 88.80 | 113.41 | 88.24 | 83.42 |

| Epitope | mAb | TV1 gp140 | | | | | | SF162 gp140 | | | | | |
|---|---|---|---|---|---|---|---|---|---|---|---|---|---|
| | | 49 | 50 | 51 | 52 | 53 | 54 | 55 | 56 | 57 | 58 | 59 | 60 |
| CD4bs | A32 | 61.00 | 46.03 | 61.42 | 47.94 | 41.35 | 40.77 | 39.13 | 64.18 | 67.25 | 44.57 | 91.02 | 84.35 |
| V3 | 2557 | 3.95 | 2.93 | 8.95 | 5.87 | 7.92 | 8.32 | 7.36 | 60.24 | 32.23 | 10.99 | 65.63 | 21.05 |
| CD4i | E51 | 11.02 | 3.97 | 11.47 | 5.61 | 4.91 | 2.93 | 3.21 | 4.32 | 13.25 | 2.59 | 18.54 | 5.05 |
| C1-C4 | EH21 | 81.64 | 73.15 | 65.56 | 50.12 | 50.23 | 58.55 | 56.67 | 82.39 | 103.24 | 63.25 | 97.18 | 84.31 |

SEQUENCE LISTING

```
<160> NUMBER OF SEQ ID NOS: 23

<210> SEQ ID NO 1
<211> LENGTH: 1419
<212> TYPE: DNA
<213> ORGANISM: Human immunodeficiency virus

<400> SEQUENCE: 1

gtagaaaaat tgtgggtcac agtctattat ggggtacctg tgtggaaaga agcaaccacc      60

actctatttt gtgcatcaga tgctaaagcc tatgacacag aggtacataa tgtctgggcc     120

acacatgcct gtgtacccac agaccctaac ccacaagaaa tagtattgga aaatgtgaca     180

gaaaatttta acatgtggaa aaataacatg gtagaacaga tgcatgagga tataatcagt     240

ttatgggatc aaagtctaaa gccatgtgta aagttaaccc cactctgtgt tactctacat     300

tgcactaatt tgaagaatgc tactaatacc aagagtagta attggaaaga gatggacaga     360

ggagaaataa aaaattgctc tttcaaggtc accacaagca taagaaataa gatgcagaaa     420

gaatatgcac ttttttataa acttgatgta gtaccaatag ataatgataa tacaagctat     480

aaattgataa attgtaacac ctcagtcatt acacaggcct gtccaaaggt atcctttgaa     540

ccaattccca tacattattg tgccccggct ggttttgcga ttctaaagtg taatgataag     600

aagttcaatg gatcaggacc atgtacaaat gtcagcacag tacaatgtac acatggaatt     660

aggccagtag tgtcaactca attgctgtta aatggcagtc tagcagaaga aggggtagta     720

attagatctg aaaatttcac agacaatgct aaaactataa tagtacagct gaaggaatct     780

gtagaaatta attgtacaag acctaacaat aatacaagaa aaagtataac tataggaccg     840

gggagagcat tttatgcaac aggagacata ataggagata taagacaagc acattgtaac     900

attagtggag aaaaatggaa taacacttta aaacagatag ttacaaaatt acaagcacaa     960

tttgggaata aaacaatagt ctttaagcaa tcctcaggag gggacccaga aattgtaatg    1020

cacagtttta attgtggagg ggaatttttc tactgtaatt caacacagct ttttaatagt    1080

acttggaata atactatagg gccaaataac actaatggaa ctatcacact cccatgcaga    1140

ataaaacaaa ttataaacag gtggcaggaa gtaggaaaag caatgtatgc ccctcccatc    1200

agaggacaaa ttagatgctc atcaaatatt acaggactgc tattaacaag agatggtggt    1260

aaagagatca gtaacaccac cgagatcttc agacctggag gtggagatat gagggacaat    1320

tggagaagtg aattatataa atataaagta gtaaaaattg agccattagg agtagcaccc    1380

accaaggcaa agagaagagt ggtgcagaga gaaaaaaga                           1419

<210> SEQ ID NO 2
<211> LENGTH: 1932
```

<212> TYPE: DNA
<213> ORGANISM: Human immunodeficiency virus

<400> SEQUENCE: 2
gtagaaaaat tgtgggtcac agtctattat ggggtacctg tgtggaaaga agcaaccacc 60
actctatttt gtgcatcaga tgctaaagcc tatgacacag aggtacataa tgtctgggcc 120
acacatgcct gtgtacccac agaccctaac ccacaagaaa tagtattgga aaatgtgaca 180
gaaaatttta acatgtggaa aaataacatg gtagaacaga tgcatgagga tataatcagt 240
ttatgggatc aaagtctaaa gccatgtgta aagttaaccc cactctgtgt tactctacat 300
tgcactaatt tgaagaatgc tactaatacc aagagtagta attggaaaga gatggacaga 360
ggagaaataa aaaattgctc tttcaaggtc accacaagca taagaaataa gatgcagaaa 420
gaatatgcac ttttttataa acttgatgta gtaccaatag ataatgataa tacaagctat 480
aaattgataa attgtaacac ctcagtcatt acacaggcct gtccaaaggt atcctttgaa 540
ccaattccca tacattattg tgccccggct ggttttgcga ttctaaagtg taatgataag 600
aagttcaatg gatcaggacc atgtacaaat gtcagcacag tacaatgtac acatggaatt 660
aggccagtag tgtcaactca attgctgtta aatggcagtc tagcagaaga aggggtagta 720
attagatctg aaaatttcac agacaatgct aaaactataa tagtacagct gaaggaatct 780
gtagaaatta attgtacaag acctaacaat aatacaagaa aaagtataac tataggaccg 840
gggagagcat tttatgcaac aggagacata ataggagata taagacaagc acattgtaac 900
attagtggag aaaaatggaa taacacttta aaacagatag ttacaaaatt acaagcacaa 960
tttgggaata aaacaatagt ctttaagcaa tcctcaggag gggacccaga aattgtaatg 1020
cacagtttta attgtggagg ggaatttttc tactgtaatt caacacagct ttttaatagt 1080
acttggaata atactatagg gccaaataac actaatggaa ctatcacact cccatgcaga 1140
ataaaacaaa ttataaacag gtggcaggaa gtaggaaaag caatgtatgc ccctcccatc 1200
agaggacaaa ttagatgctc atcaaatatt acaggactgc tattaacaag agatggtggt 1260
aaagagatca gtaacaccac cgagatcttc agacctggag gtggagatat gagggacaat 1320
tggagaagtg aattatataa atataaagta gtaaaaattg agccattagg agtagcaccc 1380
accaaggcaa agagaagagt ggtgcagaga gaaaaaagag cagtgacgct aggagctatg 1440
ttccttgggt tcttgggagc agcaggaagc actatgggcg cacggtcact gacgctgacg 1500
gtacaggcca gacaattatt gtctggtata gtgcaacagc agaacaattt gctgagagct 1560
attgaggcgc aacagcatct gttgcaactc acagtctggg gcatcaagca gctccaggca 1620
agagtcctgg ctgtggaaag atacctaaag gatcaacagc tcctagggat ttggggttgc 1680
tctggaaaac tcatttgcac cactgctgtg ccttggaatg ctagttggag taataaatct 1740
ctggatcaga tttggaataa catgacctgg atggagtggg agagagaaat tgacaattac 1800
acaaacttaa tatacacctt aattgaagaa tcgcagaacc aacaagaaaa gaatgaacaa 1860
gaattattag aattggataa gtgggcaagt ttgtggaatt ggtttgacat atcaaaatgg 1920
ctgtggtata ta 1932

<210> SEQ ID NO 3
<211> LENGTH: 2457
<212> TYPE: DNA
<213> ORGANISM: Human immunodeficiency virus -continued

<400> SEQUENCE: 3

```
gtagaaaaat tgtgggtcac agtctattat ggggtacctg tgtggaaaga agcaaccacc     60
actctatttt gtgcatcaga tgctaaagcc tatgacacag aggtacataa tgtctgggcc    120
acacatgcct gtgtacccac agaccctaac ccacaagaaa tagtattgga aaatgtgaca    180
gaaaatttta acatgtggaa aaataacatg gtagaacaga tgcatgagga tataatcagt    240
ttatgggatc aaagtctaaa gccatgtgta aagttaaccc cactctgtgt tactctacat    300
tgcactaatt tgaagaatgc tactaatacc aagagtagta attggaaaga gatggacaga    360
ggagaaataa aaaattgctc tttcaaggtc accacaagca taagaaataa gatgcagaaa    420
gaatatgcac tttttataa acttgatgta gtaccaatag ataatgataa tacaagctat     480
aaattgataa attgtaacac ctcagtcatt acacaggcct gtccaaaggt atcctttgaa    540
ccaattccca tacattattg tgccccggct ggttttgcga ttctaaagtg taatgataag    600
aagttcaatg gatcaggacc atgtacaaat gtcagcacag tacaatgtac acatggaatt    660
aggccagtag tgtcaactca attgctgtta aatggcagtc tagcagaaga aggggtagta    720
attagatctg aaaatttcac agacaatgct aaaactataa tagtacagct gaaggaatct    780
gtagaaatta attgtacaag acctaacaat aatacaagaa aaagtataac tataggaccg    840
gggagagcat tttatgcaac aggagacata ataggagata taagacaagc acattgtaac    900
attagtggag aaaaatggaa taacacttta aaacagatag ttacaaaatt acaagcacaa    960
tttgggaata aaacaatagt ctttaagcaa tcctcaggag gggacccaga aattgtaatg   1020
cacagtttta attgtggagg ggaatttttc tactgtaatt caacacagct ttttaatagt   1080
acttggaata atactatagg gccaaataac actaatggaa ctatcacact cccatgcaga   1140
ataaaacaaa ttataaacag gtggcaggaa gtaggaaaag caatgtatgc ccctcccatc   1200
agaggacaaa ttagatgctc atcaaatatt acaggactgc tattaacaag agatggtggt   1260
aaagagatca gtaacaccac cgagatcttc agacctggag gtggagatat gagggacaat   1320
tggagaagtg aattatataa atataaagta gtaaaaattg agccattagg agtagcaccc   1380
accaaggcaa agagaagagt ggtgcagaga gaaaaaagag cagtgacgct aggagctatg   1440
ttccttgggt tcttgggagc agcaggaagc actatgggcg cacggtcact gacgctgacg   1500
gtacaggcca gacaattatt gtctggtata gtgcaacagc agaacaattt gctgagagct   1560
attgaggcgc aacagcatct gttgcaactc acagtctggg gcatcaagca gctccaggca   1620
agagtcctgg ctgtggaaag atacctaaag gatcaacagc tcctagggat ttggggttgc   1680
tctggaaaac tcatttgcac cactgctgtg ccttggaatg ctagttggag taataaatct   1740
ctggatcaga tttggaataa catgacctgg atggagtggg agagagaaat tgacaattac   1800
acaaacttaa tatacacctt aattgaagaa tcgcagaacc aacaagaaaa gaatgaacaa   1860
gaattattag aattggataa gtgggcaagt ttgtggaatt ggtttgacat atcaaaatgg   1920
ctgtggtata taaaaatatt cataatgata gtaggaggtt tagtaggttt aaggatagtt   1980
tttactgtgc tttctatagt gaatagagtt aggcagggat actcaccatt atcatttcag   2040
acccgcttcc cagccccaag gggacccgac aggcccgaag gaatcgaaga agaaggtgga   2100
gagagagaca gagacagatc cagtccatta gtgcatggat tattagcact catctgggac   2160
gatctacgga gcctgtgcct cttcagctac caccgcttga gagacttaat cttgattgca   2220
gcgaggattg tggaacttct gggacgcagg gggtgggaag ccctcaagta ttgggggaat   2280
```

-continued ctcctgcagt attggattca ggaactaaag aatagtgctg ttagtttgtt tgatgccata 2340
gctatagcag tagctgaggg gacagatagg attatagaag tagcacaaag aattggtaga 2400
gcttttctcc acatacctag aagaataaga cagggctttg aaagggcttt gctataa 2457

<210> SEQ ID NO 4
<211> LENGTH: 1453
<212> TYPE: DNA
<213> ORGANISM: Artificial Sequence
<220> FEATURE:
<223> OTHER INFORMATION: gp120.modSF162

<400> SEQUENCE: 4
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360
acccccctgt gcgtgaccct gcactgcacc aacctgaaga acgccaccaa caccaagagc 420
agcaactgga aggagatgga ccgcggcgag atcaagaact gcagcttcaa ggtgaccacc 480
agcatccgca acaagatgca gaaggagtac gccctgttct acaagctgga cgtggtgccc 540
atcgacaacg acaacaccag ctacaagctg atcaactgca acaccagcgt gatcacccag 600
gcctgcccca aggtgagctt cgagcccatc cccatccact actgcgcccc cgccggcttc 660
gccatcctga agtgcaacga caagaagttc aacggcagcg gcccctgcac caacgtgagc 720
accgtgcagt gcacccacgg catccgcccc gtggtgagca cccagctgct gctgaacggc 780
agcctggccg aggagggcgt ggtgatccgc agcgagaact tcaccgacaa cgccaagacc 840
atcatcgtgc agctgaagga gagcgtggag atcaactgca cccgccccaa caacaacacc 900
cgcaagagca tcaccatcgg ccccggccgc gccttctacg ccaccggcga catcatcggc 960
gacatccgcc aggcccactg caacatcagc ggcgagaagt ggaacaacac cctgaagcag 1020
atcgtgacca agctgcaggc ccagttcggc aacaagacca tcgtgttcaa gcagagcagc 1080
ggcggcgacc ccgagatcgt gatgcacagc ttcaactgcg gcggcgagtt cttctactgc 1140
aacagcaccc agctgttcaa cagcacctgg aacaacacca tcggccccaa caacaccaac 1200
ggcaccatca ccctgccctg ccgcatcaag cagatcatca accgctggca ggaggtgggc 1260
aaggccatgt acgccccccc catccgcggc cagatccgct gcagcagcaa catcaccggc 1320
ctgctgctga cccgcgacgg cggcaaggag atcagcaaca ccaccgagat cttccgcccc 1380
ggcggcggcg acatgcgcga caactggcgc agcgagctgt acaagtacaa ggtggtgaag 1440
atcgagcccc tgg 1453

<210> SEQ ID NO 5
<211> LENGTH: 1387
<212> TYPE: DNA
<213> ORGANISM: Artificial Sequence
<220> FEATURE:
<223> OTHER INFORMATION: gp120.modSF162.delV2

<400> SEQUENCE: 5
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120

```
cccgtgtgga aggaggccac caccaccctg ttctgcgcca gcgacgccaa ggcctacgac    180
accgaggtgc acaacgtgtg ggccacccac gcctgcgtgc ccaccgaccc caacccccag    240
gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360
acccccctgt gcgtgaccct gcactgcacc aacctgaaga acgccaccaa caccaagagc    420
agcaactgga aggagatgga ccgcggcgag atcaagaact gcagcttcaa ggtgggcgcc    480
ggcaagctga tcaactgcaa caccagcgtg atcacccagg cctgccccaa ggtgagcttc    540
gagcccatcc ccatccacta ctgcgccccc gccggcttcg ccatcctgaa gtgcaacgac    600
aagaagttca acggcagcgg cccctgcacc aacgtgagca ccgtgcagtg cacccacggc    660
atccgccccg tggtgagcac ccagctgctg ctgaacggca gcctggccga ggagggcgtg    720
gtgatccgca gcgagaactt caccgacaac gccaagacca tcatcgtgca gctgaaggag    780
agcgtggaga tcaactgcac ccgccccaac aacaacaccc gcaagagcat caccatcggc    840
cccggccgcg ccttctacgc caccggcgac atcatcggcg acatccgcca ggcccactgc    900
aacatcagcg gcgagaagtg gaacaacacc ctgaagcaga tcgtgaccaa gctgcaggcc    960
cagttcggca acaagaccat cgtgttcaag cagagcagcg gcggcgaccc cgagatcgtg   1020
atgcacagct tcaactgcgg cggcgagttc ttctactgca acagcaccca gctgttcaac   1080
agcacctgga acaacaccat cggcccccaac aacaccaacg gcaccatcac cctgccctgc   1140
cgcatcaagc agatcatcaa ccgctggcag gaggtgggca aggccatgta cgcccccccc   1200
atccgcggcc agatccgctg cagcagcaac atcaccggcc tgctgctgac ccgcgacggc   1260
ggcaaggaga tcagcaacac caccgagatc ttccgccccg gcggcggcga catgcgcgac   1320
aactggcgca gcgagctgta caagtacaag gtggtgaaga tcgagcccct gggcgtggcc   1380
cccacca                                                             1387
```

```
<210> SEQ ID NO 6
<211> LENGTH: 1323
<212> TYPE: DNA
<213> ORGANISM: Artificial Sequence
<220> FEATURE:
<223> OTHER INFORMATION: gp120.modSF162.delV1V2

<400> SEQUENCE: 6
```

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg ggccacccac gcctgcgtgc ccaccgaccc caacccccag    240
gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360
acccccctgt gcgtgggcgc cggcaactgc cagaccagcg tgatcaccca ggcctgcccc    420
aaggtgagct tcgagcccat ccccatccac tactgcgccc ccgccggctt cgccatcctg    480
aagtgcaacg acaagaagtt caacggcagc ggcccctgca ccaacgtgag caccgtgcag    540
tgcacccacg gcatccgccc cgtggtgagc acccagctgc tgctgaacgg cagcctggcc    600
gaggagggcg tggtgatccg cagcgagaac ttcaccgaca acgccaagac catcatcgtg    660
cagctgaagg agagcgtgga gatcaactgc acccgcccca acaacaacac ccgcaagagc    720
```

-continued

```
atcaccatcg gccccggccg cgccttctac gccaccggcg acatcatcgg cgacatccgc    780

caggcccact gcaacatcag cggcgagaag tggaacaaca ccctgaagca gatcgtgacc    840

aagctgcagg cccagttcgg caacaagacc atcgtgttca agcagagcag cggcggcgac    900

cccgagatcg tgatgcacag cttcaactgc ggcggcgagt tcttctactg caacagcacc    960

cagctgttca acagcacctg gaacaacacc atcggcccca acaacaccaa cggcaccatc   1020

accctgccct gccgcatcaa gcagatcatc aaccgctggc aggaggtggg caaggccatg   1080

tacgcccccc ccatccgcgg ccagatccgc tgcagcagca acatcaccgg cctgctgctg   1140

acccgcgacg gcggcaagga gatcagcaac accaccgaga tcttccgccc cggcggcggc   1200

gacatgcgcg acaactggcg cagcgagctg tacaagtaca aggtggtgaa gatcgagccc   1260

ctgggcgtgg cccccaccaa ggccaagcgc cgcgtggtgc agcgcgagaa gcgctaactc   1320

gag                                                                 1323
```

<210> SEQ ID NO 7
<211> LENGTH: 2025
<212> TYPE: DNA
<213> ORGANISM: Artificial Sequence
<220> FEATURE:
<223> OTHER INFORMATION: gp140.modSF162

<400> SEQUENCE: 7

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgaagctg    360

accccccctgt gcgtgaccct gcactgcacc aacctgaaga acgccaccaa caccaagagc    420

agcaactgga aggagatgga ccgcggcgag atcaagaact gcagcttcaa ggtgaccacc    480

agcatccgca acaagatgca gaaggagtac gccctgttct acaagctgga cgtggtgccc    540

atcgacaacg acaacaccag ctacaagctg atcaactgca acaccagcgt gatcacccag    600

gcctgcccca aggtgagctt cgagcccatc cccatccact actgcgcccc cgccggcttc    660

gccatcctga agtgcaacga caagaagttc aacggcagcg gcccctgcac caacgtgagc    720

accgtgcagt gcacccacgg catccgcccc gtggtgagca cccagctgct gctgaacggc    780

agcctggccg aggagggcgt ggtgatccgc agcgagaact tcaccgacaa cgccaagacc    840

atcatcgtgc agctgaagga gagcgtggag atcaactgca cccgccccaa caacaacacc    900

cgcaagagca tcaccatcgg ccccggccgc gccttctacg ccaccggcga catcatcggc    960

gacatccgcc aggcccactg caacatcagc ggcgagaagt ggaacaacac cctgaagcag   1020

atcgtgacca agctgcaggc ccagttcggc aacaagacca tcgtgttcaa gcagagcagc   1080

ggcggcgacc ccgagatcgt gatgcacagc ttcaactgcg gcggcgagtt cttctactgc   1140

aacagcaccc agctgttcaa cagcacctgg aacaacacca tcggccccaa caacaccaac   1200

ggcaccatca ccctgccctg ccgcatcaag cagatcatca accgctggca ggaggtgggc   1260

aaggccatgt acgccccccc catccgcggc cagatccgct gcagcagcaa catcaccggc   1320

ctgctgctga cccgcgacgg cggcaaggag atcagcaaca ccaccgagat cttccgcccc   1380

ggcggcggcg acatgcgcga caactggcgc agcgagctgt acaagtacaa ggtggtgaag   1440
```

```
atcgagcccc tgggcgtggc ccccaccaag gccaagcgcc gcgtggtgca gcgcgagaag   1500

cgcgccgtga ccctgggcgc catgttcctg ggcttcctgg gcgccgccgg cagcaccatg   1560

ggcgcccgca gcctgaccct gaccgtgcag gcccgccagc tgctgagcgg catcgtgcag   1620

cagcagaaca acctgctgcg cgccatcgag gcccagcagc acctgctgca gctgaccgtg   1680

tggggcatca agcagctgca ggcccgcgtg ctggccgtgg agcgctacct gaaggaccag   1740

cagctgctgg gcatctgggg ctgcagcggc aagctgatct gcaccaccgc cgtgccctgg   1800

aacgccagct ggagcaacaa gagcctggac cagatctgga acaacatgac ctggatggag   1860

tgggagcgcg agatcgacaa ctacaccaac ctgatctaca ccctgatcga ggagagccag   1920

aaccagcagg agaagaacga gcaggagctg ctggagctgg acaagtgggc cagcctgtgg   1980

aactggttcg acatcagcaa gtggctgtgg tacatctaac tcgag                   2025
```

<210> SEQ ID NO 8
<211> LENGTH: 1944
<212> TYPE: DNA
<213> ORGANISM: Artificial Sequence
<220> FEATURE:
<223> OTHER INFORMATION: gp140.modSF162.delV2

<400> SEQUENCE: 8

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgaagctg    360

acccccctgt gcgtgaccct gcactgcacc aacctgaaga acgccaccaa caccaagagc    420

agcaactgga aggagatgga ccgcggcgag atcaagaact gcagcttcaa ggtgggcgcc    480

ggcaagctga tcaactgcaa caccagcgtg atcacccagg cctgccccaa ggtgagcttc    540

gagcccatcc ccatccacta ctgcgccccc gccggcttcg ccatcctgaa gtgcaacgac    600

aagaagttca acggcagcgg cccctgcacc aacgtgagca ccgtgcagtg cacccacggc    660

atccgccccg tggtgagcac ccagctgctg ctgaacggca gcctggccga ggagggcgtg    720

gtgatccgca gcgagaactt caccgacaac gccaagacca tcatcgtgca gctgaaggag    780

agcgtggaga tcaactgcac ccgccccaac aacaacaccc gcaagagcat caccatcggc    840

cccggccgcg ccttctacgc caccggcgac atcatcggcg acatccgcca ggcccactgc    900

aacatcagcg gcgagaagtg gaacaacacc ctgaagcaga tcgtgaccaa gctgcaggcc    960

cagttcggca acaagaccat cgtgttcaag cagagcagcg gcggcgaccc cgagatcgtg   1020

atgcacagct tcaactgcgg cggcgagttc ttctactgca acagcaccca gctgttcaac   1080

agcacctgga acaacaccat cggccccaac aacaccaacg gcaccatcac cctgccctgc   1140

cgcatcaagc agatcatcaa ccgctggcag gaggtgggca aggccatgta cgcccccccc   1200

atccgcggcc agatccgctg cagcagcaac atcaccggcc tgctgctgac ccgcgacggc   1260

ggcaaggaga tcagcaacac caccgagatc ttccgccccg gcggcggcga catgcgcgac   1320

aactggcgca gcgagctgta caagtacaag gtggtgaaga tcgagcccct gggcgtggcc   1380

cccaccaagg ccaagcgccg cgtggtgcag cgcgagaagc gcgccgtgac cctgggcgcc   1440
```

atgttcctgg gcttcctggg cgccgccggc agcaccatgg gcgcccgcag cctgaccctg 1500
accgtgcagg cccgccagct gctgagcggc atcgtgcagc agcagaacaa cctgctgcgc 1560
gccatcgagg cccagcagca cctgctgcag ctgaccgtgt ggggcatcaa gcagctgcag 1620
gcccgcgtgc tggccgtgga gcgctacctg aaggaccagc agctgctggg catctggggc 1680
tgcagcggca agctgatctg caccaccgcc gtgccctgga acgccagctg gagcaacaag 1740
agcctggacc agatctggaa caacatgacc tggatggagt gggagcgcga gatcgacaac 1800
tacaccaacc tgatctacac cctgatcgag gagagccaga accagcagga gaagaacgag 1860
caggagctgc tggagctgga caagtgggcc agcctgtgga actggttcga catcagcaag 1920
tggctgtggt acatctaact cgag 1944

<210> SEQ ID NO 9
<211> LENGTH: 1944
<212> TYPE: DNA
<213> ORGANISM: Artificial Sequence
<220> FEATURE:
<223> OTHER INFORMATION: gp140.modSF162.delV1/V2

<400> SEQUENCE: 9
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360
acccccctgt gcgtgaccct gcactgcacc aacctgaaga acgccaccaa caccaagagc 420
agcaactgga aggagatgga ccgcggcgag atcaagaact gcagcttcaa ggtgggcgcc 480
ggcaagctga tcaactgcaa caccagcgtg atcacccagg cctgccccaa ggtgagcttc 540
gagcccatcc ccatccacta ctgcgccccc gccggcttcg ccatcctgaa gtgcaacgac 600
aagaagttca acggcagcgg cccctgcacc aacgtgagca ccgtgcagtg cacccacggc 660
atccgccccg tggtgagcac ccagctgctg ctgaacggca gcctggccga ggagggcgtg 720
gtgatccgca gcgagaactt caccgacaac gccaagacca tcatcgtgca gctgaaggag 780
agcgtggaga tcaactgcac ccgccccaac aacaacaccc gcaagagcat caccatcggc 840
cccggccgcg ccttctacgc caccggcgac atcatcggcg acatccgcca ggcccactgc 900
aacatcagcg gcgagaagtg gaacaacacc ctgaagcaga tcgtgaccaa gctgcaggcc 960
cagttcggca acaagaccat cgtgttcaag cagagcagcg gcggcgaccc cgagatcgtg 1020
atgcacagct tcaactgcgg cggcgagttc ttctactgca acagcaccca gctgttcaac 1080
agcacctgga acaacaccat cggccccaac aacaccaacg gcaccatcac cctgccctgc 1140
cgcatcaagc agatcatcaa ccgctggcag gaggtgggca aggccatgta cgcccccccc 1200
atccgcggcc agatccgctg cagcagcaac atcaccggcc tgctgctgac ccgcgacggc 1260
ggcaaggaga tcagcaacac caccgagatc ttccgccccg gcggcggcga catgcgcgac 1320
aactggcgca gcgagctgta caagtacaag gtggtgaaga tcgagcccct gggcgtggcc 1380
cccaccaagg ccaagcgccg cgtggtgcag cgcgagaagc gcgccgtgac cctgggcgcc 1440
atgttcctgg gcttcctggg cgccgccggc agcaccatgg gcgcccgcag cctgaccctg 1500
accgtgcagg cccgccagct gctgagcggc atcgtgcagc agcagaacaa cctgctgcgc 1560
gccatcgagg cccagcagca cctgctgcag ctgaccgtgt ggggcatcaa gcagctgcag 1620
gcccgcgtgc tggccgtgga gcgctacctg aaggaccagc agctgctggg catctggggc 1680
tgcagcggca agctgatctg caccaccgcc gtgccctgga acgccagctg gagcaacaag 1740
agcctggacc agatctggaa caacatgacc tggatggagt gggagcgcga gatcgacaac 1800
tacaccaacc tgatctacac cctgatcgag gagagccaga accagcagga gaagaacgag 1860
caggagctgc tggagctgga caagtgggcc agcctgtgga actggttcga catcagcaag 1920
tggctgtggt acatctaact cgag 1944

<210> SEQ ID NO 10
<211> LENGTH: 2025
<212> TYPE: DNA
<213> ORGANISM: Artificial Sequence
<220> FEATURE:
<223> OTHER INFORMATION: gp140.mut.modSF162

<400> SEQUENCE: 10
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360
acccccctgt gcgtgaccct gcactgcacc aacctgaaga acgccaccaa caccaagagc 420
agcaactgga aggagatgga ccgcggcgag atcaagaact gcagcttcaa ggtgaccacc 480
agcatccgca acaagatgca gaaggagtac gccctgttct acaagctgga cgtggtgccc 540
atcgacaacg acaacaccag ctacaagctg atcaactgca acaccagcgt gatcacccag 600
gcctgcccca aggtgagctt cgagcccatc cccatccact actgcgcccc cgccggcttc 660
gccatcctga agtgcaacga caagaagttc aacggcagcg gcccctgcac caacgtgagc 720
accgtgcagt gcacccacgg catccgcccc gtggtgagca cccagctgct gctgaacggc 780
agcctggccg aggagggcgt ggtgatccgc agcgagaact tcaccgacaa cgccaagacc 840
atcatcgtgc agctgaagga gagcgtggag atcaactgca cccgccccaa caacaacacc 900
cgcaagagca tcaccatcgg ccccggccgc gccttctacg ccaccggcga catcatcggc 960
gacatccgcc aggcccactg caacatcagc ggcgagaagt ggaacaacac cctgaagcag 1020
atcgtgacca agctgcaggc ccagttcggc aacaagacca tcgtgttcaa gcagagcagc 1080
ggcggcgacc ccgagatcgt gatgcacagc ttcaactgcg gcggcgagtt cttctactgc 1140
aacagcaccc agctgttcaa cagcacctgg aacaacacca tcggccccaa caacaccaac 1200
ggcaccatca ccctgccctg ccgcatcaag cagatcatca accgctggca ggaggtgggc 1260
aaggccatgt acgccccccc catccgcggc cagatccgct gcagcagcaa catcaccggc 1320
ctgctgctga cccgcgacgg cggcaaggag atcagcaaca ccaccgagat cttccgcccc 1380
ggcggcggcg acatgcgcga caactggcgc agcgagctgt acaagtacaa ggtggtgaag 1440
atcgagcccc tgggcgtggc ccccaccaag gccaagcgcc gcgtggtgca gcgcgagaag 1500
agcgccgtga ccctgggcgc catgttcctg ggcttcctgg gcgccgccgg cagcaccatg 1560
ggcgcccgca gcctgaccct gaccgtgcag gcccgccagc tgctgagcgg catcgtgcag 1620

```
cagcagaaca acctgctgcg cgccatcgag gcccagcagc acctgctgca gctgaccgtg   1680

tggggcatca agcagctgca ggcccgcgtg ctggccgtgg agcgctacct gaaggaccag   1740

cagctgctgg gcatctgggg ctgcagcggc aagctgatct gcaccaccgc cgtgccctgg   1800

aacgccagct ggagcaacaa gagcctggac cagatctgga acaacatgac ctggatggag   1860

tgggagcgcg agatcgacaa ctacaccaac ctgatctaca ccctgatcga ggagagccag   1920

aaccagcagg agaagaacga gcaggagctg ctggagctgg acaagtgggc cagcctgtgg   1980

aactggttcg acatcagcaa gtggctgtgg tacatctaac tcgag                   2025
```

<210> SEQ ID NO 11
<211> LENGTH: 1944
<212> TYPE: DNA
<213> ORGANISM: Artificial Sequence
<220> FEATURE:
<223> OTHER INFORMATION: gp140.mut.modSF162.delV2

<400> SEQUENCE: 11

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgaagctg    360

acccccctgt gcgtgaccct gcactgcacc aacctgaaga acgccaccaa caccaagagc    420

agcaactgga aggagatgga ccgcggcgag atcaagaact gcagcttcaa ggtgggcgcc    480

ggcaagctga tcaactgcaa caccagcgtg atcacccagg cctgccccaa ggtgagcttc    540

gagcccatcc ccatccacta ctgcgccccc gccggcttcg ccatcctgaa gtgcaacgac    600

aagaagttca acggcagcgg cccctgcacc aacgtgagca ccgtgcagtg cacccacggc    660

atccgccccg tggtgagcac ccagctgctg ctgaacggca gcctggccga ggagggcgtg    720

gtgatccgca gcgagaactt caccgacaac gccaagacca tcatcgtgca gctgaaggag    780

agcgtggaga tcaactgcac ccgccccaac aacaacaccc gcaagagcat caccatcggc    840

cccggccgcg ccttctacgc caccggcgac atcatcggcg acatccgcca ggcccactgc    900

aacatcagcg gcgagaagtg gaacaacacc ctgaagcaga tcgtgaccaa gctgcaggcc    960

cagttcggca acaagaccat cgtgttcaag cagagcagcg gcggcgaccc cgagatcgtg   1020

atgcacagct tcaactgcgg cggcgagttc ttctactgca acagcaccca gctgttcaac   1080

agcacctgga acaacaccat cggccccaac aacaccaacg gcaccatcac cctgccctgc   1140

cgcatcaagc agatcatcaa ccgctggcag gaggtgggca aggccatgta cgcccccccc   1200

atccgcggcc agatccgctg cagcagcaac atcaccggcc tgctgctgac ccgcgacggc   1260

ggcaaggaga tcagcaacac caccgagatc ttccgccccg gcggcggcga catgcgcgac   1320

aactggcgca gcgagctgta caagtacaag gtggtgaaga tcgagcccct gggcgtggcc   1380

cccaccaagg ccaagcgccg cgtggtgcag cgcgagaaga gcgccgtgac cctgggcgcc   1440

atgttcctgg gcttcctggg cgccgccggc agcaccatgg gcgcccgcag cctgaccctg   1500

accgtgcagg cccgccagct gctgagcggc atcgtgcagc agcagaacaa cctgctgcgc   1560

gccatcgagg cccagcagca cctgctgcag ctgaccgtgt ggggcatcaa gcagctgcag   1620

gcccgcgtgc tggccgtgga gcgctacctg aaggaccagc agctgctggg catctggggc   1680
```

tgcagcggca agctgatctg caccaccgcc gtgccctgga acgccagctg gagcaacaag 1740
agcctggacc agatctggaa caacatgacc tggatggagt gggagcgcga gatcgacaac 1800
tacaccaacc tgatctacac cctgatcgag gagagccaga accagcagga gaagaacgag 1860
caggagctgc tggagctgga caagtgggcc agcctgtgga actggttcga catcagcaag 1920
tggctgtggt acatctaact cgag 1944

<210> SEQ ID NO 12
<211> LENGTH: 1836
<212> TYPE: DNA
<213> ORGANISM: Artificial Sequence
<220> FEATURE:
<223> OTHER INFORMATION: gp140.mut.modSF162.delV1/V2

<400> SEQUENCE: 12
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360
acccccctgt gcgtgggcgc cggcaactgc cagaccagcg tgatcaccca ggcctgcccc 420
aaggtgagct tcgagcccat ccccatccac tactgcgccc ccgccggctt cgccatcctg 480
aagtgcaacg acaagaagtt caacggcagc ggcccctgca ccaacgtgag caccgtgcag 540
tgcacccacg gcatccgccc cgtggtgagc acccagctgc tgctgaacgg cagcctggcc 600
gaggagggcg tggtgatccg cagcgagaac ttcaccgaca acgccaagac catcatcgtg 660
cagctgaagg agagcgtgga gatcaactgc acccgcccca acaacaacac ccgcaagagc 720
atcaccatcg gccccggccg cgccttctac gccaccggcg acatcatcgg cgacatccgc 780
caggcccact gcaacatcag cggcgagaag tggaacaaca ccctgaagca gatcgtgacc 840
aagctgcagg cccagttcgg caacaagacc atcgtgttca agcagagcag cggcggcgac 900
cccgagatcg tgatgcacag cttcaactgc ggcggcgagt tcttctactg caacagcacc 960
cagctgttca acagcacctg gaacaacacc atcggcccca acaacaccaa cggcaccatc 1020
accctgccct gccgcatcaa gcagatcatc aaccgctggc aggaggtggg caaggccatg 1080
tacgcccccc ccatccgcgg ccagatccgc tgcagcagca acatcaccgg cctgctgctg 1140
acccgcgacg gcggcaagga gatcagcaac accaccgaga tcttccgccc cggcggcggc 1200
gacatgcgcg acaactggcg cagcgagctg tacaagtaca aggtggtgaa gatcgagccc 1260
ctgggcgtgg cccccaccaa ggccaagcgc cgcgtggtgc agcgcgagaa gagcgccgtg 1320
accctgggcg ccatgttcct gggcttcctg ggcgccgccg gcagcaccat gggcgcccgc 1380
agcctgaccc tgaccgtgca ggcccgccag ctgctgagcg gcatcgtgca gcagcagaac 1440
aacctgctgc gcgccatcga ggcccagcag cacctgctgc agctgaccgt gtggggcatc 1500
aagcagctgc aggcccgcgt gctggccgtg gagcgctacc tgaaggacca gcagctgctg 1560
ggcatctggg gctgcagcgg caagctgatc tgcaccaccg ccgtgccctg gaacgccagc 1620
tggagcaaca agagcctgga ccagatctgg aacaacatga cctggatgga gtgggagcgc 1680
gagatcgaca actacaccaa cctgatctac accctgatcg aggagagcca gaaccagcag 1740

-continued gagaagaacg agcaggagct gctggagctg gacaagtggg ccagcctgtg gaactggttc 1800
gacatcagca agtggctgtg gtacatctaa ctcgag 1836

<210> SEQ ID NO 13
<211> LENGTH: 2025
<212> TYPE: DNA
<213> ORGANISM: Artificial Sequence
<220> FEATURE:
<223> OTHER INFORMATION: gp140.mut7.modSF162

<400> SEQUENCE: 13
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360
acccccctgt gcgtgaccct gcactgcacc aacctgaaga acgccaccaa caccaagagc 420
agcaactgga aggagatgga ccgcggcgag atcaagaact gcagcttcaa ggtgaccacc 480
agcatccgca acaagatgca gaaggagtac gccctgttct acaagctgga cgtggtgccc 540
atcgacaacg acaacaccag ctacaagctg atcaactgca acaccagcgt gatcacccag 600
gcctgcccca aggtgagctt cgagcccatc cccatccact actgcgcccc cgccggcttc 660
gccatcctga agtgcaacga caagaagttc aacggcagcg gcccctgcac caacgtgagc 720
accgtgcagt gcacccacgg catccgcccc gtggtgagca cccagctgct gctgaacggc 780
agcctggccg aggagggcgt ggtgatccgc agcgagaact tcaccgacaa cgccaagacc 840
atcatcgtgc agctgaagga gagcgtggag atcaactgca cccgccccaa caacaacacc 900
cgcaagagca tcaccatcgg ccccggccgc gccttctacg ccaccggcga catcatcggc 960
gacatccgcc aggcccactg caacatcagc ggcgagaagt ggaacaacac cctgaagcag 1020
atcgtgacca agctgcaggc ccagttcggc aacaagacca tcgtgttcaa gcagagcagc 1080
ggcggcgacc ccgagatcgt gatgcacagc ttcaactgcg gcggcgagtt cttctactgc 1140
aacagcaccc agctgttcaa cagcacctgg aacaacacca tcggccccaa caacaccaac 1200
ggcaccatca ccctgccctg ccgcatcaag cagatcatca accgctggca ggaggtgggc 1260
aaggccatgt acgccccccc catccgcggc cagatccgct gcagcagcaa catcaccggc 1320
ctgctgctga cccgcgacgg cggcaaggag atcagcaaca ccaccgagat cttccgcccc 1380
ggcggcggcg acatgcgcga caactggcgc agcgagctgt acaagtacaa ggtggtgaag 1440
atcgagcccc tgggcgtggc ccccaccaag gccatcagca gcgtggtgca gagcgagaag 1500
agcgccgtga ccctgggcgc catgttcctg ggcttcctgg gcgccgccgg cagcaccatg 1560
ggcgcccgca gcctgaccct gaccgtgcag gcccgccagc tgctgagcgg catcgtgcag 1620
cagcagaaca acctgctgcg cgccatcgag gcccagcagc acctgctgca gctgaccgtg 1680
tggggcatca agcagctgca ggcccgcgtg ctggccgtgg agcgctacct gaaggaccag 1740
cagctgctgg gcatctgggg ctgcagcggc aagctgatct gcaccaccgc cgtgccctgg 1800
aacgccagct ggagcaacaa gagcctggac cagatctgga acaacatgac ctggatggag 1860
tgggagcgcg agatcgacaa ctacaccaac ctgatctaca ccctgatcga ggagagccag 1920
aaccagcagg agaagaacga gcaggagctg ctggagctgg acaagtgggc cagcctgtgg 1980
aactggttcg acatcagcaa gtggctgtgg tacatctaac tcgag 2025

<210> SEQ ID NO 14
<211> LENGTH: 1944
<212> TYPE: DNA
<213> ORGANISM: Artificial Sequence
<220> FEATURE:
<223> OTHER INFORMATION: gp140.mut7.modSF162.delV2

<400> SEQUENCE: 14
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360 accccccctgt gcgtgaccct gcactgcacc aacctgaaga acgccaccaa caccaagagc 420
agcaactgga aggagatgga ccgcggcgag atcaagaact gcagcttcaa ggtgggcgcc 480
ggcaagctga tcaactgcaa caccagcgtg atcacccagg cctgccccaa ggtgagcttc 540
gagcccatcc ccatccacta ctgcgccccc gccggcttcg ccatcctgaa gtgcaacgac 600
aagaagttca acggcagcgg cccctgcacc aacgtgagca ccgtgcagtg cacccacggc 660
atccgccccg tggtgagcac ccagctgctg ctgaacggca gcctggccga ggagggcgtg 720
gtgatccgca gcgagaactt caccgacaac gccaagacca tcatcgtgca gctgaaggag 780
agcgtggaga tcaactgcac ccgccccaac aacaacaccc gcaagagcat caccatcggc 840
cccggccgcg ccttctacgc caccggcgac atcatcggcg acatccgcca ggcccactgc 900
aacatcagcg gcgagaagtg gaacaacacc ctgaagcaga tcgtgaccaa gctgcaggcc 960
cagttcggca acaagaccat cgtgttcaag cagagcagcg gcggcgaccc cgagatcgtg 1020
atgcacagct tcaactgcgg cggcgagttc ttctactgca acagcaccca gctgttcaac 1080
agcacctgga acaacaccat cggccccaac aacaccaacg gcaccatcac cctgccctgc 1140
cgcatcaagc agatcatcaa ccgctggcag gaggtgggca aggccatgta cgcccccccc 1200
atccgcggcc agatccgctg cagcagcaac atcaccggcc tgctgctgac ccgcgacggc 1260
ggcaaggaga tcagcaacac caccgagatc ttccgccccg gcggcggcga catgcgcgac 1320
aactggcgca gcgagctgta caagtacaag gtggtgaaga tcgagcccct gggcgtggcc 1380
cccaccaagg ccatcagcag cgtggtgcag agcgagaaga gcgccgtgac cctgggcgcc 1440
atgttcctgg gcttcctggg cgccgccggc agcaccatgg gcgcccgcag cctgaccctg 1500
accgtgcagg cccgccagct gctgagcggc atcgtgcagc agcagaacaa cctgctgcgc 1560
gccatcgagg cccagcagca cctgctgcag ctgaccgtgt ggggcatcaa gcagctgcag 1620
gcccgcgtgc tggccgtgga gcgctacctg aaggaccagc agctgctggg catctggggc 1680
tgcagcggca agctgatctg caccaccgcc gtgccctgga acgccagctg gagcaacaag 1740
agcctggacc agatctggaa caacatgacc tggatggagt gggagcgcga gatcgacaac 1800
tacaccaacc tgatctacac cctgatcgag gagagccaga accagcagga gaagaacgag 1860
caggagctgc tggagctgga caagtgggcc agcctgtgga actggttcga catcagcaag 1920
tggctgtggt acatctaact cgag 1944

-continued

<210> SEQ ID NO 15
<211> LENGTH: 1836
<212> TYPE: DNA
<213> ORGANISM: Artificial Sequence
<220> FEATURE:
<223> OTHER INFORMATION: gp140.mut7.modSF162.delV1/V2

<400> SEQUENCE: 15
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360
acccccctgt gcgtgggcgc cggcaactgc cagaccagcg tgatcaccca ggcctgcccc 420
aaggtgagct tcgagcccat ccccatccac tactgcgccc ccgccggctt cgccatcctg 480
aagtgcaacg acaagaagtt caacggcagc ggcccctgca ccaacgtgag caccgtgcag 540
tgcacccacg gcatccgccc cgtggtgagc acccagctgc tgctgaacgg cagcctggcc 600
gaggagggcg tggtgatccg cagcgagaac ttcaccgaca acgccaagac catcatcgtg 660
cagctgaagg agagcgtgga gatcaactgc acccgcccca acaacaacac ccgcaagagc 720
atcaccatcg gccccggccg cgccttctac gccaccggcg acatcatcgg cgacatccgc 780
caggcccact gcaacatcag cggcgagaag tggaacaaca ccctgaagca gatcgtgacc 840
aagctgcagg cccagttcgg caacaagacc atcgtgttca agcagagcag cggcggcgac 900
cccgagatcg tgatgcacag cttcaactgc ggcggcgagt tcttctactg caacagcacc 960
cagctgttca acagcacctg gaacaacacc atcggcccca acaacaccaa cggcaccatc 1020
accctgccct gccgcatcaa gcagatcatc aaccgctggc aggaggtggg caaggccatg 1080
tacgcccccc ccatccgcgg ccagatccgc tgcagcagca acatcaccgg cctgctgctg 1140
acccgcgacg gcggcaagga gatcagcaac accaccgaga tcttccgccc cggcggcggc 1200
gacatgcgcg acaactggcg cagcgagctg tacaagtaca aggtggtgaa gatcgagccc 1260
ctgggcgtgg cccccaccaa ggccatcagc agcgtggtgc agagcgagaa gagcgccgtg 1320
accctgggcg ccatgttcct gggcttcctg ggcgccgccg gcagcaccat gggcgcccgc 1380
agcctgaccc tgaccgtgca ggcccgccag ctgctgagcg gcatcgtgca gcagcagaac 1440
aacctgctgc gcgccatcga ggcccagcag cacctgctgc agctgaccgt gtggggcatc 1500
aagcagctgc aggcccgcgt gctggccgtg gagcgctacc tgaaggacca gcagctgctg 1560
ggcatctggg gctgcagcgg caagctgatc tgcaccaccg ccgtgccctg gaacgccagc 1620
tggagcaaca agagcctgga ccagatctgg aacaacatga cctggatgga gtgggagcgc 1680
gagatcgaca actacaccaa cctgatctac accctgatcg aggagagcca gaaccagcag 1740
gagaagaacg agcaggagct gctggagctg gacaagtggg ccagcctgtg gaactggttc 1800
gacatcagca agtggctgtg gtacatctaa ctcgag 1836

<210> SEQ ID NO 16
<211> LENGTH: 2025
<212> TYPE: DNA
<213> ORGANISM: Artificial Sequence
<220> FEATURE:
<223> OTHER INFORMATION: gp140.mut8.modSF162

-continued

<400> SEQUENCE: 16
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360
acccccctgt gcgtgaccct gcactgcacc aacctgaaga acgccaccaa caccaagagc 420
agcaactgga aggagatgga ccgcggcgag atcaagaact gcagcttcaa ggtgaccacc 480
agcatccgca acaagatgca gaaggagtac gccctgttct acaagctgga cgtggtgccc 540
atcgacaacg acaacaccag ctacaagctg atcaactgca acaccagcgt gatcacccag 600
gcctgcccca aggtgagctt cgagcccatc cccatccact actgcgcccc cgccggcttc 660
gccatcctga agtgcaacga caagaagttc aacggcagcg gcccctgcac caacgtgagc 720
accgtgcagt gcacccacgg catccgcccc gtggtgagca cccagctgct gctgaacggc 780
agcctggccg aggagggcgt ggtgatccgc agcgagaact tcaccgacaa cgccaagacc 840
atcatcgtgc agctgaagga gagcgtggag atcaactgca cccgccccaa caacaacacc 900
cgcaagagca tcaccatcgg ccccggccgc gccttctacg ccaccggcga catcatcggc 960
gacatccgcc aggcccactg caacatcagc ggcgagaagt ggaacaacac cctgaagcag 1020
atcgtgacca agctgcaggc ccagttcggc aacaagacca tcgtgttcaa gcagagcagc 1080
ggcggcgacc ccgagatcgt gatgcacagc ttcaactgcg gcggcgagtt cttctactgc 1140
aacagcaccc agctgttcaa cagcacctgg aacaacacca tcggccccaa caacaccaac 1200
ggcaccatca ccctgccctg ccgcatcaag cagatcatca accgctggca ggaggtgggc 1260
aaggccatgt acgccccccc catccgcggc cagatccgct gcagcagcaa catcaccggc 1320
ctgctgctga cccgcgacgg cggcaaggag atcagcaaca ccaccgagat cttccgcccc 1380
ggcggcggcg acatgcgcga caactggcgc agcgagctgt acaagtacaa ggtggtgaag 1440
atcgagcccc tgggcgtggc ccccaccatc gccatcagca gcgtggtgca gagcgagaag 1500
agcgccgtga ccctgggcgc catgttcctg ggcttcctgg gcgccgccgg cagcaccatg 1560
ggcgcccgca gcctgaccct gaccgtgcag gcccgccagc tgctgagcgg catcgtgcag 1620
cagcagaaca acctgctgcg cgccatcgag gcccagcagc acctgctgca gctgaccgtg 1680
tggggcatca agcagctgca ggcccgcgtg ctggccgtgg agcgctacct gaaggaccag 1740
cagctgctgg gcatctgggg ctgcagcggc aagctgatct gcaccaccgc cgtgccctgg 1800
aacgccagct ggagcaacaa gagcctggac cagatctgga acaacatgac ctggatggag 1860
tgggagcgcg agatcgacaa ctacaccaac ctgatctaca ccctgatcga ggagagccag 1920
aaccagcagg agaagaacga gcaggagctg ctggagctgg acaagtgggc cagcctgtgg 1980
aactggttcg acatcagcaa gtggctgtgg tacatctaac tcgag 2025

<210> SEQ ID NO 17
<211> LENGTH: 1944
<212> TYPE: DNA
<213> ORGANISM: Artificial Sequence
<220> FEATURE:
<223> OTHER INFORMATION: gp140.mut8.modSF162.delV2

-continued

<400> SEQUENCE: 17

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg ggccacccac gcctgcgtgc ccaccgaccc caacccccag    240
gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360
acccccctgt gcgtgaccct gcactgcacc aacctgaaga acgccaccaa caccaagagc    420
agcaactgga aggagatgga ccgcggcgag atcaagaact gcagcttcaa ggtgggcgcc    480
ggcaagctga tcaactgcaa caccagcgtg atcacccagg cctgccccaa ggtgagcttc    540
gagcccatcc ccatccacta ctgcgccccc gccggcttcg ccatcctgaa gtgcaacgac    600
aagaagttca acggcagcgg cccctgcacc aacgtgagca ccgtgcagtg cacccacggc    660
atccgccccg tggtgagcac ccagctgctg ctgaacggca gcctggccga ggagggcgtg    720
gtgatccgca gcgagaactt caccgacaac gccaagacca tcatcgtgca gctgaaggag    780
agcgtggaga tcaactgcac ccgccccaac aacaacaccc gcaagagcat caccatcggc    840
cccggccgcg ccttctacgc caccggcgac atcatcggcg acatccgcca ggcccactgc    900
aacatcagcg gcgagaagtg gaacaacacc ctgaagcaga tcgtgaccaa gctgcaggcc    960
cagttcggca acaagaccat cgtgttcaag cagagcagcg gcggcgaccc cgagatcgtg   1020
atgcacagct tcaactgcgg cggcgagttc ttctactgca acagcaccca gctgttcaac   1080
agcacctgga acaacaccat cggccccaac aacaccaacg gcaccatcac cctgccctgc   1140
cgcatcaagc agatcatcaa ccgctggcag gaggtgggca aggccatgta cgcccccccc   1200
atccgcggcc agatccgctg cagcagcaac atcaccggcc tgctgctgac ccgcgacggc   1260
ggcaaggaga tcagcaacac caccgagatc ttccgccccg gcggcggcga catgcgcgac   1320
aactggcgca gcgagctgta caagtacaag gtggtgaaga tcgagcccct gggcgtggcc   1380
cccaccatcg ccatcagcag cgtggtgcag agcgagaaga gcgccgtgac cctgggcgcc   1440
atgttcctgg gcttcctggg cgccgccggc agcaccatgg gcgcccgcag cctgaccctg   1500
accgtgcagg cccgccagct gctgagcggc atcgtgcagc agcagaacaa cctgctgcgc   1560
gccatcgagg cccagcagca cctgctgcag ctgaccgtgt ggggcatcaa gcagctgcag   1620
gcccgcgtgc tggccgtgga gcgctacctg aaggaccagc agctgctggg catctggggc   1680
tgcagcggca agctgatctg caccaccgcc gtgccctgga acgccagctg gagcaacaag   1740
agcctggacc agatctggaa caacatgacc tggatggagt gggagcgcga gatcgacaac   1800
tacaccaacc tgatctacac cctgatcgag gagagccaga accagcagga gaagaacgag   1860
caggagctgc tggagctgga caagtgggcc agcctgtgga actggttcga catcagcaag   1920
tggctgtggt acatctaact cgag                                          1944
```

<210> SEQ ID NO 18
<211> LENGTH: 1836
<212> TYPE: DNA
<213> ORGANISM: Artificial Sequence
<220> FEATURE:
<223> OTHER INFORMATION: gp140.mut8.modSF162.delV1/V2

<400> SEQUENCE: 18

```
gaattcgcca ccatggatgc aatgaagaga gggctctgct gtgtgctgct gctgtgtgga     60
```

gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360 accccccctgt gcgtgggcgc cggcaactgc cagaccagcg tgatcaccca ggcctgcccc 420
aaggtgagct tcgagcccat ccccatccac tactgcgccc ccgccggctt cgccatcctg 480
aagtgcaacg acaagaagtt caacggcagc ggcccctgca ccaacgtgag caccgtgcag 540
tgcacccacg gcatccgccc cgtggtgagc acccagctgc tgctgaacgg cagcctggcc 600
gaggagggcg tggtgatccg cagcgagaac ttcaccgaca acgccaagac catcatcgtg 660
cagctgaagg agagcgtgga gatcaactgc acccgcccca acaacaacac ccgcaagagc 720
atcaccatcg gccccggccg cgccttctac gccaccggcg acatcatcgg cgacatccgc 780
caggcccact gcaacatcag cggcgagaag tggaacaaca ccctgaagca gatcgtgacc 840
aagctgcagg cccagttcgg caacaagacc atcgtgttca agcagagcag cggcggcgac 900
cccgagatcg tgatgcacag cttcaactgc ggcggcgagt tcttctactg caacagcacc 960
cagctgttca acagcacctg gaacaacacc atcggcccca acaacaccaa cggcaccatc 1020
accctgccct gccgcatcaa gcagatcatc aaccgctggc aggaggtggg caaggccatg 1080
tacgcccccc ccatccgcgg ccagatccgc tgcagcagca acatcaccgg cctgctgctg 1140
acccgcgacg gcggcaagga gatcagcaac accaccgaga tcttccgccc cggcggcggc 1200
gacatgcgcg acaactggcg cagcgagctg tacaagtaca aggtggtgaa gatcgagccc 1260
ctgggcgtgg cccccaccat cgccatcagc agcgtggtgc agagcgagaa gagcgccgtg 1320
accctgggcg ccatgttcct gggcttcctg ggcgccgccg gcagcaccat gggcgcccgc 1380
agcctgaccc tgaccgtgca ggcccgccag ctgctgagcg gcatcgtgca gcagcagaac 1440
aacctgctgc gcgccatcga ggcccagcag cacctgctgc agctgaccgt gtggggcatc 1500
aagcagctgc aggcccgcgt gctggccgtg gagcgctacc tgaaggacca gcagctgctg 1560
ggcatctggg gctgcagcgg caagctgatc tgcaccaccg ccgtgccctg gaacgccagc 1620
tggagcaaca agagcctgga ccagatctgg aacaacatga cctggatgga gtgggagcgc 1680
gagatcgaca actacaccaa cctgatctac accctgatcg aggagagcca gaaccagcag 1740
gagaagaacg agcaggagct gctggagctg gacaagtggg ccagcctgtg gaactggttc 1800
gacatcagca agtggctgtg gtacatctaa ctcgag 1836

<210> SEQ ID NO 19
<211> LENGTH: 2547
<212> TYPE: DNA
<213> ORGANISM: Artificial Sequence
<220> FEATURE:
<223> OTHER INFORMATION: gp160.modSF162

<400> SEQUENCE: 19
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240

-continued

```
gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360
acccccctgt gcgtgaccct gcactgcacc aacctgaaga acgccaccaa caccaagagc    420
agcaactgga aggagatgga ccgcggcgag atcaagaact gcagcttcaa ggtgaccacc    480
agcatccgca acaagatgca gaaggagtac gccctgttct acaagctgga cgtggtgccc    540
atcgacaacg acaacaccag ctacaagctg atcaactgca acaccagcgt gatcacccag    600
gcctgcccca aggtgagctt cgagcccatc cccatccact actgcgcccc cgccggcttc    660
gccatcctga agtgcaacga caagaagttc aacggcagcg gcccctgcac caacgtgagc    720
accgtgcagt gcacccacgg catccgcccc gtggtgagca cccagctgct gctgaacggc    780
agcctggccg aggagggcgt ggtgatccgc agcgagaact tcaccgacaa cgccaagacc    840
atcatcgtgc agctgaagga gagcgtggag atcaactgca cccgccccaa caacaacacc    900
cgcaagagca tcaccatcgg ccccggccgc gccttctacg ccaccggcga catcatcggc    960
gacatccgcc aggcccactg caacatcagc ggcgagaagt ggaacaacac cctgaagcag   1020
atcgtgacca agctgcaggc ccagttcggc aacaagacca tcgtgttcaa gcagagcagc   1080
ggcggcgacc ccgagatcgt gatgcacagc ttcaactgcg gcggcgagtt cttctactgc   1140
aacagcaccc agctgttcaa cagcacctgg aacaacacca tcggccccaa caacaccaac   1200
ggcaccatca ccctgccctg ccgcatcaag cagatcatca accgctggca ggaggtgggc   1260
aaggccatgt acgccccccc catccgcggc cagatccgct gcagcagcaa catcaccggc   1320
ctgctgctga cccgcgacgg cggcaaggag atcagcaaca ccaccgagat cttccgcccc   1380
ggcggcggcg acatgcgcga caactggcgc agcgagctgt acaagtacaa ggtggtgaag   1440
atcgagcccc tgggcgtggc ccccaccaag gccaagcgcc gcgtggtgca gcgcgagaag   1500
cgcgccgtga ccctgggcgc catgttcctg ggcttcctgg gcgccgccgg cagcaccatg   1560
ggcgcccgca gcctgaccct gaccgtgcag gcccgccagc tgctgagcgg catcgtgcag   1620
cagcagaaca acctgctgcg cgccatcgag gcccagcagc acctgctgca gctgaccgtg   1680
tggggcatca agcagctgca ggcccgcgtg ctggccgtgg agcgctacct gaaggaccag   1740
cagctgctgg gcatctgggg ctgcagcggc aagctgatct gcaccaccgc cgtgccctgg   1800
aacgccagct ggagcaacaa gagcctggac cagatctgga acaacatgac ctggatggag   1860
tgggagcgcg agatcgacaa ctacaccaac ctgatctaca ccctgatcga ggagagccag   1920
aaccagcagg agaagaacga gcaggagctg ctggagctgg acaagtgggc cagcctgtgg   1980
aactggttcg acatcagcaa gtggctgtgg tacatcaaga tcttcatcat gatcgtgggc   2040
ggcctggtgg gcctgcgcat cgtgttcacc gtgctgagca tcgtgaaccg cgtgcgccag   2100
ggctacagcc ccctgagctt ccagacccgc ttccccgccc cccgcggccc cgaccgcccc   2160
gagggcatcg aggaggaggg cggcgagcgc gaccgcgacc gcagcagccc cctggtgcac   2220
ggcctgctgg ccctgatctg ggacgacctg cgcagcctgt gcctgttcag ctaccaccgc   2280
ctgcgcgacc tgatcctgat cgccgcccgc atcgtggagc tgctgggccg ccgcggctgg   2340
gaggccctga agtactgggg caacctgctg cagtactgga tccaggagct gaagaacagc   2400
gccgtgagcc tgttcgacgc catcgccatc gccgtggccg agggcaccga ccgcatcatc   2460
gaggtggccc agcgcatcgg ccgcgccttc ctgcacatcc cccgccgcat ccgccagggc   2520
ttcgagcgcg ccctgctgta actcgag                                       2547
```

-continued

<210> SEQ ID NO 20
<211> LENGTH: 2466
<212> TYPE: DNA
<213> ORGANISM: Artificial Sequence
<220> FEATURE:
<223> OTHER INFORMATION: gp160.modSF162.delV2

<400> SEQUENCE: 20
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360 accccctgt gcgtgaccct gcactgcacc aacctgaaga acgccaccaa caccaagagc 420
agcaactgga aggagatgga ccgcggcgag atcaagaact gcagcttcaa ggtgggcgcc 480
ggcaagctga tcaactgcaa caccagcgtg atcacccagg cctgccccaa ggtgagcttc 540
gagcccatcc ccatccacta ctgcgccccc gccggcttcg ccatcctgaa gtgcaacgac 600
aagaagttca acggcagcgg cccctgcacc aacgtgagca ccgtgcagtg cacccacggc 660
atccgccccg tggtgagcac ccagctgctg ctgaacggca gcctggccga ggagggcgtg 720
gtgatccgca gcgagaactt caccgacaac gccaagacca tcatcgtgca gctgaaggag 780
agcgtggaga tcaactgcac ccgccccaac aacaacaccc gcaagagcat caccatcggc 840
cccggccgcg ccttctacgc caccggcgac atcatcggcg acatccgcca ggcccactgc 900
aacatcagcg gcgagaagtg gaacaacacc ctgaagcaga tcgtgaccaa gctgcaggcc 960
cagttcggca acaagaccat cgtgttcaag cagagcagcg gcggcgaccc cgagatcgtg 1020
atgcacagct tcaactgcgg cggcgagttc ttctactgca acagcaccca gctgttcaac 1080
agcacctgga acaacaccat cggccccaac aacaccaacg gcaccatcac cctgccctgc 1140
cgcatcaagc agatcatcaa ccgctggcag gaggtgggca aggccatgta cgcccccccc 1200
atccgcggcc agatccgctg cagcagcaac atcaccggcc tgctgctgac ccgcgacggc 1260
ggcaaggaga tcagcaacac caccgagatc ttccgccccg gcggcggcga catgcgcgac 1320
aactggcgca gcgagctgta caagtacaag gtggtgaaga tcgagcccct gggcgtggcc 1380
cccaccaagg ccaagcgccg cgtggtgcag cgcgagaagc gcgccgtgac cctgggcgcc 1440
atgttcctgg gcttcctggg cgccgccggc agcaccatgg gcgcccgcag cctgaccctg 1500
accgtgcagg cccgccagct gctgagcggc atcgtgcagc agcagaacaa cctgctgcgc 1560
gccatcgagg cccagcagca cctgctgcag ctgaccgtgt ggggcatcaa gcagctgcag 1620
gcccgcgtgc tggccgtgga gcgctacctg aaggaccagc agctgctggg catctggggc 1680
tgcagcggca agctgatctg caccaccgcc gtgccctgga acgccagctg gagcaacaag 1740
agcctggacc agatctggaa caacatgacc tggatggagt gggagcgcga gatcgacaac 1800
tacaccaacc tgatctacac cctgatcgag gagagccaga accagcagga gaagaacgag 1860
caggagctgc tggagctgga caagtgggcc agcctgtgga actggttcga catcagcaag 1920
tggctgtggt acatcaagat cttcatcatg atcgtgggcg gcctggtggg cctgcgcatc 1980
gtgttcaccg tgctgagcat cgtgaaccgc gtgcgccagg gctacagccc cctgagcttc 2040
cagacccgct tccccgcccc ccgcggcccc gaccgccccg agggcatcga ggaggagggc 2100
ggcgagcgcg accgcgaccg cagcagcccc ctggtgcacg gcctgctggc cctgatctgg 2160
gacgacctgc gcagcctgtg cctgttcagc taccaccgcc tgcgcgacct gatcctgatc 2220
gccgcccgca tcgtggagct gctgggccgc cgcggctggg aggccctgaa gtactggggc 2280
aacctgctgc agtactggat ccaggagctg aagaacagcg ccgtgagcct gttcgacgcc 2340
atcgccatcg ccgtggccga gggcaccgac cgcatcatcg aggtggccca gcgcatcggc 2400
cgcgccttcc tgcacatccc ccgccgcatc cgccagggct tcgagcgcgc cctgctgtaa 2460
ctcgag 2466

<210> SEQ ID NO 21
<211> LENGTH: 2358
<212> TYPE: DNA
<213> ORGANISM: Artificial Sequence
<220> FEATURE:
<223> OTHER INFORMATION: gp160.modSF162.delV1/V2

<400> SEQUENCE: 21
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360 accccccctgt gcgtgggcgc cggcaactgc cagaccagcg tgatcaccca ggcctgcccc 420
aaggtgagct tcgagcccat ccccatccac tactgcgccc ccgccggctt cgccatcctg 480
aagtgcaacg acaagaagtt caacggcagc ggcccctgca ccaacgtgag caccgtgcag 540
tgcacccacg gcatccgccc cgtggtgagc acccagctgc tgctgaacgg cagcctggcc 600
gaggagggcg tggtgatccg cagcgagaac ttcaccgaca acgccaagac catcatcgtg 660
cagctgaagg agagcgtgga gatcaactgc acccgcccca acaacaacac ccgcaagagc 720
atcaccatcg gccccggccg cgccttctac gccaccggcg acatcatcgg cgacatccgc 780
caggcccact gcaacatcag cggcgagaag tggaacaaca ccctgaagca gatcgtgacc 840
aagctgcagg cccagttcgg caacaagacc atcgtgttca agcagagcag cggcggcgac 900
cccgagatcg tgatgcacag cttcaactgc ggcggcgagt tcttctactg caacagcacc 960
cagctgttca acagcacctg gaacaacacc atcggcccca acaacaccaa cggcaccatc 1020
accctgccct gccgcatcaa gcagatcatc aaccgctggc aggaggtggg caaggccatg 1080
tacgcccccc ccatccgcgg ccagatccgc tgcagcagca acatcaccgg cctgctgctg 1140
acccgcgacg gcggcaagga gatcagcaac accaccgaga tcttccgccc cggcggcggc 1200
gacatgcgcg acaactggcg cagcgagctg tacaagtaca aggtggtgaa gatcgagccc 1260
ctgggcgtgg cccccaccaa ggccaagcgc cgcgtggtgc agcgcgagaa gcgcgccgtg 1320
accctgggcg ccatgttcct gggcttcctg ggcgccgccg gcagcaccat gggcgcccgc 1380
agcctgaccc tgaccgtgca ggcccgccag ctgctgagcg gcatcgtgca gcagcagaac 1440
aacctgctgc gcgccatcga ggcccagcag cacctgctgc agctgaccgt gtggggcatc 1500
aagcagctgc aggcccgcgt gctggccgtg gagcgctacc tgaaggacca gcagctgctg 1560
ggcatctggg gctgcagcgg caagctgatc tgcaccaccg ccgtgccctg gaacgccagc 1620
tggagcaaca agagcctgga ccagatctgg aacaacatga cctggatgga gtgggagcgc 1680
gagatcgaca actacaccaa cctgatctac accctgatcg aggagagcca gaaccagcag 1740
gagaagaacg agcaggagct gctggagctg gacaagtggg ccagcctgtg gaactggttc 1800
gacatcagca agtggctgtg gtacatcaag atcttcatca tgatcgtggg cggcctggtg 1860
ggcctgcgca tcgtgttcac cgtgctgagc atcgtgaacc gcgtgcgcca gggctacagc 1920
cccctgagct tccagacccg cttccccgcc ccccgcggcc ccgaccgccc cgagggcatc 1980
gaggaggagg gcggcgagcg cgaccgcgac cgcagcagcc ccctggtgca cggcctgctg 2040
gccctgatct gggacgacct gcgcagcctg tgcctgttca gctaccaccg cctgcgcgac 2100
ctgatcctga tcgccgcccg catcgtggag ctgctgggcc gccgcggctg ggaggccctg 2160
aagtactggg gcaacctgct gcagtactgg atccaggagc tgaagaacag cgccgtgagc 2220
ctgttcgacg ccatcgccat cgccgtggcc gagggcaccg accgcatcat cgaggtggcc 2280
cagcgcatcg gccgcgcctt cctgcacatc ccccgccgca tccgccaggg cttcgagcgc 2340
gccctgctgt aactcgag 2358

<210> SEQ ID NO 22
<211> LENGTH: 681
<212> TYPE: PRT
<213> ORGANISM: Artificial Sequence
<220> FEATURE:
<223> OTHER INFORMATION: Clade C TV1c8.2 TPA

<400> SEQUENCE: 22

Met Asp Ala Met Lys Arg Gly Leu Cys Cys Val Leu Leu Leu Cys Gly
1 5 10 15

Ala Val Phe Val Ser Pro Asn Thr Glu Asp Leu Trp Val Thr Val Tyr
20 25 30

Tyr Gly Val Pro Val Trp Arg Asp Ala Lys Thr Thr Leu Phe Cys Ala
35 40 45

Ser Asp Ala Lys Ala Tyr Glu Thr Glu Val His Asn Val Trp Ala Thr
50 55 60

His Ala Cys Val Pro Thr Asp Pro Asn Pro Gln Glu Ile Val Leu Gly
65 70 75 80

Asn Val Thr Glu Asn Phe Asn Met Trp Lys Asn Asp Met Ala Asp Gln
85 90 95

Met His Glu Asp Val Ile Ser Leu Trp Asp Gln Ser Leu Lys Pro Cys
100 105 110

Val Lys Leu Thr Pro Leu Cys Val Thr Leu Asn Cys Thr Asp Thr Asn
115 120 125

Val Thr Gly Asn Arg Thr Val Thr Gly Asn Ser Thr Asn Asn Thr Asn
130 135 140

Gly Thr Gly Ile Tyr Asn Ile Glu Glu Met Lys Asn Cys Ser Phe Asn
145 150 155 160

Ala Thr Thr Glu Leu Arg Asp Lys Lys His Lys Glu Tyr Ala Leu Phe
165 170 175

Tyr Arg Leu Asp Ile Val Pro Leu Asn Glu Asn Ser Asp Asn Phe Thr
180 185 190

Tyr Arg Leu Ile Asn Cys Asn Thr Ser Thr Ile Thr Gln Ala Cys Pro
195 200 205

Lys Val Ser Phe Asp Pro Ile Pro Ile His Tyr Cys Ala Pro Ala Gly
210 215 220

Tyr Ala Ile Leu Lys Cys Asn Asn Lys Thr Phe Asn Gly Thr Gly Pro
225 230 235 240

-continued

```
Cys Tyr Asn Val Ser Thr Val Gln Cys Thr His Gly Ile Lys Pro Val
                245                 250                 255

Val Ser Thr Gln Leu Leu Leu Asn Gly Ser Leu Ala Glu Glu Gly Ile
            260                 265                 270

Ile Ile Arg Ser Glu Asn Leu Thr Glu Asn Thr Lys Thr Ile Ile Val
        275                 280                 285

His Leu Asn Glu Ser Val Glu Ile Asn Cys Thr Arg Pro Asn Asn Asn
    290                 295                 300

Thr Arg Lys Ser Val Arg Ile Gly Pro Gly Gln Ala Phe Tyr Ala Thr
305                 310                 315                 320

Asn Asp Val Ile Gly Asn Ile Arg Gln Ala His Cys Asn Ile Ser Thr
                325                 330                 335

Asp Arg Trp Asn Lys Thr Leu Gln Gln Val Met Lys Lys Leu Gly Glu
            340                 345                 350

His Phe Pro Asn Lys Thr Ile Gln Phe Lys Pro His Ala Gly Gly Asp
        355                 360                 365

Leu Glu Ile Thr Met His Ser Phe Asn Cys Arg Gly Glu Phe Phe Tyr
    370                 375                 380

Cys Asn Thr Ser Asn Leu Phe Asn Ser Thr Tyr His Ser Asn Asn Gly
385                 390                 395                 400

Thr Tyr Lys Tyr Asn Gly Asn Ser Ser Ser Pro Ile Thr Leu Gln Cys
                405                 410                 415

Lys Ile Lys Gln Ile Val Arg Met Trp Gln Gly Val Gly Gln Ala Thr
            420                 425                 430

Tyr Ala Pro Pro Ile Ala Gly Asn Ile Thr Cys Arg Ser Asn Ile Thr
        435                 440                 445

Gly Ile Leu Leu Thr Arg Asp Gly Gly Phe Asn Thr Thr Asn Asn Thr
    450                 455                 460

Glu Thr Phe Arg Pro Gly Gly Gly Asp Met Arg Asp Asn Trp Arg Ser
465                 470                 475                 480

Glu Leu Tyr Lys Tyr Lys Val Val Glu Ile Lys Pro Leu Gly Ile Ala
                485                 490                 495

Pro Thr Lys Ala Ile Ser Ser Val Val Gln Ser Glu Lys Ser Ala Val
            500                 505                 510

Gly Ile Gly Ala Val Phe Leu Gly Phe Leu Gly Ala Ala Gly Ser Thr
        515                 520                 525

Met Gly Ala Ala Ser Ile Thr Leu Thr Val Gln Ala Arg Gln Leu Leu
    530                 535                 540

Ser Gly Ile Val Gln Gln Gln Ser Asn Leu Leu Lys Ala Ile Glu Ala
545                 550                 555                 560

Gln Gln His Met Leu Gln Leu Thr Val Trp Gly Ile Lys Gln Leu Gln
                565                 570                 575

Ala Arg Val Leu Ala Ile Glu Arg Tyr Leu Lys Asp Gln Gln Leu Leu
            580                 585                 590

Gly Ile Trp Gly Cys Ser Gly Arg Leu Ile Cys Thr Thr Ala Val Pro
        595                 600                 605

Trp Asn Ser Ser Trp Ser Asn Lys Ser Glu Lys Asp Ile Trp Asp Asn
    610                 615                 620

Met Thr Trp Met Gln Trp Asp Arg Glu Ile Ser Asn Tyr Thr Gly Leu
625                 630                 635                 640

Ile Tyr Asn Leu Leu Glu Asp Ser Gln Asn Gln Gln Glu Lys Asn Glu
                645                 650                 655
```

Lys Asp Leu Leu Glu Leu Asp Lys Trp Asn Asn Leu Trp Asn Trp Phe
660 665 670

Asp Ile Ser Asn Trp Pro Trp Tyr Ile
675 680

<210> SEQ ID NO 23
<211> LENGTH: 668
<212> TYPE: PRT
<213> ORGANISM: Artificial Sequence
<220> FEATURE:
<223> OTHER INFORMATION: Clade B SF162 TPA

<400> SEQUENCE: 23

Met Asp Ala Met Lys Arg Gly Leu Cys Cys Val Leu Leu Leu Cys Gly
1 5 10 15

Ala Val Phe Val Ser Pro Ser Ala Val Glu Lys Leu Trp Val Thr Val
20 25 30

Tyr Tyr Gly Val Pro Val Trp Lys Glu Ala Thr Thr Thr Leu Phe Cys
35 40 45

Ala Ser Asp Ala Lys Ala Tyr Asp Thr Glu Val His Asn Val Trp Ala
50 55 60

Thr His Ala Cys Val Pro Thr Asp Pro Asn Pro Gln Glu Ile Val Leu
65 70 75 80

Glu Asn Val Thr Glu Asn Phe Asn Met Trp Lys Asn Asn Met Val Glu
85 90 95

Gln Met His Glu Asp Ile Ile Ser Leu Trp Asp Gln Ser Leu Lys Pro
100 105 110

Cys Val Lys Leu Thr Pro Leu Cys Val Thr Leu His Cys Thr Asn Leu
115 120 125

Lys Asn Ala Thr Asn Thr Lys Ser Ser Asn Trp Lys Glu Met Asp Arg
130 135 140

Gly Glu Ile Lys Asn Cys Ser Phe Lys Val Thr Thr Ser Ile Arg Asn
145 150 155 160

Lys Met Gln Lys Glu Tyr Ala Leu Phe Tyr Lys Leu Asp Val Val Pro
165 170 175

Ile Asp Asn Asp Asn Thr Ser Tyr Lys Leu Ile Asn Cys Asn Thr Ser
180 185 190

Val Ile Thr Gln Ala Cys Pro Lys Val Ser Phe Glu Pro Ile Pro Ile
195 200 205

His Tyr Cys Ala Pro Ala Gly Phe Ala Ile Leu Lys Cys Asn Asp Lys
210 215 220

Lys Phe Asn Gly Ser Gly Pro Cys Thr Asn Val Ser Thr Val Gln Cys
225 230 235 240

Thr His Gly Ile Arg Pro Val Val Ser Thr Gln Leu Leu Leu Asn Gly
245 250 255

Ser Leu Ala Glu Glu Gly Val Val Ile Arg Ser Glu Asn Phe Thr Asp
260 265 270

Asn Ala Lys Thr Ile Ile Val Gln Leu Lys Glu Ser Val Glu Ile Asn
275 280 285

Cys Thr Arg Pro Asn Asn Asn Thr Arg Lys Ser Ile Thr Ile Gly Pro
290 295 300

Gly Arg Ala Phe Tyr Ala Thr Gly Asp Ile Ile Gly Asp Ile Arg Gln
305 310 315 320

Ala His Cys Asn Ile Ser Gly Glu Lys Trp Asn Asn Thr Leu Lys Gln
325 330 335

-continued

```
Ile Val Thr Lys Leu Gln Ala Gln Phe Gly Asn Lys Thr Ile Val Phe
            340                 345                 350

Lys Gln Ser Ser Gly Gly Asp Pro Glu Ile Val Met His Ser Phe Asn
        355                 360                 365

Cys Gly Gly Glu Phe Phe Tyr Cys Asn Ser Thr Gln Leu Phe Asn Ser
    370                 375                 380

Thr Trp Asn Asn Thr Ile Gly Pro Asn Asn Thr Asn Gly Thr Ile Thr
385                 390                 395                 400

Leu Pro Cys Arg Ile Lys Gln Ile Ile Asn Arg Trp Gln Glu Val Gly
                405                 410                 415

Lys Ala Met Tyr Ala Pro Pro Ile Arg Gly Gln Ile Arg Cys Ser Ser
            420                 425                 430

Asn Ile Thr Gly Leu Leu Leu Thr Arg Asp Gly Gly Lys Glu Ile Ser
        435                 440                 445

Asn Thr Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Lys Ala Ile Ser Ser Val Val Gln Ser Glu Lys
                485                 490                 495

Ser Ala Val Thr Leu Gly Ala Met Phe Leu Gly Phe Leu Gly Ala Ala
            500                 505                 510

Gly Ser Thr Met Gly Ala Arg Ser Leu Thr Leu Thr Val Gln Ala Arg
        515                 520                 525

Gln Leu Leu Ser Gly Ile Val Gln Gln Gln Asn Asn Leu Leu Arg Ala
    530                 535                 540

Ile Glu Ala Gln Gln His Leu Leu Gln Leu Thr Val Trp Gly Ile Lys
545                 550                 555                 560

Gln Leu Gln Ala Arg Val Leu Ala Val Glu Arg Tyr Leu Lys Asp Gln
                565                 570                 575

Gln Leu Leu Gly Ile Trp Gly Cys Ser Gly Lys Leu Ile Cys Thr Thr
            580                 585                 590

Ala Val Pro Trp Asn Ala Ser Trp Ser Asn Lys Ser Leu Asp Gln Ile
        595                 600                 605

Trp Asn Asn Met Thr Trp Met Glu Trp Glu Arg Glu Ile Asp Asn Tyr
    610                 615                 620

Thr Asn Leu Ile Tyr Thr Leu Ile Glu Glu Ser Gln Asn Gln Gln Glu
625                 630                 635                 640

Lys Asn Glu Gln Glu Leu Leu Glu Leu Asp Lys Trp Ala Ser Leu Trp
                645                 650                 655

Asn Trp Phe Asp Ile Ser Lys Trp Leu Trp Tyr Ile
            660                 665
```

IMMUNOGENIC COMPLEXES OF POLYANIONIC CARBOMERS AND ENV POLYPEPTIDES AND METHODS OF MANUFACTURE AND USE THEREOF

CROSS REFERENCE TO RELATED APPLICATION

This application is the U.S. National Phase of International Application No. PCT/US2012/065113, filed Nov. 14, 2012 and published in English, which claims the benefit of priority under 35 U.S.C. §119(e) to U.S. Provisional Application No. 61/559,512, filed Nov. 14, 2011. The disclosure of the above application is incorporated herein by reference in its entirety.

GOVERNMENT SUPPORT

This invention was made in part with U.S. Government support under HIVRAD grant 5P01 AI066287 awarded by the NIAID, NIH. The Government has certain rights in the invention.

TECHNICAL FIELD

Immunogenic compositions comprising complexes between polyanionic carbomers and Env polypeptides are described, as are uses of these immunogenic compositions and methods of forming and manufacturing such complexes. Immunogenic compositions comprising low viscosity, polyanionic carbomers and Env polypeptides are described, as are uses of these immunogenic compositions and methods of forming and manufacturing such compositions.

BACKGROUND

Acquired immune deficiency syndrome (AIDS) is recognized as one of the greatest health threats facing modern medicine. There is, as yet, no cure for this disease.

In 1983-1984, three groups independently identified the suspected etiological agent of AIDS. See, e.g., Barre-Sinoussi et al. (1983) Science 220:868-871; Montagnier et al., in Human T-Cell Leukemia Viruses (Gallo, Essex & Gross, eds., 1984); Vilmer et al. (1984) The Lancet 1:753; Popovic et al. (1984) Science 224:497-500; Levy et al. (1984) Science 225: 840-842. These isolates were variously called lymphadenopathy-associated virus (LAV), human T-cell lymphotropic virus type III (HTLV-III), or AIDS-associated retrovirus (ARV). All of these isolates are strains of the same virus, and were later collectively named Human Immunodeficiency Virus (HIV). With the isolation of a related AIDS-causing virus, the strains originally called HIV are now termed HIV-1 and the related virus is called HIV-2. See, e.g., Guyader et al. (1987) Nature 326:662-669; Brun-Vezinet et al. (1986) Science 233:343-346; Clavel et al. (1986) Nature 324:691-695.

A great deal of information has been generated about the HIV virus; however, to date an effective vaccine has not been identified. Several targets for vaccine development have been examined including the Env and Gag gene products encoded by HIV. Gag gene products include, but are not limited to, Gag-polymerase and Gag-protease. Env gene products include, but are not limited to, monomeric gp120 polypeptides, oligomeric gp140 polypeptides and gp160 polypeptides.

Use of HIV Env polypeptides in immunogenic compositions has been described. (see, e.g., U.S. Pat. No. 5,846,546 to Hurwitz et al., describing immunogenic compositions comprising a mixture of at least four different recombinant viruses that each expresses a different HIV env variant; and U.S. Pat. No. 5,840,313 to Vahlne et al., describing peptides which correspond to epitopes of the HIV-1 gp120 protein). In addition, U.S. Pat. No. 5,876,731 to Sia et al, describes candidate vaccines against HIV comprising an amino acid sequence of a T-cell epitope of Gag linked directly to an amino acid sequence of a B-cell epitope of the V3 loop protein of an HIV-1 isolate containing the sequence GPGR. However, none of these Env polypeptide base compositions has been shown to provide a sufficient protective immune response to be useful for an efficacious vaccine. Recently, G. Krashias et al. (Vaccine. 28:2482-2489, 2010) described a vaccine comprising gp140 and CARBOPOL™. G. Krashias et al. found that the CARBOPOL™ provided an improved immune response over alum as an adjuvant. However, G. Krashias et al. found no detectable binding between gp140 and CARBOPOL™.

SUMMARY

The inventors have surprisingly found that, under appropriate conditions, polyanionic carbomers can form complexes with Env polypeptides. The complexes show improved immunogenicity over existing adjuvanted HIV candidate vaccines.

Described herein are novel complexes between polyanionic carbomers and Env polypeptides. One aspect of the disclosure includes immunogenic compositions that comprise an Env polypeptide in complex with a polyanionic carbomer polymer. In one embodiment, the Env polypeptide is an HIV Env polypeptide or even an HIV-1 Env polypeptide. In another embodiment, which may be combined with the preceding embodiments, the polyanionic carbomer polymer is free of benzene. In another embodiment, which may be combined with the preceding embodiments, the concentration of the polyanionic carbomer polymer is between about 0.01% (w/v) and about 2.0% (w/v), between about 0.01% (w/v) and about 0.5% (w/v), or between about 0.01% (w/v) and about 0.2% (w/v). In another embodiment, which may be combined with the preceding embodiments, the polyanionic polymer comprises CARBOPOL 971P NF™, CARBOPOL 974P NF™, or combinations thereof, or preferably CARBOPOL 971P NF™. In yet another embodiment, which may be combined with the preceding embodiments, the Env polypeptide is trimeric. In certain embodiments which can be combined with the preceding embodiment, the Env polypeptide comprises one or more mutations. In certain embodiments which can be combined with the preceding embodiments with one or more mutations, the one or more mutations are selected from mutations in the cleavage site that prevents the cleavage of a gp140 polypeptide into a gp120 polypeptide and a gp41 polypeptide, mutations in the glycosylation site, deletion of the V1 region, deletion of the V2 region, and a combination of the foregoing. Preferably, the one or more mutations comprise a mutation in the cleavage site that prevents the cleavage of a gp140 polypeptide into a gp120 polypeptide and a gp41 polypeptide and deletion of the V2 region. In certain embodiments which can be combined with the preceding embodiments, the Env polypeptide includes a gp160 Env polypeptide or a polypeptide derived from a gp160 Env polypeptide; a gp140 Env polypeptide or a polypeptide derived from a gp140 Env polypeptide; or a gp120 Env polypeptide or a polypeptide derived from a gp120 Env polypeptide. In certain embodiments, the Env polypeptide comprises an amino acid sequence with at least 75% sequence identity, at least 80% sequence identity, at least 85% sequence identity, at least 90% sequence identity, at least 95% sequence identity, at least 97% sequence identity, at least 98% sequence identity, or at least 99% sequence identity to SEQ ID NOs: 22 or 23. In certain embodiments which can be combined with the preceding embodiments, the immunogenic compositions further include a second Env polypeptide selected from a different HIV subtype as the Env polypeptide. In certain embodiments which can be combined with the preceding embodiments which include a second Env polypeptide, the second Env polypeptide and the Env polypeptide are in mixed complexes the polyanionic carbomer polymer. In certain embodiments which can be combined with the preceding embodiments which include a second Env polypeptide, the second Env polypeptide is in a separate complex with a second polyanionic carbomer polymer or the polyanionic carbomer polymer and the second polyanionic carbomer polymer are the same type of polymer. In certain embodiments which can be combined with the preceding embodiments which include a second Env polypeptide, the Env polypeptide and the second Env polypeptide are derived from an HIV subtype B strain and an HIV subtype C strain or vice-versa. In certain embodiments which can be combined with the preceding embodiments, the immunogenic compositions further include one or more additional HIV polypeptides. In certain embodiments which can be combined with the preceding embodiments which include a one or more additional HIV polypeptides, the one or more additional HIV polypeptides are selected from the group comprising a Gag polypeptide, a Nef polypeptide, a Prot polypeptide, a Tat polypeptide, a Rev polypeptide, a Vif polypeptide, a Vpr polypeptide, and a Vpu polypeptide. In certain embodiments which can be combined with the preceding embodiments which include one or more additional HIV polypeptides, the one or more additional HIV polypeptides include mutations that reduce or eliminate the activity of the polypeptide without adversely affecting the ability of the additional HIV polypeptides to generate an immune response. In certain embodiments which can be combined with the preceding embodiments, the immunogenic complexes further include an adjuvant. In certain embodiments which can be combined with the preceding embodiments which include an adjuvant, the adjuvant is MF59.

Another aspect of the disclosure includes methods of generating the immunogenic compositions above by (a) contacting the polyanionic carbomer polymer with the Env polypeptide under conditions where the pH is below the pI of the Env polypeptide in a solution; (b) incubating the polyanionic carbomer polymer with the Env polypeptide together to allow the Env polypeptide to form a complex with the polyanionic carbomer polymer. In one embodiment, the Env polypeptide is an HIV Env polypeptide or even an HIV-1 Env polypeptide. In certain embodiments, which may be combined with the preceding embodiment, the pH is between 3 and 6; between 3 and 5; or between 3 and 4. In another embodiment, which may be combined with the preceding embodiments, the polyanionic carbomer polymer is free of benzene. In another embodiment, which may be combined with the preceding embodiment, the concentration of the polyanionic carbomer polymer after contacting step (a) is between about 0.01% (w/v) and about 2.0% (w/v), between about 0.01% (w/v) and about 0.5% (w/v), or between about 0.01% (w/v) and about 0.2% (w/v). In another embodiment, which may be combined with the preceding embodiments, the polyanionic polymer comprises CARBOPOL 971P NF™, CARBOPOL 974P NF™, or combinations thereof, or preferably CARBOPOL 971P NF™. In yet another embodiment, which may be combined with the preceding embodiments, the Env polypeptide is trimeric. In certain embodiments which can be combined with the preceding embodiments, the Env polypeptide comprises one or more mutations. In certain embodiments which can be combined with the preceding embodiments that include one or more mutations, the one or more mutations are selected from mutations in the cleavage site that prevents the cleavage of a gp140 polypeptide into a gp120 polypeptide and a gp41 polypeptide, mutations in the glycosylation site, deletion of the V1 region, deletion of the V2 region, and a combination of the foregoing. Preferably, the one or more mutations comprise a mutation in the cleavage site that prevents the cleavage of a gp140 polypeptide into a gp120 polypeptide and a gp41 polypeptide and deletion of the V2 region. In certain embodiments which can be combined with the preceding embodiments, the Env polypeptide includes a gp160 Env polypeptide or a polypeptide derived from a gp160 Env polypeptide; a gp140 Env polypeptide or a polypeptide derived from a gp140 Env polypeptide; or a gp120 Env polypeptide or a polypeptide derived from a gp120 Env polypeptide. In certain embodiments which can be combined with the preceding embodiments, the Env polypeptide comprises an amino acid sequence with at least 75% sequence identity, at least 80% sequence identity, at least 85% sequence identity, at least 90% sequence identity, at least 95% sequence identity, at least 97% sequence identity, at least 98% sequence identity, or at least 99% sequence identity to SEQ ID NOs: 22 or 23. In certain embodiments which can be combined with the preceding embodiments, a second Env polypeptide is added that is selected from a different HIV subtype as the Env polypeptide to the solution. In certain embodiments which can be combined with the preceding embodiments that include a second Env polypeptide, the second Env polypeptide is incubated with the polyanionic carbomer polymer with the Env polypeptide to allow the Env polypeptide and the second Env polypeptide to form complexes with the polyanionic carbomer polymer simultaneously. In certain embodiments which can be combined with the preceding embodiments that include a second Env polypeptide, the second Env polypeptide is in a separate complex with a second polyanionic carbomer polymer. In certain embodiments which can be combined with the preceding embodiments that include a second polyanionic carbomer polymer, the polyanionic carbomer polymer and the second polyanionic carbomer polymer are the same type of polymer. In certain embodiments which can be combined with the preceding embodiments that include a second Env polypeptide, the Env polypeptide and the second Env polypeptide are derived from an HIV subtype B strain and an HIV subtype C strain or vice-versa. In certain embodiments which can be combined with the preceding embodiments, the method further includes a step of adding one or more additional HIV polypeptides. In certain embodiments which can be combined with the preceding embodiments that include one or more additional HIV polypeptides, the one or more additional HIV polypeptides are selected from the group comprising a Gag polypeptide, a Nef polypeptide, a Prot polypeptide, a Tat polypeptide, a Rev polypeptide, a Vif polypeptide, a Vpr polypeptide, and a Vpu polypeptide. In certain embodiments which can be combined with the preceding embodiments that include one or more additional HIV polypeptides, the one or more additional HIV polypeptides include mutations that reduce or eliminate the activity of the polypeptide without adversely affecting the ability of the additional HIV polypeptides to generate an immune response. In certain embodiments which can be combined with the preceding embodiments, the method further includes a step of adding an adjuvant to the solution. In certain embodiments which can be combined with the preceding embodiments that include an adjuvant, the adjuvant is MF59.

Yet another aspect of the disclosure includes methods of generating an immune response in a subject, comprising administering to said subject an immunogenic composition according to the preceding composition aspect or generated by the method according to the preceding method aspect, thereby generating the immune response to the Env polypeptide. In one embodiment, the immunogenic composition is administered intramuscularly, intramucosally, intranasally, subcutaneously, intradermally, transdermally, intravaginally, intrarectally, orally or intravenously. In certain embodiments which can be combined with the preceding embodiment, the subject is a mammal. Preferably, the mammal is a human. In certain embodiments which can be combined with the preceding embodiments, the immune response includes a humoral immune response. In certain embodiments which can be combined with the preceding embodiments, the immune response includes a cellular immune response.

Still another aspect of the disclosure includes methods of generating an enhanced immune response in a subject by (a) transfecting cells of said subject with a gene delivery vector for expression of an Env polypeptide, under conditions that permit the expression of the Env polypeptide, thereby generating an immune response to the Env polypeptide; (b) administering to said subject an immunogenic composition according to the preceding composition aspect or generated by the method according to the preceding method aspect, thereby enhancing the immune response to the Env polypeptide.

Another aspect of the disclosure includes methods of generating an enhanced immune response in a subject previously having had a gene delivery vector for expression of an Env polypeptide transfected into cells of the subject under conditions that permitted the expression of the Env polypeptide thereby having generated an immune response to the Env polypeptide, comprising administering to said subject an immunogenic composition according to an immunogenic composition according to the preceding composition aspect or generated by the method according to the preceding method aspect, thereby enhancing the immune response to the Env polypeptide. In one embodiment, the immunogenic composition is administered intramuscularly, intramucosally, intranasally, subcutaneously, intradermally, transdermally, intravaginally, intrarectally, orally or intravenously. In certain embodiments which can be combined with the preceding embodiment, the subject is a mammal. Preferably, the mammal is a human. In certain embodiments which can be combined with the preceding embodiments, the immune response includes a humoral immune response. In certain embodiments which can be combined with the preceding embodiments, the immune response includes a cellular immune response.

Described herein are novel compositions inclusing low viscosity, polyanionic carbomers and Env polypeptides. One aspect of the disclosure includes immunogenic compositions that comprise an Env polypeptide with a low viscosity, polyanionic carbomer polymer. In one embodiment, the Env polypeptide is an HIV Env polypeptide or even an HIV-1 Env polypeptide. In another embodiment, which may be combined with the preceding embodiments, the polyanionic carbomer polymer is free of benzene. In another embodiment, which may be combined with the preceding embodiments, the concentration of the polyanionic carbomer polymer is between about 0.01% (w/v) and about 2.0% (w/v), between about 0.01% (w/v) and about 0.5% (w/v), or between about 0.01% (w/v) and about 0.2% (w/v). In another embodiment, which may be combined with the preceding embodiments, the low viscosity, polyanionic polymer comprises a polyanionic polymer with an average viscosity of less than 25,000 cP (25° C., Brookfield RVT, 20 rpm, neutralized to pH 7.3-7.8, 0.5 wt % mucilage, spindle #6), less than 20,000 cP, less than less than 15,000 cP, or the low viscosity, polyanionic polymer is CARBOPOL 971P NF™. In yet another embodiment, which may be combined with the preceding embodiments, the Env polypeptide is trimeric. In certain embodiments which can be combined with the preceding embodiment, the Env polypeptide comprises one or more mutations. In certain embodiments which can be combined with the preceding embodiments with one or more mutations, the one or more mutations are selected from mutations in the cleavage site that prevents the cleavage of a gp140 polypeptide into a gp120 polypeptide and a gp41 polypeptide, mutations in the glycosylation site, deletion of the V1 region, deletion of the V2 region, and a combination of the foregoing. Preferably, the one or more mutations comprise a mutation in the cleavage site that prevents the cleavage of a gp140 polypeptide into a gp120 polypeptide and a gp41 polypeptide and deletion of the V2 region. In certain embodiments which can be combined with the preceding embodiments, the Env polypeptide includes a gp160 Env polypeptide or a polypeptide derived from a gp160 Env polypeptide; a gp140 Env polypeptide or a polypeptide derived from a gp140 Env polypeptide; or a gp120 Env polypeptide or a polypeptide derived from a gp120 Env polypeptide. In certain embodiments, the Env polypeptide comprises an amino acid sequence with at least 75% sequence identity, at least 80% sequence identity, at least 85% sequence identity, at least 90% sequence identity, at least 95% sequence identity, at least 97% sequence identity, at least 98% sequence identity, or at least 99% sequence identity to SEQ ID NOs: 22 or 23. In certain embodiments which can be combined with the preceding embodiments, the immunogenic compositions further include a second Env polypeptide selected from a different HIV subtype as the Env polypeptide. In certain embodiments which can be combined with the preceding embodiments which include a second Env polypeptide, the Env polypeptide and the second Env polypeptide are derived from an HIV subtype B strain and an HIV subtype C strain or vice-versa. In certain embodiments which can be combined with the preceding embodiments, the immunogenic compositions further include one or more additional HIV polypeptides. In certain embodiments which can be combined with the preceding embodiments which include a one or more additional HIV polypeptides, the one or more additional HIV polypeptides are selected from the group comprising a Gag polypeptide, a Nef polypeptide, a Prot polypeptide, a Tat polypeptide, a Rev polypeptide, a Vif polypeptide, a Vpr polypeptide, and a Vpu polypeptide. In certain embodiments which can be combined with the preceding embodiments which include one or more additional HIV polypeptides, the one or more additional HIV polypeptides include mutations that reduce or eliminate the activity of the polypeptide without adversely affecting the ability of the additional HIV polypeptides to generate an immune response. In certain embodiments which can be combined with the preceding embodiments, the immunogenic compositions further include an adjuvant. In certain embodiments which can be combined with the preceding embodiments which include an adjuvant, the adjuvant is MF59.

Yet another aspect of the disclosure includes methods of generating an immune response in a subject, comprising administering to said subject an immunogenic composition according to the preceding composition aspect, thereby generating the immune response to the Env polypeptide. In one embodiment, the immunogenic composition is administered intramuscularly, intramucosally, intranasally, subcutaneously, intradermally, transdermally, intravaginally, intrarectally, orally or intravenously. In certain embodiments which can be combined with the preceding embodiment, the subject is a mammal. Preferably, the mammal is a human. In certain embodiments which can be combined with the preceding embodiments, the immune response includes a humoral immune response. In certain embodiments which can be combined with the preceding embodiments, the immune response includes a cellular immune response.

Still another aspect of the disclosure includes methods of generating an enhanced immune response in a subject by (a) transfecting cells of said subject with a gene delivery vector for expression of an Env polypeptide, under conditions that permit the expression of the Env polypeptide, thereby generating an immune response to the Env polypeptide; (b) administering to said subject an immunogenic composition according to the preceding composition aspect, thereby enhancing the immune response to the Env polypeptide.

Another aspect of the disclosure includes methods of generating an enhanced immune response in a subject previously having had a gene delivery vector for expression of an Env polypeptide transfected into cells of the subject under conditions that permitted the expression of the Env polypeptide thereby having generated an immune response to the Env polypeptide, comprising administering to said subject an immunogenic composition according to an immunogenic composition according to the preceding composition aspect, thereby enhancing the immune response to the Env polypeptide. In one embodiment, the immunogenic composition is administered intramuscularly, intramucosally, intranasally, subcutaneously, intradermally, transdermally, intravaginally, intrarectally, orally or intravenously. In certain embodiments which can be combined with the preceding embodiment, the subject is a mammal. Preferably, the mammal is a human. In certain embodiments which can be combined with the preceding embodiments, the immune response includes a humoral immune response. In certain embodiments which can be combined with the preceding embodiments, the immune response includes a cellular immune response.

BRIEF DESCRIPTION OF THE FIGURES

FIG. 7A shows the neutralization potentials against Tier 1a and Tier 1b isolates. FIG. 7B shows the neutralization potentials against Tier 2 isolates and the control.

FIGS. 8A-B show a heat map that shows the breadth and potency (ID50 titers) of serum neutralization of HIV-1 pseudoviruses. The results from each of the five rabbits in each group are shown. Samples in black demonstrated 50% neutralization with a serum dilution from 1,000 to 9,999; samples in dark grey demonstrated 50% neutralization with a serum dilution from 100 to 999; and samples shaded in light grey demonstrated 50% neutralization with a serum dilution from 20 to 99. FIG. 8A shows the breadth and potency against Tier 1a and Tier 1b isolates. FIG. 8B shows the breadth and potency against Tier 2 isolates.

FIG. 9A shows the neutralization ID50 titers of against two Tier 1a isolates (2wp3 (p3), 2wp4 (p4), & 2wp5 (p5)): MW965.26 (a subtype C) and SF162.LS (a subtype B). FIG. 9B shows the neutralization ID50 titers of against another Tier 1a isolate (2wp3 (p3), 2wp4 (p4), & 2wp5 (p5)): MN (a subtype B). FIG. 9C shows the neutralization ID50 titers of against two Tier 1b isolates (2wp3 (p3), 2wp4 (p4), & 2wp5 (p5)): Ba1.26 (a subtype C) and TV1.21 (a subtype B). FIG. 9D shows the neutralization ID50 titers of against two Tier 2 isolates (2wp3 (p3), 2wp4 (p4), & 2wp5 (p5)): ZM249M.PL1 (a subtype C) and Du156.12 (a subtype C). FIG. 9E shows the neutralization ID50 titers of against another Tier 2 isolate (2wp3 (p3), 2wp4 (p4), & 2wp5 (p5)): Du422.1 (a subtype C).

FIG. 12A-B shows a heat map that shows the breadth and potency (ID50 titers) of serum neutralization of HIV-1 pseudoviruses using serum collected at two-weeks post third immunization. Samples in black demonstrated 50% neutralization with a serum dilution of greater than 10,000; samples in dark grey with white colored numbers demonstrated 50% neutralization with a serum dilution of 1,000 to 9,999; samples in dark grey demonstrated 50% neutralization with a serum dilution from 100 to 999; and samples shaded in light grey demonstrated 50% neutralization with a serum dilution from 20 to 99.

FIG. 13A-C shows a heat map that shows the breadth and potency (ID50 titers) of serum neutralization of HIV-1 pseudoviruses using serum collected at two-weeks post fourth immunization for an extended panel of strains. Samples in black demonstrated 50% neutralization with a serum dilution from 1,000 to 9,999; samples in dark grey demonstrated 50% neutralization with a serum dilution from 100 to 999; and samples shaded in light grey demonstrated 50% neutralization with a serum dilution from 20 to 99.

FIG. 14A shows neutralization titers against two Tier 1A isolates: MW965.26 (subtype C) (left) and SF162.LS (subtype B) (right). FIG. 14B shows neutralization titers against a third Tier 1A isolate: MN.2 (subtype B). FIG. 14C shows neutralization titers against two Tier 1B isolates: Ba1.26 (subtype B) (left) and TV1.21 (subtype C) (right). FIG. 14D shows neutralization titers against two Tier 2 isolates: ZM249M.PL1 (subtype C) (left) and Du165.12 (subtype C) (right). FIG. 14E shows neutralization titers against a third Tier 2 isolate: Du422.1 (subtype C).

FIGS. 17A-F show neutralization potential (ID50 titers, y-axis) of the antibodies induced by immunization with each of the ten gp120 Env polypeptide and the sequential immunization experiment against a panel of virus isolates (x-axis). FIG. 17A shows the neutralization potential (in ID50 titers) of Du156.12 gp120 (left) and Du422.1 gp120 (right). FIG. 17B shows the neutralization potential (in ID50 titers) of ZM249M.PL1 gp120 (left) and CAP45 (EF203960) gp120 (right). FIG. 17C shows the neutralization potential (in ID50 titers) of CAP84 (EF203963) gp120 (left) and CAP239 (EF203983) gp120 (right). FIG. 17D shows the neutralization potential (in ID50 titers) of TV1 gp120 (left) and SF162 gp120 (right). FIG. 17E shows the neutralization potential (in ID50 titers) of TV1 gp140 (left) and SF162 gp140 (right). FIG. 17F shows the neutralization potential (in ID50 titers) of the sequential immunization with CAP239 gp120, Du422.1 gp120, ZM249.PL1 gp120, and TV1 gp120s (left) and all of the groups tested on a single chart (right).

FIG. 18A-B show a heat map that shows the breadth and potency (ID50 titers) of serum neutralization of HIV-1 pseudoviruses using serum collected at two-weeks post third immunization. Samples in dark grey demonstrated 50% neutralization with a serum dilution >10000; and samples shaded in light grey demonstrated 50% neutralization with a serum dilution from 1000 to 9,999.

FIG. 19 shows results of monoclonal antibodies (mAbs) competition ELISA conducted against immobilized TV1gp140 Env polypeptide with pooled rabbit sera (1:100 dilution) collected 2 weeks post fourth immunization with subtype C gp120 (week 22), in order to map epitope specificities of anti-Env antibodies elicited upon immunization. The isolates of Env polypeptides tested are shown at the top. The epitope and mAbs used in the competition assay are shown along the left.

FIGS. 20A-F show neutralization potential (ID50 titers, y-axis) of the antibodies induced by immunization of guinea pigs with each of the ten constructs against a panel of virus isolates (x-axis). FIG. 20A shows the neutralization potential (in ID50 titers) of Du156.12 gp120 (left) and Du422.1 gp120 (right). FIG. 20B shows the neutralization potential (in ID50 titers) of ZM249M.PL1 gp120 (left) and CAP45 (EF203960) gp120 (right). FIG. 20C shows the neutralization potential of CAP84 (EF203963) gp120 (left) and the CAP239 (EF203983) gp120 (right). FIG. 20D shows the neutralization potential (in ID50 titers) of TV1 gp120 (left) and SF162 gp120 (right). FIG. 20E shows the neutralization potential (in ID50 titers) of TV1 gp140 (left) and SF162 gp140 (right). FIG. 20D shows the neutralization potential of all of the groups tested on a single chart.

FIG. 21 shows a heat map that shows the breadth and potency (in ID50 titers) of serum neutralization of HIV-1 pseudoviruses using serum collected at two-weeks post third immunization. Samples in dark grey demonstrated 50% neutralization with a serum dilution >10000; and samples shaded in light grey demonstrated 50% neutralization with a serum dilution from 1000 to 9,999.

FIG. 22 shows results of monoclonal antibodies (mAbs) competition ELISA conducted against immobilized TV1 gp140 Env polypeptide with pooled sera (1:500 dilution) collected 2 weeks post third immunization (week 14) from the guinea pig study of Example 10, in order to map epitope specificities of anti-Env antibodies elicited upon immunization. The isolates of Env polypeptides tested are shown at the top. The epitope and mAbs used in the competition assay are shown along the left.

FIG. 23 shows results of monoclonal antibodies (mAbs) competition ELISA conducted against immobilized TV1 gp140 Env polypeptide with pooled sera (1:500 dilution) collected 2 weeks post fourth immunization (week 26) from the guinea pig study of Example 10, in order to map epitope specificities of anti-Env antibodies elicited upon immunization. The isolates of Env polypeptides tested are shown at the top. The epitope and mAbs used in the competition assay are shown along the left.

FIG. 24A shows rabbits 1-5. FIG. 24B shows rabbits 6-10. FIG. 24C shows rabbits 11-15. FIG. 24D shows rabbits 16-20. FIG. 24E shows rabbits 21-25. FIG. 24F shows rabbits 26-30. FIG. 24G shows rabbits 31-35. FIG. 24H shows rabbits 36-40. FIG. 24I shows rabbits 41-45. FIG. 24J shows rabbits 46-50. FIG. 24K shows rabbits 51-55.

DETAILED DESCRIPTION OF THE PREFERRED EMBODIMENTS

Figure 1:
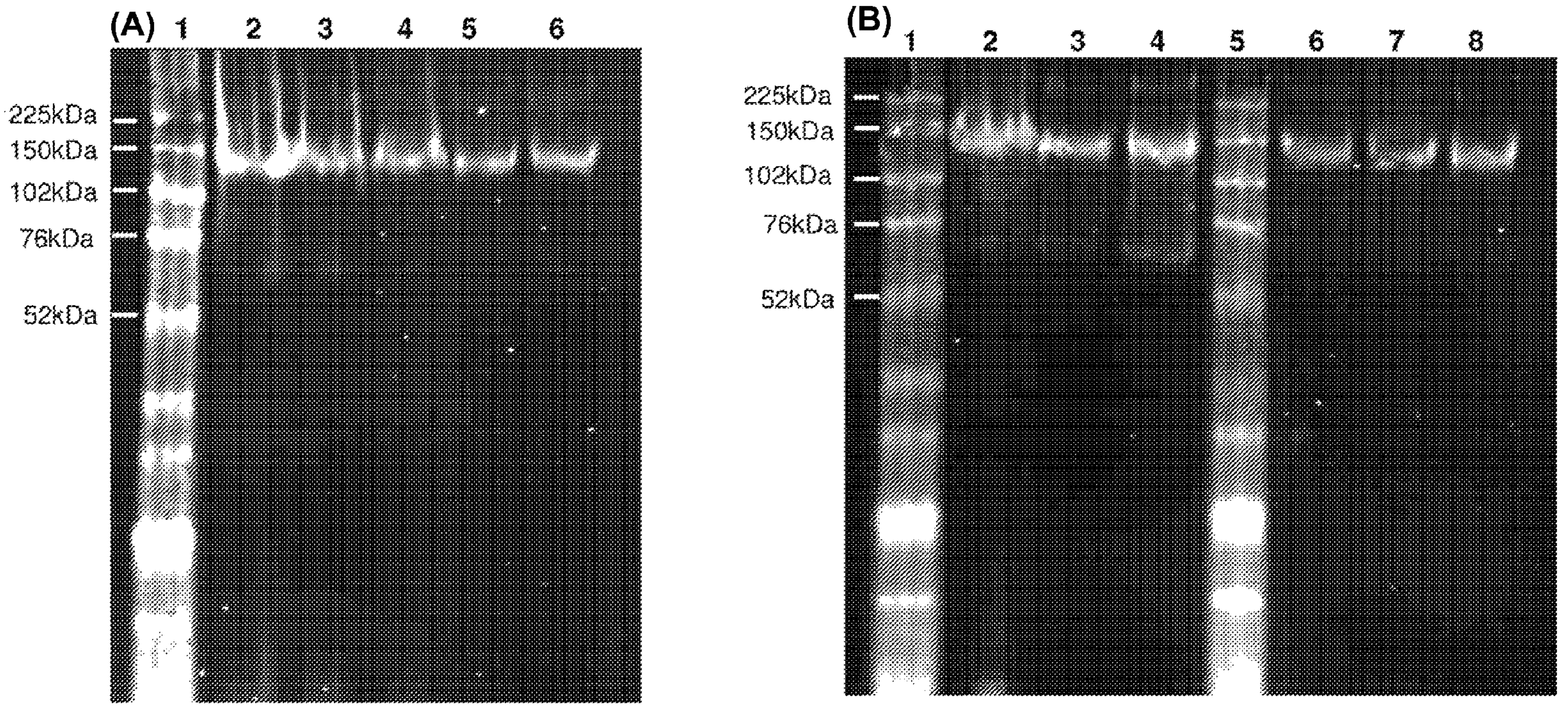
FIG. 1 shows immunoblots of the Env polypeptide-CARBOPOL™ complexes after incubation for various periods of time. Panel (A) shows from left to right (1) molecular weight markers, (2) Env polypeptide complex—0 hours, (3) Env polypeptide complex—1 hour at 4° C., (4) Env polypeptide complex—2 hours at 4° C., (5) Env polypeptide complex—3 hours at 4° C., and (6) Env polypeptide complex—4 hours at 4° C. Panel (B) shows from left to right (1) molecular weight markers, (2) Env polypeptide complex—1 hour at 4° C., (3) Env polypeptide complex—1 hour at 20° C., (4) Env polypeptide in PBS—1 hour at room temperature (25° C.), (5) molecular weight markers, (6) Env polypeptide complex—1 hour at 30° C., (7) Env polypeptide complex—1 hour at 37° C., and (8) Env polypeptide in PBS—1 hour at 37° C. The final concentration of CARBOPOL™ in the gels was ~0.1%.

HIV-1 envelope glycoprotein (Env) is the major viral protein exposed to humoral immune response so it is an important target for vaccine development. Eliciting potent anti-HIV-1 neutralizing antibodies using Env has been complicated by various factors. A key factor is the antigenic variation and structural complexity of Env. Recombinant Env glycoproteins have shown sub-optimal immunogenicity in the absence of an adjuvant. Therefore, in addition to optimizing the design of Env-immunogens, identification of novel adjuvants and/or delivery systems is important in generating vaccine-mediated protective immune response against HIV.

Since Env is particularly labile and has conformation-dependent neutralization epitopes, adjuvants that do not denature or adversely modify the antigenic structure are preferable. The following examples demonstrate that cross-linked, polyacrylic acid polymers (polyanionic carbomers or CARBOPOL™) elicit a robust immune response when used in complex with Env polypeptides. Polyacrylic acid polymers are especially advantageous in that they can be combined with other adjuvants such as MF59™ to even further improve the immune response. Importantly, the examples show an improvement in overall breadth and potency of neutralizing antibodies when using polyanionic carbomers along with MF59™. Overall, the examples confirm that polyanionic carbomers can form complexes with Env without altering the antigenic structure or stability of the polypeptide and that the complexes elicit better immune response upon vaccination alone or in combination with other adjuvants such as MF59™. While not limiting to theory, the improved immune response could be due to the polyanionic carbomers directing or presenting the Env polypeptide to specific cells in the immune system and/or the polyanionic carbomers stabilizing the Env polypeptides during storage and after vaccination. In addition, the Env polypeptide can be adjuvanted with low viscosity, polyanionic polymers with an average viscosity of less than 25,000 cP (25° C., Brookfield RVT, 20 rpm, neutralized to pH 7.3-7.8, 0.5 wt % mucilage, spindle #6), less than 20,000 cP, less than less than 15,000 cP. A preferred example of such low viscosity, polyanionic polymers is CARBOPOL 971P NF™.

The practice of the disclosed compositions and methods will only require, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Short Protocols in Molecular Biology, 4th ed. (Ausubel et al. eds., 1999, John Wiley & Sons); Molecular Biology Techniques: An Intensive Laboratory Course, (Ream et al., eds., 1998, Academic Press); PCR (Introduction to Biotechniques Series), 2nd ed. (Newton & Graham eds., 1997, Springer Verlag).

Polyanionic Carbomer Polymers

The polyanionic carbomer polymers to be used in the compositions and methods disclosed herein are acrylic acid polymers. These acrylic acid polymers may be homopolymers or copolymers. Polyanionic carbomer polymers are commercially available under the trade name CARBOPOL™. Acrylic acid polymers are described, for example, in U.S. Pat. Nos. 2,909,462 and 3,790,665.

While there are many polyanionic carbomer polymers to choose from which will form the complexes that have improved immunogenicity, the preferred polyanionic carbomer polymers are those with lesser crosslinking and which are not formed in the presence of benzene so as to avoid residual benzene (a potentially more toxic organic compound). Based upon the preferred characteristics, CARBOPOL 971P NF™ polymer was selected as it had residual ethyl acetate solvent (a class III solvent according to ICH guidelines) rather than benzene. We also considered 974P NF, which is chemically similar and has more toxicology and other supportive data showing that it is safe, but since it is a cross linked polyacrylic acid of very high molecular weight, we decided to choose 971P NF since it was a comparatively lightly cross-linked polymer and could aid solvation. Since regulatory and toxicological information are available for 974P NF, and they are likely applicable to 971P NF, we were satisfied to choose the later in our studies.

The molecular weight range of these polymers depending upon the polymer is estimated to be from 740,000 to 4-5 million Daltons. There are no methods available to measure the actual molecular weight of a cross-linked (i.e., 3-dimensional) polymer of this type, so the size must be estimated by other means such as dynamic light scattering, etc. The backbone of the homopolymer is the same, i.e., polymerized acrylic acid. The main differences relate to cross-link density and estimated molecular weight, rather than the cross-linker used. With very minor adjustments in the cross-linker density, one can produce a large number of polyanionic carbomer polymers similar in gross molecular structure but varying in application properties, for example, viscosity. Cross-link density can be varied by minor shifts in position of the cross-linker on the acrylic backbone. Because the actual cross-linker itself has little, if any, effect on the biological properties of a particular acrylic acid polymer, the Cosmetic, Toiletries and Fragrance Association (CTFA) has adapted a family monograph, "carbomer," for these polymers.

Polyanionic carbomer polymers, such as CARBOPOL™, PEMULEN™ and NOVEON™, are polymers within the scope of the invention. These particular polyanionic carbomer polymers are cross-linked with polyalkenyl ethers or divinyl glycol.

Polyanionic carbomer polymers are flocculated powders of particles averaging about 0.2 micron in diameter. Each particle can be viewed as a network structure of polymer chains interconnected by crosslinks. Without the crosslinks, the primary particle would be a collection of linear polymer chains, intertwined but not chemically bonded. These linear polymers are soluble in a polar solvent, such as water. In water, polyanionic carbomer polymers swell up to 1000 times their original volume (and ten times their original diameter) to form a gel when exposed to a pH environment above 4-6. Since the pKa of these polymers is 6±0.5, the carboxylate groups on the polymer backbone ionize, resulting in repulsion between the negative particles, which adds to the swelling of the polymer. Cross-linked polymers do not dissolve in water.

Characteristics of Specific Types of Polyanionic Carbomer Polymers:

CARBOPOL 934 P™ is cross-linked with allyl sucrose and is polymerized in solvent benzene. CARBOPOL 971 P™ (71G, 974 P) are cross-linked with allyl penta erythritol and polymerized in ethyl acetate. Polycarbophil is cross-linked polymer in divinyl glycol and polymerized in solvent benzene. All the polymers fabricated in ethyl acetate are neutralized by 1-3% potassium hydroxide. Though CARBOPOL 971 P™ and CARBOPOL 974 P™ are manufactured by same process under similar conditions; the difference in them is that CARBOPOL 971 P™ has slightly lower level of cross-linking agent than CARBOPOL 974 P™. CARBOPOL 71 G™ is the granular form of CARBOPOL™.

While the relationships between structure and properties have been of interest both academically and in industry. Different grades of polyanionic carbomer polymers exhibit different rheological properties, a reflection of the particle size, molecular weight between crosslinks (Mc), distributions of the Mc, and the fraction of the total units, which occur as terminal, i.e. free chain ends. The molecular weights between adjacent crosslinks (Mc) are approximately inversely proportional to the crosslinker density. These may be calculated from the functionality of the crosslinking monomer, the relative ratio of acrylic acid to crosslinking monomer, and the efficiency of the crosslinking reaction, assuming negligible chain ends. Alternatively, the molecular weight can be qualitatively compared to the rheological properties of a swollen gel and/or from the equilibrium-swelling ratio. In simple terms, low viscosity, low rigidity polymer, such as CARBOPOL 971 P™, have a higher Mc. Conversely, they have lower crosslinker densities. The higher the crosslinker level, the lower the equilibrium swelling ratio. In the network theory of elasticity, the elastic modulus, G, is inversely proportional to the molecular weight between crosslinks (Mc).

CARBOPOL 971 P™ provides very low viscosities and excellent yield values at low usage levels. Suspensions formed with CARBOPOL 971 P™ will have longer rheology. CARBOPOL 71 G™ polymers will give same viscosities and rheology as CARBOPOL 971 P™, but it is easier to handle and disperse due to its granular nature.

Toxicity Details:

The polyanionic carbomer polymers, like other high molecular weight polymers, demonstrate a low toxic and irritation potential based on their physical and chemical properties. Accordingly, such cross-linked, high molecular weight acrylic acid polymers have been found safe for use in a wide variety of cosmetics, detergents and pharmaceuticals by appropriate regulatory and nonregulatory bodies concerned with such products.

Carbomer is the generic (i.e., nonproprietary) name adopted by USP-NF, United States Adopted Names Council (USAN) and CTFA for various CARBOPOL™ polymers. The Cosmetic Ingredient Review (CIR) Expert Panel in their assessment of the safety of the carbomers for cosmetic ingredients summarized the toxicity of the carbomers as follows: Acute oral studies with rats, guinea pigs, mice, and dogs showed that carbomers 910, −934, −940 and −941 have low toxicities when ingested. The inhalation $LC_{50}$ of carbomer 910 in albino rats was 1.71 mg/l. The dermal $LC_{50}$ of rats exposed to carbomer 910 was greater than 3.0 g/kg. No mortalities occurred in rabbits injected intravenously with 1%, 2% or 3% carbomer 934 in aqueous solution at a dose of 5 ml/kg. Rabbits showed minimal skin irritation when tested with 100% carbomer 910 or −934, and zero to moderate eye irritation when tested with carbomers 910, −934, −934P, −940, −941, and/or their various salts at concentrations of 0.20-100%. Subchronic feeding of rats with doses up to 5.0 g/kg/day carbomer 934 (49 days) and of rats and dogs with up to 5.0% carbomer 934P in the diet (21 and/or 90 days) resulted in lower than normal body weights. In rats fed carbomer 934P at dietary levels of 5.0% for 90 days, absolute liver weights and liver to body and brain weight ratios were reduced, but no pathological changes were observed. One of skill in the art can readily take such issues into account when selecting which polyanionic carbomer polymer to use in the compositions and methods disclosed herein.

Clinical studies with carbomer 934 (CARBOPOL 934™) and its various salts showed that these polymers have low potential for skin irritation and sensitization at concentrations of 0.5%, 5.0%, 10.0%, and 100%. When tested on humans at 1.0% concentration, carbomers 940, −941, and their various salts also demonstrated low potential for skin irritation and sensitization. Further, formulations containing up to 0.25% carbomer 934 demonstrated low potential for human skin irritation, sensitization, phototoxicity, and photo-contact allergenicity. Clinical data for assessing the skin irritation and sensitization potential of carbomer 940 and −941 were limited to studies in which concentrations of only 1.0% were tested. Clinical data for assessing phototoxicity and photocontact allergenicity were limited to formulation studies in which concentrations of only 0.25% carbomer 934 were tested.

The CIR Expert Panel called attention to the presence of benzene as an impurity in the carbomers and recommended efforts to reduce it to the lowest possible level. In pursuit of this goal, Lubrizol Advanced Materials, Inc. has developed new CARBOPOL™ polymers which use alternate polymerization solvent systems (e.g. ethyl acetate, cyclohexane, etc.). Thus, it is preferred to use polyanionic carbomer polymers such as CARBOPOL 971P NF™ that were not formed in the presence of benzene. These polyanionic carbomer polymers are chemically identical to the benzene polymerized polyanionic carbomer polymers and are therefore listed on the U.S. Environmental Protection Agency's TSCA inventory as acrylic acid polymers or acrylic acid copolymers.

Preliminary toxicity test results on the ethyl acetate polymerized polymers are essentially similar to the previous products. They are not primary irritants or sensitizers in human repeated patch tests. The dermal LD50 was greater than 2000 mg/kg of body weight in the rabbit. Likewise it was minimally irritating to rabbit eyes. An acute oral LD50 could not be obtained since intubation of enough polymer was not possible. Results on a polyanionic carbomer polymers made in ethyl acetate were consistent with the results expected for these polymers. That is, it was not an irritant to rabbit skin; undiluted polymer was a mild to moderate irritant to the rabbit eyes, while a 1% solution (neutralized and unneutralized) were not eye irritants; application to human skin did not cause any skin irritation or sensitization. The LD50 in rats is greater than 5,000 mg/kg and the dermal LD50 in rabbits is greater than 2,000 mg/kg.

Given the similarity in the physical properties and structure of polyanionic carbomer polymers, one of skill in the art would recognize that any polyanionic carbomer polymer will produce similar results as CARBOPOL 971P NF™. Therefore, one of skill in the art could readily select from any number of available polyanionic carbomer polymers to produce the surprising result obtained herein based upon the foregoing.

When selecting a low viscosity, polyanionic polymer the average viscosity will be less than 25,000 cP (25° C., Brookfield RVT, 20 rpm, neutralized to pH 7.3-7.8, 0.5 wt % mucilage, spindle #6), less than 20,000 cP, or less than less than 15,000 cP. A preferred example of a low viscosity, polyanionic polymer is CARBOPOL 971P NF™.

Env Polypeptides

Env polypeptides include molecules derived from an envelope protein, preferably from HIV Env. The envelope protein of HIV-1 is a glycoprotein of about 160 kDa (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides. Env polypeptides can exist as monomers or trimers.

Env polypeptides include molecules derived from the gp120 region of the Env polypeptide. The primary amino acid sequence of gp120 is approximately 511 amino acids, with a polypeptide core of about 60,000 Daltons. The polypeptide is extensively modified by N-linked glycosylation to increase the apparent molecular weight of the molecule to 120,000 Daltons. The amino acid sequence of gp120 (and therefore gp140 and gp160) contains five relatively conserved domains interspersed with five hypervariable domains. The positions of the 18 cysteine residues in the gp120 primary sequence of the HIV-$1_{HXB-2}$ strain, and the positions of 13 of the approximately 24 N-linked glycosylation sites in the gp120 sequence are common to most, if not all, gp120 sequences. The hypervariable domains contain extensive amino acid substitutions, insertions and deletions. Despite this variation, most, if not all, gp120 sequences preserve the virus's ability to bind to the viral receptor CD4.

Env polypeptides (e.g., gp120, gp140 and gp160) include a "bridging sheet" comprised of 4 anti-parallel β-strands (β-2, β-3, β-20 and β-21) that form a β-sheet. Extruding from one pair of the β-strands (β-2 and β-3) are two loops, V1 and V2. The β-2 sheet occurs at approximately amino acid residue 113 (Cys) to amino acid residue 117 (Thr) while β-3 occurs at approximately amino acid residue 192 (Ser) to amino acid residue 194 (Ile), relative to SF-162. The "V1/V2 region" occurs at approximately amino acid positions 120 (Cys) to residue 189 (Cys), relative to SF-162. (see, e.g., Wyatt et al. (1995) J. Virol. 69:5723-5733; Stamatatos et al. (1998) J. Virol. 72:7840-7845). Extruding from the second pair of β-strands (β-20 and β-21) is a "small-loop" structure, also referred to herein as "the bridging sheet small loop." The locations of both the small loop and bridging sheet small loop can be determined relative to HXB-2 following the teachings herein and in WO00/39303. Table 1 provides a list of synthetic genes encoding representative Env polypeptide based upon the SF162 strain and the corresponding SEQ ID NOs.

TABLE 1

Exemplary Synthetic Env Polypeptide Expression Cassettes (SF162)

| Expression Cassette | Seq Id | Description |
|---|---|---|
| gp120 SF162 | 1 | wild-type |
| gp140 SF162 | 2 | wild-type |
| gp160 SF162 | 3 | wild-type |
| gp120.modSF162 | 4 | none |
| gp120.modSF162.delV2 | 5 | deleted V2 loop |
| gp120.modSF162.delV1/V2 | 6 | deleted V1 and V2 |
| gp140.modSF162 | 7 | none |
| gp140.modSF162.delV2 | 8 | deleted V2 loop |
| gp140.modSF162.delVl/V2 | 9 | deleted V1 and V2 |
| gp140.mut.modSF162 | 10 | mutated cleavage site |
| gp140.mut.modSF162.delV2 | 11 | deleted V2; mutated cleavage site |
| gp140.mut.modSF162.delV1/V2 | 12 | deleted V1 & V2; mutated cleavage site |
| gp140.mut7.modSF162 | 13 | mutated cleavage site |
| gp140.mut7.modSF162.delV2 | 14 | mutated cleavage site; deleted V2 |
| gp140.mut7.modSF162.delV1/V2 | 15 | mutated cleavage site; deleted V1 and V2 |
| gp140.mut8.modSF162 | 16 | mutated cleavage site |
| gp140.mut8.modSF162.delV2 | 17 | mutated cleavage site; deletedV2 |
| gp140.mut8.modSF162.delV1/V2 | 18 | mutated cleavage site; deleted V1 and V2 |
| gp160.modSF162 | 19 | none |
| gp160.modSF162.delV2 | 20 | deleted V2 loop |
| gp160.modSF162.delV1/V2 | 21 | deleted V1 & V2 |
| TV1 polypeptide | 22 | |
| SF162 polypeptide | 23 | |

Furthermore, Env polypeptides are not limited to a polypeptide having one of the exact sequences described herein. Indeed, the HIV genome is in a state of constant flux and contains several variable domains which exhibit relatively high degrees of variability between isolates. It is readily apparent that the terms encompass Env (e.g., gp160, gp140, and gp120) polypeptides from any of the identified HIV isolates, as well as newly identified isolates, and subtypes of these isolates. Descriptions of structural features are given herein with reference to SF162. One of ordinary skill in the art in view of the teachings of the present disclosure and the art can determine corresponding regions in other HIV variants (e.g., isolates $HIV_{IIIb}$, $HIV_{SF2}$, $HIV\text{-}1_{SF162}$, $HIV\text{-}1_{SF170}$, $HIV_{LAV}$, $HIV_{LAI}$, $HIV_{MN}$, $HIV\text{-}1_{CM235}$, $HIV\text{-}1_{US4}$, other HIV-1 strains from diverse subtypes (e.g., subtypes, A through G, and O), HIV-2 strains and diverse subtypes (e.g., $HIV\text{-}2_{UC1}$ and $HIV\text{-}2_{UC2}$), and simian immunodeficiency virus (SIV). (See, e.g., Virology, 3rd Edition (W. K. Joklik ed. 1988); Fundamental Virology, 2nd Edition (B. N. Fields and D. M. Knipe, eds. 1991); Virology, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify P-sheet regions). The actual amino acid sequences of the Env polypeptides can be based on any HIV variant.

Additionally, the term Env polypeptide (e.g., gp160, gp140, and gp120) encompasses proteins which include additional modifications to the native sequence, such as additional internal deletions, additions and substitutions. These modifications may be deliberate, as through site-directed mutagenesis, or may be accidental, such as through naturally occurring mutational events. However, the modifications must be such that immunological activity (i.e., the ability to elicit an antibody response to the Env polypeptides found in HIV) is not lost.

Examples of modifications and mutations to Env polypeptides include deletions or replacements of all or a part of the bridging sheet portion and, optionally, the variable regions V1 and V2. Generally, modified Env polypeptides have enough of the bridging sheet removed to expose the CD4 binding site, but leave enough of the structure to allow correct folding (e.g., correct geometry). Thus, modifications to the β-20 and β-21 regions (between about amino acid residues 420 and 435 relative to HXB-2) are preferred. Additionally, modifications to the β-2 and β-3 regions (between about amino acid residues 119 (Cys) and 201 (Ile)) and modifications (e.g., deletions) to the V1 and V2 loop regions may also be made. Other exemplary mutations can abrogate the cleavage site in Env to prevent enzymatic cleavage of oligomeric gp140 into gp120 monomers. (See, e.g., Earl et al. (1990) PNAS USA 87:648-652; Earl et al. (1991) J. Virol. 65:31-41). In yet other embodiments, N-glycosylation sites may be removed. Additional modifications and mutations to Env polypeptides may be found in WO00/39303, WO00/39302, WO00/39304, and WO02/04493. Additional examples of Env polypeptides may be found in U.S. Pat. No. 5,792,459 (for a description of $HIV_{SF2}$ Env polypeptides).

An immunogenic Env polypeptide is a molecule that includes at least one epitope such that the molecule is capable of either eliciting an immunological reaction in an individual to which the protein is administered or, in the diagnostic context, is capable of reacting with antibodies directed against the HIV in question.

Additional HIV Polypeptides

Wild-type HIV coding sequences for additional HIV polypeptides (e.g., Gag, Pol, tat, rev, nef, vpr, vpu, vif, etc.) can be selected from any known HIV isolate. The wild-type coding region may be modified in any way including one or more of the ways discussed below. As discussed above, different mutations may be introduced into the coding sequences of different genes.

The HIV genome and various polypeptide-encoding regions are shown in Table 2. The nucleotide positions are given relative to 8—5_TV1_C.ZA (an HIV Type C isolate). However, it will be readily apparent to one of ordinary skill in the art in view of the teachings of the present disclosure how to determine corresponding regions in other HIV strains or variants (e.g., isolates $HIV_{IIIb}$, $HIV_{SF2}$, $HIV\text{-}1_{SF162}$, $HIV\text{-}1_{SF170}$, $HIV_{LAV}$, $HIV_{LAI}$, $HIV_{MN}$, $HIV\text{-}1_{CM235}$, $HIV\text{-}1_{US4}$) other HIV-1 strains from diverse subtypes (e.g., subtypes, A through G, and O), HIV-2 strains and diverse subtypes (e.g., HIV-2UC1 and HIV-2UC2), and simian immunodeficiency virus (SIV). (See, e.g., Virology, 3rd Edition (W. K. Joklik ed. 1988); Fundamental Virology, 2nd Edition (B. N. Fields and D. M. Knipe, eds. 1991); Virology, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify the various regions).

TABLE 2

Regions of the HIV Genome relative to 8_5_TV1_C.ZA

| Region | Position in nucleotide sequence |
|---|---|
| 5'LTR | 1-636 |
| U3 | 1-457 |
| R | 458-553 |
| U5 | 554-636 |
| NFkB II | 340-348 |
| NFkB I | 354-362 |
| Sp1 III | 379-388 |
| Sp1 II | 390-398 |
| Sp1 I | 400-410 |
| TATA Box | 429-433 |
| TAR | 474-499 |
| Poly A signal | 529-534 |
| PBS | 638-655 |
| p7 binding region, packaging signal | 685-791 |
| Gag: | 792-2285 |
| p17 | 792-1178 |
| p24 | 1179-1871 |
| Cyclophilin A bdg. | 1395-1505 |
| MHR | 1632-1694 |
| p2 | 1872-1907 |
| p7 | 1908-2072 |
| Frameshift slip | 2072-2078 |
| p1 | 2073-2120 |
| p6Gag | 2121-2285 |
| Zn-motif I | 1950-1991 |
| Zn-motif II | 2013-2054 |
| Pol: | 2072-5086 |
| p6Pol | 2072-2245 |
| Prot | 2246-2542 |
| p66RT | 2543-4210 |
| p15RNaseH | 3857-4210 |
| p31Int | 4211-5086 |
| Vif: | 5034-5612 |
| Hydrophilic region | 5292-5315 |
| Vpr: | 5552-5839 |
| Oligomerization | 5552-5677 |
| Amphipathic a-helix | 5597-5653 |
| Tat: | 5823-6038 and 8417-8509 |
| Tat-1 exon | 5823-6038 |
| Tat-2 exon | 8417-8509 |
| N-terminal domain | 5823-5885 |
| Trans-activation domain | 5886-5933 |
| Transduction domain | 5961-5993 |
| Rev: | 5962-6037 and 8416-8663 |
| Rev-1 exon | 5962-6037 |

TABLE 2-continued

Regions of the HIV Genome relative to 8_5_TV1_C.ZA

| Region | Position in nucleotide sequence |
|---|---|
| Rev-2 exon | 8416-8663 |
| High-affinity bdg. site | 8439-8486 |
| Leu-rich effector domain | 8562-8588 |
| Vpu: | 6060-6326 |
| Transmembrane domain | 6060-6161 |
| Cytoplasmic domain | 6162-6326 |
| Env (gp160): | 6244-8853 |
| Signal peptide | 6244-6324 |
| gp120 | 6325-7794 |
| V1 | 6628-6729 |
| V2 | 6727-6852 |
| V3 | 7150-7254 |
| V4 | 7411-7506 |
| V5 | 7663-7674 |
| C1 | 6325-6627 |
| C2 | 6853-7149 |
| C3 | 7255-7410 |
| C4 | 7507-7662 |
| C5 | 7675-7794 |
| CD4 binding | 7540-7566 |
| gp41 | 7795-8853 |
| Fusion peptide | 7789-7842 |
| Oligomerization domain | 7924-7959 |
| N-terminal heptad repeat | 7921-8028 |
| C-terminal heptad repeat | 8173-8280 |
| Immunodominant region | 8023-8076 |
| Nef: | 8855-9478 |
| Myristoylation | 8858-8875 |
| SH3 binding | 9062-9091 |
| Polypurine tract | 9128-9154 |
| SH3 binding | 9296-9307 |

Gag Polypeptides

The additional HIV polypeptides may include Gag polypeptides. The full length Gag-polymerase sequence may be included in the Gag polypeptide in order to increase the number of epitopes. Because such full length polypeptides include the potentially deleterious functional enzymes reverse transcriptase (RT) and integrase (INT) (in addition to the structural proteins and protease), it is important to inactivate RT and INT functions. Several in-frame deletions in the RT and INT reading frame can be made to achieve catalytic nonfunctional enzymes with respect to their RT and INT activity. (See, e.g., Jay. A. Levy (Editor) (1995) The Retroviridae, Plenum Press, New York. ISBN 0-306-45033×. Pages 215-20; Grimison, B. and Laurence, J. (1995), Journal Of Acquired Immune Deficiency Syndromes and Human Retrovirology 9(1):58-68; Wakefield, J. K., et al., (1992) Journal Of Virology 66(11):6806-6812; Esnouf, R., et al., (1995) Nature Structural Biology 2(4):303-308; Maignan, S., et al., (1998) Journal Of Molecular Biology 282(2):359-368; Katz, R. A. and Skalka, A. M. (1994) Annual Review Of Biochemistry 73 (1994); Jacobo-Molina, A., et al., (1993) Proceedings Of the National Academy Of Sciences Of the United States Of America 90(13):6320-6324; Hickman, A. B., et al., (1994) Journal Of Biological Chemistry 269(46): 29279-29287; Goldgur, Y., et al., (1998) Proceedings Of the National Academy Of Sciences Of the United States Of America 95(16):9150-9154; Goette, M., et al., (1998) Journal Of Biological Chemistry 273(17):10139-10146; Gorton, J. L., et al., (1998) Journal of Virology 72(6):5046-5055; Engelman, A., et al., (1997) Journal Of Virology 71(5):3507-3514; Dyda, F., et al., Science 266(5193): 1981-1986; Davies, J. F., et al., (1991) Science 252(5002):88-95; Bujacz, G., et al., (1996) Febs Letters 398(2-3):175-178; Beard, W. A., et al., (1996) Journal Of Biological Chemistry 271(21):12213-12220; Kohlstaedt, L. A., et al., (1992) Science 256(5065): 1783-1790; Krug, M. S. and Berger, S. L. (1991) Biochemistry 30(44):10614-10623; Mazumder, A., et al., (1996) Molecular Pharmacology 49(4):621-628; Palaniappan, C., et al., (1997) Journal Of Biological Chemistry 272(17):11157-11164; Rodgers, D. W., et al., (1995) Proceedings Of the National Academy Of Sciences Of the United States Of America 92(4):1222-1226; Sheng, N. and Dennis, D. (1993) Biochemistry 32(18):4938-4942; Spence, R. A., et al., (1995) Science 267(5200):988-993.}

Furthermore selected B- and/or T-cell epitopes can be added to the Gag-polymerase polypeptides within the deletions of the RT- and INT-coding sequence to replace and augment any epitopes deleted by the functional modifications of RT and INT. Alternately, selected B- and T-cell epitopes (including CTL epitopes) from RT and INT can be included in other additional HIV polypeptides. (For descriptions of known HIV B- and T-cell epitopes see, HIV Molecular Immunology Database CTL Search Interface; Los Alamos Sequence Compendia, 1987-1997; Internet address hiv-web.lanl.gov under the directory immunology/index.html).

Representative mutations to the protease include attenuation of protease activity (Thr26Ser) and inactivation of the protease (Asp25Ala) (e.g., Konvalinka et al., 1995, J Virol 69:7180-86). Representative mutations to the reverse transcriptase include deletion of the catalytic center (e.g., Biochemistry, 1995, 34, 5351, Patel et al.), and deletion of the primer grip region (e.g., J Biol Chem, 272, 17, 11157, Palaniappan, et al., 1997). Representative mutations to the integrase include mutation of the HHCC domain (Cys40Ala), inactivation of the catalytic center (Asp64Ala, Asp1 16Ala, Glu 152Ala) (e.g., Wiskerchen et al., 1995, J Virol, 69:376), and inactivation of the minimal DNA binding domain (MDBD) (deletion of Trp235) (e.g., Ishikawa et al., 1999, J Virol, 73: 4475).

Pol Polypeptides

The additional HIV polypeptides may include Pol polypeptides. Pol polypeptides include, but are not limited to, the protein-encoding regions comprising polymerase, protease, reverse transcriptase and/or integrase-containing sequences (Wan et al. (1996) Biochem. J. 316:569-573; Kohl et al. (1988) PNAS USA 85:4686-4690; Krausslich et al. (1988) J. Virol. 62:4393-4397; Coffin, "Retroviridae and their Replication" in Virology, pp 1437-1500 (Raven, N.Y., 1990); Patel et al. (1995) Biochemistry 34:5351-5363). Thus, the Pol polypeptides herein include one or more of these regions and one or more changes to the resulting amino acid sequences.

In certain embodiments, the catalytic center and/or primer grip region of RT are modified as described above. The catalytic center and primer grip regions of RT are described, for example, in Patel et al. (1995) Biochem. 34:5351 and Palaniappan et al. (1997) J. Biol. Chem. 272(17): 11157. For example, wild type sequence encoding the amino acids YMDD at positions 183-185 of p66 RT, numbered relative to AF110975, may be replaced with sequence encoding the amino acids "AP". Further, the primer grip region (amino acids WMGY, residues 229-232 of p66RT, numbered relative to AF110975) may be replaced with sequence encoding the amino acids "PI."

Vif, Vpr, and Vpu Polypeptides

The additional HIV polypeptides may include Vif, Vpr and Vpu polypeptides. Reducing or eliminating the function of the associated gene products can be accomplished employing routine methods available in the art. By way of example, Simon et al. (J. Virol 73:2675-81, 1999) teach mutations of Vif. Simon et al. (J. Virol. 74:10650-57, 2000) teach mutations of Vpr. Tiganos et al. (Virology 251:96-107, 1998) teach mutation of Vpu.

Tat Polypeptides

The additional HIV polypeptides may include Tat polypeptides. Tat polypeptides may be modified using routine methods taught in the art (e.g., replacing a cysteine residue at position 22 with a glycine or a cysteine at position 37 with a serine, Caputo et al. Gene Therapy 3:235, 1996).

Rev Polypeptides

The additional HIV polypeptides may include Rev polypeptides. Rev polypeptides may be modified using routine methods taught in the art (e.g., mutations in the Rev domains (e.g., Thomas et al., 1998, J Virol. 72: 2935-44), mutation in RNA binding-nuclear localization (ArgArg38, 39AspLeu=M5), and mutation in the activation domain (LeuGlu78,79AspLeu=M10)).

Nef Polypeptides

The additional HIV polypeptides may include Nef polypeptides. Nef polypeptides may be modified using routine methods taught in the art (e.g., mutations of the myristoylation signal and in the oligomerization domain: point mutations to the myristoylation signal (Gly-to-Ala=−Myr), deletion of N-terminal first 18 (sub-type B, e.g., SF162) or 19 (sub-type C, e.g., South Africa clones) amino acids: −Myr18 or −Myr19 (respectively) (e.g., Peng and Robert-Guroff, 2001, Immunol Letters 78: 195-200), single point mutation to the oligomerization domain (Asp125Gly (sub B SF162) or Asp 124Gly (sub C South Africa clones)) (e.g., Liu et al., 2000, J Virol 74: 5310-19), and mutations affecting (1) infectivity (replication) of HIV-virions and/or (2) CD4 down regulation. (e.g., Lundquist et al. (2002) J Virol. 76(9): 4625-33)).

Methods of Producing Env Polypeptides and Additional HIV Polypeptides

The polypeptides disclosed herein can be produced in any number of ways which are well known in the art.

In one embodiment, the polypeptides are generated using recombinant techniques, well known in the art. In this regard, oligonucleotide probes can be devised based on the known sequences of Env and other HIV polypeptides and used to probe genomic or cDNA libraries for Env and other HIV genes. The gene can then be further isolated using standard techniques, e.g., restriction enzymes employed to truncate the gene at desired portions of the full-length sequence. Similarly, Env and other HIV genes can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The genes encoding the modified (e.g., truncated and/or substituted) polypeptides can be produced synthetically, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311; Stemmer et al. (1995) Gene 164:49-53.

Recombinant techniques are readily used to clone a gene encoding Env and other HIV polypeptide genes which can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer which hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al., (1990) PCR Applications: Protocols for Functional Genomics; Zoller and Smith, Methods Enzymol. (1983) 100:468. Primer extension is effected using DNA polymerase; the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. Proc. Natl. Acad. Sci. USA (1982) 79:6409.

Once coding sequences for the desired proteins have been isolated or synthesized, they can be cloned into any suitable vector or replicon for expression. As will be apparent from the teachings herein, a wide variety of vectors encoding modified polypeptides can be generated by creating expression constructs which operably link, in various combinations, polynucleotides encoding Env and other HIV polypeptides having deletions or mutation therein. Thus, for example, polynucleotides encoding a particular portion with the deleted V1/V2 region for an Env polypeptide can be operably linked with polynucleotides encoding Env polypeptides having deletions or replacements in the small loop region and the construct introduced into a host cell for expression of the Env polypeptide.

Numerous cloning vectors are known to those of skill in the art, and the selection of an appropriate cloning vector is a matter of choice. Examples of recombinant DNA vectors for cloning and host cells which they can transform include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

Insect cell expression systems, such as baculovirus systems, can also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit).

Plant expression systems can also be used to produce Env and other HIV polypeptides. Generally, such systems use virus-based vectors to transfect plant cells with heterologous genes. For a description of such systems see, e.g., Porta et al., Mol. Biotech. (1996) 5:209-221; and Hackland et al., Arch. Virol. (1994) 139:1-22.

Viral systems, such as a vaccinia based infection/transfection system, as described in Tomei et al., J. Virol. (1993) 67:4017-4026 and Selby et al., J. Gen. Virol. (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired Env or other HIV polypeptide is transcribed into RNA in the host cell transformed by a vector containing this expression construction. The coding sequence may or may not contain a signal peptide or leader sequence. Both the naturally occurring signal peptides and heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. For the Env polypeptides, expression in mammalian cells is preferred to ensure proper glycosylation. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Bombyx mori, Drosophila melanogaster, Spodoptera frugiperda*, and *Trichoplusia ni.*

Depending on the expression system and host selected, the proteins of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, a γ-interferon signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the Env or other HIV polypeptides substantially intact. Intracellular proteins can also be obtained by removing components from the cell wall or membrane, e.g., by the use of detergents or organic solvents, such that leakage of Env or other HIV polypeptides occurs. Such methods are known to those of skill in the art and are described in, e.g., Protein Purification Applications: A Practical Approach, (E. L. V. Harris and S. Angal, Eds., 1990)

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pretreatment used.

Following disruption of the cells, cellular debris is removed, generally by centrifugation, and the intracellularly produced Env and other HIV polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining intracellular Env polypeptides of the present invention involves affinity purification, such as by immunoaffinity chromatography using anti-Env specific antibodies, or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the Env and other HIV polypeptides can be further purified using conventional techniques well known in the art, such as by any of the techniques described above.

Relatively small polypeptides, i.e., up to about 50 amino acids in length, can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis, Synthesis, Biology, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptide analogs of the present invention can also be chemically prepared by other methods such as by the method of simultaneous multiple peptide synthesis. See, e.g., Houghten Proc. Natl. Acad. Sci. USA (1985) 82:5131-5135; U.S. Pat. No. 4,631,211.

Vaccines

The Env polypeptides complexed to polyanionic carbomers and immunogenic compositions comprising such complexes ("Env polypeptide complexes") and the Env polypeptides with low viscosity, polyanionic polymers (Env polypeptide complexes and low viscosity, polyanionic carbomer-Env polypeptide compositions collectively are "Env compositions") can be used in various vaccine compositions, individually or in combination, in e.g., prophylactic (i.e., to prevent infection) or therapeutic (to treat HIV following infection) vaccines. The vaccines can comprise mixtures of one or more Env polypeptides, such as Env polypeptides derived from more than one viral isolate. The vaccine may also be administered in conjunction with other antigens and immunoregulatory agents, for example, immunoglobulins, cytokines, lymphokines, and chemokines, including but not limited to IL-2, modified IL-2 (cys125→ser125), GM-CSF, IL-12, γ-interferon, IP-10, MIP1β and RANTES. The vaccines may also comprise a mixture of protein and nucleic acid, which in turn may be delivered using the same or different vehicles. The Env composition vaccines may be given more than once (e.g., a "prime" administration followed by one or more "boosts") to achieve the desired effects. The same composition can be administered as the prime and as the one or more boosts. Alternatively, different compositions can be used for priming and boosting.

By way of example, any of the Env composition vaccines can be used in combination with other DNA delivery systems and/or protein delivery systems with HIV antigens. Non-limiting examples include co-administration of these molecules, for example, in prime-boost methods where one or more molecules are delivered in a "priming" step and, subsequently, one or more molecules are delivered in a "boosting" step. In certain embodiments, the delivery of one or more nucleic acid-containing compositions and is followed by delivery of the Env composition vaccines. In other embodiments, multiple nucleic acid "primes" (of the same or different nucleic acid molecules) can be followed by multiple Env composition "boosts" (of the same or different Env polypeptides and additional HIV polypeptides).

The vaccines will generally include one or more pharmaceutically acceptable excipients or vehicles such as water, saline, glycerol, ethanol, etc. Additionally, auxiliary substances, such as wetting or emulsifying agents, pH buffering substances, and the like, may be present in such vehicles.

A carrier is optionally present. Carriers are molecules that do not alone induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the Env polypeptide in the Env compositions may be conjugated to a bacterial toxoid, such as toxoid from diphtheria, tetanus, cholera, etc.

Adjuvants may also be used to enhance the effectiveness of the vaccines. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59™ (International Publication No. WO 90/14837), containing 5% Squalene, 0.5% TWEEN 80™, and 0.5% SPAN 85™ (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% TWEEN 80™, 5% pluronic-blocked polymer L121, and thr-MDP (see below) either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN 80™, and one or more bacterial cell wall components from the group consisting of monophosphorylipid A (MPL), trehalose dimycolate (TDM), and cell wall skeleton (CWS), preferably MPL+CWS (DETOX™); (3) saponin adjuvants, such as STIMULON™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

The vaccines will comprise a therapeutically effective amount of the Env compositions and any other of the above-mentioned components, as needed. A therapeutically effective amount will be an amount of the Env composition that will induce a protective immunological response in the uninfected, infected or unexposed individual to which it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell.

Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular Env polypeptide selected and its mode of administration, among other factors. An appropriate effective amount can be readily determined by one of skill in the art. A therapeutically effective amount will fall in a relatively broad range that can be determined through routine trials.

The Env composition vaccines can be injected either subcutaneously, epidermally, intradermally, intramucosally such as nasally, rectally and vaginally, intraperitoneally, intravenously, orally or intramuscularly. Other modes of administration include oral and pulmonary administration, suppositories, needle-less injection, transcutaneous and transdermal applications. Dosage treatment may be a single dose schedule or a multiple dose schedule.

General

The term "comprising" encompasses "including" as well as "consisting", e.g., a composition "comprising" X may consist exclusively of X or may include something additional, e.g., X+Y.

The word "substantially" does not exclude "completely", e.g., a composition which is "substantially free" from Y may be completely free from Y. Where necessary, the word "substantially" may be omitted from the definition of the invention. The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a cell substrate is used for reassortment or reverse genetics procedures, it is preferably one that has been approved for use in human vaccine production, e.g., as in Ph Eur general chapter 5.2.3.

Identity between polypeptide sequences is preferably determined by the Smith-Waterman homology search algorithm as implemented in the MPSRCH program (Oxford Molecular), using an affine gap search with parameters gap open penalty=12 and gap extension penalty=1.

As used in this specification, the singular forms "a," "an" and "the" include plural references unless the content clearly dictates otherwise. Thus, for example, reference to "an antigen" includes a mixture of two or more such agents.

EXAMPLES

Example 1

Generation of Polyanionic Carbomer+Env Complexes

CARBOPOL 971P NF™ was weighed under sterile condition. Half the final volume of 0.2μ filtered, distilled $H_2O$ was added to the CARBOPOL™ powder and left in a rotator for end-over-end mixing for 5-10 minutes. The remaining volume of water was then added and left in rotator for end-over-end mixing for 16-18 hours to allow a uniform suspension to form. Using these methods, homogeneous suspensions of 1-2% CARBOPOL™ can be readily made. Longer periods of continuous mixing were required for higher concentrations of CARBOPOL™ to ensure a homogenous suspension. Suspensions above 4% took longer to form and were too viscous to handle for analytical or gel analysis purposes after formation of the Env complexes. The pH of the final solution was measured and typically found in the range of pH 3.0-4.0. Due to high viscosity, suspensions of greater than 2% Carbopol were not tested in any in vitro or in vivo applications.

The pH was important for the formation of the complexes. When the pH was adjusted to 7.0 by addition of 3M NaOH/1M KOH before addition of the Env polypeptide, Dynamic Light Scattering (DLS) analysis showed no interaction between the Env polypeptide and the CARBOPOL™. By contrast, when the Env polypeptide was added to the low pH (3.0-4.0) acidic CARBOPOL™, the Env polypeptides and the CARBOPOL™ formed a complex, predominantly mediated by electrostatic interactions. At pH 3.0-4.0, Env polypeptide is positively charged while polyanionic carbomers such as CARBOPOL™ are negatively charged—this allows charged-charged interaction between Env polypeptide and polyanionic molecules or polymers, facilitating the formation of complex. If CARBOPOL™ or similar polyanionic carbomers are first adjusted to pH ~7, then direct interaction with Env polypeptide (or with other positively charged proteins) will not occur and hence no complexation. With the correct pH, the complexes form relatively quickly, requiring only incubation for ≤1 hour. The complexes form readily, possibly much sooner than 1 hr since charge-charge interactions are instantaneous and rapid.

Example 2

Stability of the Env Polypeptide Complexed with Anionic Carbomers

In attempting to stabilize soluble, recombinant Env polypeptides for vaccination and to increase the adjuvantation provided by adjuvants such as MF59™, a polyanionic carbomer, CARBOPOL 971P NF™, was tested. To assess the stability of Env polypeptides complexed with polyanionic carbomers, purified oligomer SF162 gp140ΔV2 Env polypeptide produced from CHO cells complexed with 0.5% CARBOPOL 971P NF™ was incubated for varying time-periods at 4° C. and analyzed by SDS-PAGE and immunoblotting, using anti-gp120 rabbit polyclonal sera. As shown in FIG. 1(A), the CARBOPOL 971P NF™ had no detrimental effect on Env. The Env polypeptide was stable in CARBOPOL 971P NF™-Env polypeptide complex at the longest time tested (4 hrs).

The stability of the Env polypeptide complexes was also tested at varying temperatures: 1 hour at each of 4° C., room temperature (RT, 20° C.), 30° C. and 37° C. As a control, the Env polypeptide in PBS was also incubated at RT and 37° C. As shown in FIG. 1(B), the Env polypeptide complexes were stable for 1 hour at all temperatures (4° C., room temperature, 30° C. and 37° C.) tested. A faint band can be seen in lane 4 of FIG. 1(B) at ~70 kDa. This band corresponds to a known cleavage product of gp140, generated by enzymatic cleavage of V3-loop; this fragment has nothing to do with CARBOMER 971P NF™. We observed this at higher temperature, and not at lower temperature. This was expected because the endoproteases that causes cleavage are active at these temperatures (room temperature to 37° C.). The Env polypeptide alone, therefore, was already showing some degree of degradation at one of the two temperatures tested—this again confirms that the enzymatic cleavage observed here was due to enzymatic activity as favorable temperatures (RT-37° C.), and not specific to presence of CARBOMER 971P NF™. In contrast, the Env polypeptide in complex with a polyanionic carbomer (CARBOMER 971P NF™) showed no degradation at any temperature tested, possibly also indicating that the protein can be partly protected from enzymatic cleavage in this complex; the protection could be due to the low pH (unfavorable for activity), steric hindrance caused by the polyanionic carbomer interfering with the enzyme, or both. Thus, forming a complex stabilizes the Env polypeptide.

Example 3

Interaction of Env Polypeptide and Polyanionic Carbomers Using Dynamic Light Scattering (DLS)

Figure 2:
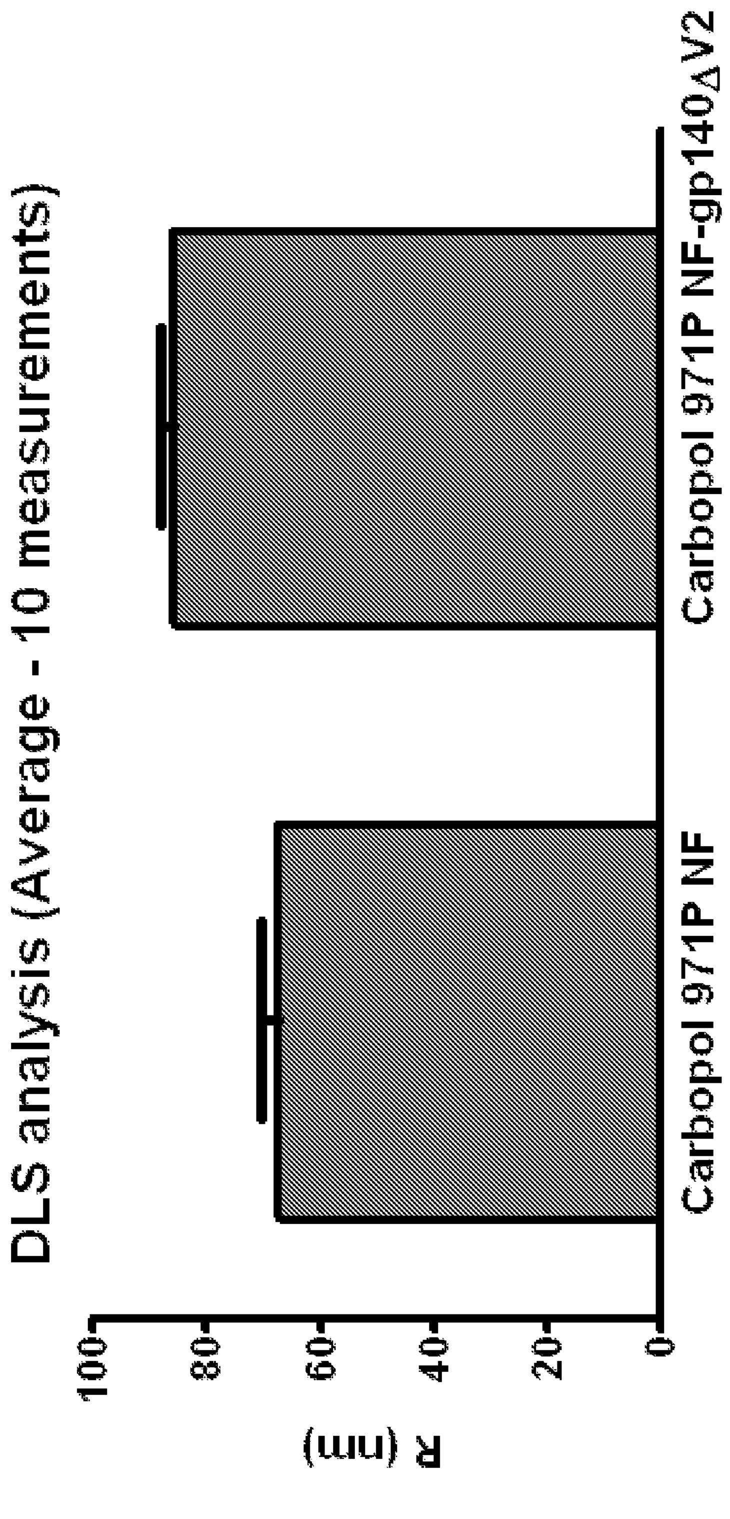
FIG. 2 shows the dynamic light scattering analysis (averaging ten measurements) for the CARBOPOL™ alone (left) or CARBOPOL™ in complex with the Env (gp140) polypeptide. The CARBOPOL™ alone displayed a hydrodynamic radius of ~68 nm. The CARBOPOL™+gp140 showed a radius of ~86 nm, indicating that the CARBOPOL™ and the gp140 were interacting in a higher order complex. The final concentration of CARBOPOL™ in the gels was ~0.1%.

To demonstrate that the Env polypeptide was forming a complex with the polyanionic carbomer via direct interaction and thereby stabilizing the Env polypeptide and/or aiding in the controlled release or presentation of the antigen, the complexes were analyzed by Dynamic Light Scattering (DLS) which measures the hydrodynamic radius of particles in solution. As shown in FIG. 2, the hydrodynamic radius of 0.5% CARBOPOL 971P NF™ alone was ~68 nm. By contrast, the hydrodynamic radius of CARBOPOL 971P NF™+Env polypeptide complex was ~86 nm. This increased size of the complex indicated that the Env polypeptide was directly adsorbed on the carbomer surface via charge-charge interaction. The Env polypeptide by itself has a hydrodynamic radius of >10 nm, so the CARBOPOL 971P NF™ was clearly forming a complex with the Env polypeptide.

Example 4

Antigenic Integrity of Env Polypeptide Complexed with Polyanionic Carbomers

Figure 4:
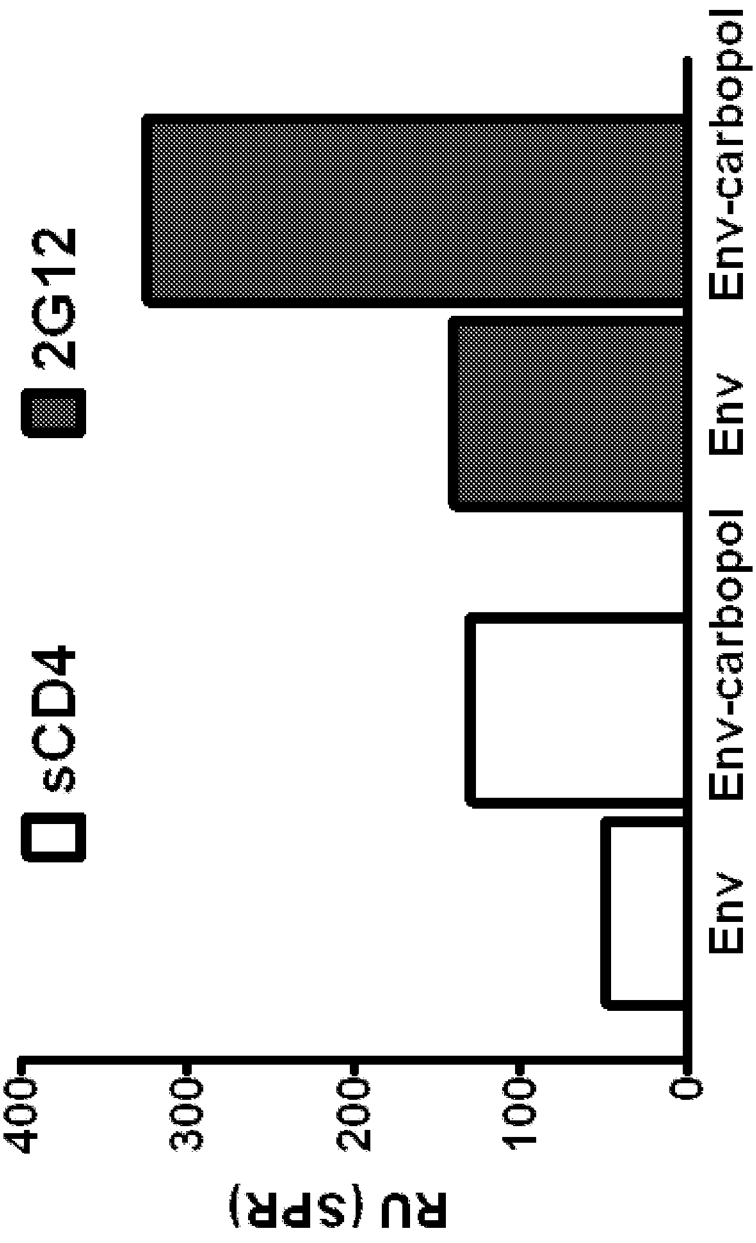
FIG. 4 shows a chart of the response units (RU—y-axis) measured via surface plasmon resonance for the Env polypeptide alone or in complex with polyanionic carbomers (CARBOPOL™). Binding to soluble CD4 (sCD4), bound to the sensor chip, is shown on the left with white bars. Binding to a glycan-dependent, monoclonal antibody (2G12), bound to the sensor chip, is shown on the right with shaded gray bars.

To verify that the polyanionic carbomers were not interfering with or disrupting important conformational or neutralizing epitopes in the Env polypeptide, the Env polypeptide-polyanionic carbomers (CARBOPOL 971P NF™) complexes were tested for their ability to bind receptor (CD4) and a monoclonal antibody (2G12, glycan-dependent). Soluble CD4 (sCD4) or mAb 2G12 were covalently immobilized on a CM5 sensor chip by amine coupling. For the complexes, the Env polypeptide protein and CARBOPOL 971P NF™ (final, 0.5%) were incubated at 4° C. for 1 hour. After incubation, 20-fold excess of HBS buffer was added and injected to analyze binding to the immobilized ligands. 100 nM of Env polypeptide (gp140ΔV2), either alone or in complex with polyanionic carbomers were injected at 10 μl/min. As shown in FIG. 4, the Env polypeptide alone bound to sCD4 with an average RU (response unit) of ~50. The Env polypeptide complexes bound to sCD4 with ~3-fold higher RU. Similarly, the Env polypeptide alone bound to mAb 2G12 with an RU of ~150, while the Env polypeptide complexes bound with ~3-fold higher RU. The Env polypeptide both alone and complexed to polyanionic carbomers bound to both ligands, indicating that the antigenic integrity of Env was unaffected by the complex. The consistent 3-fold difference between the RU of the Env polypeptide alone and in complex was most likely be due to size: the complex being larger in comparison to the Env polypeptide alone.

Figure 3A:
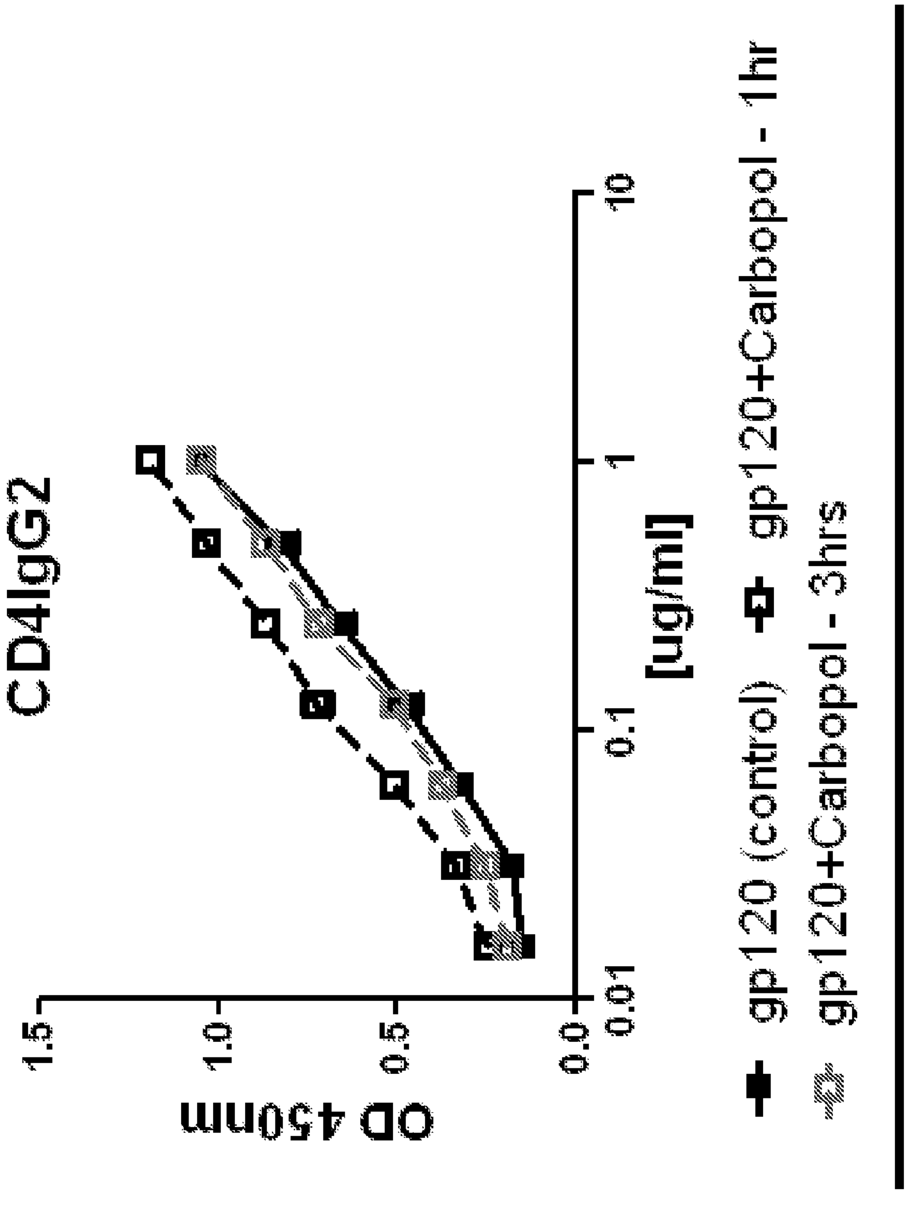
FIG. 3 shows ELISA assays testing binding of Env polypeptide incubated with 0.5% CARBOPOL™, 1:1 (v/v), (final conc. of CARBOPOL™ 0.25%) for one hour (dark grey open boxes) or three hours (light grey open boxes) at room temperature (25° C.). Env polypeptide without CARBOPOL™ (as control) was similarly incubated (closed boxes). The y-axis shows OD 450 nm and the x-axis shows concentration of gp120 (μg/ml). (A) shows the gp120 samples binding to CD4-IgG2 (surrogate for receptor CD4). (B) shows the gp120 samples binding to b12 (a CD4-binding site neutralizing monoclonal antibody, mAb). (C) shows binding to 17b mAb (a CD4-induced monoclonal antibody), in presence or absence of soluble CD4, sCD4. The CD4gG2 & b12 mAb binding shows that the conformational receptor binding site was antigenically intact, despite incubation with CARBOPOL™. The 17b mAb binding confirmed that the protein was able to undergo CD4-induced conformation change, a key aspect of functional Env polypeptide.
Figure 3B:
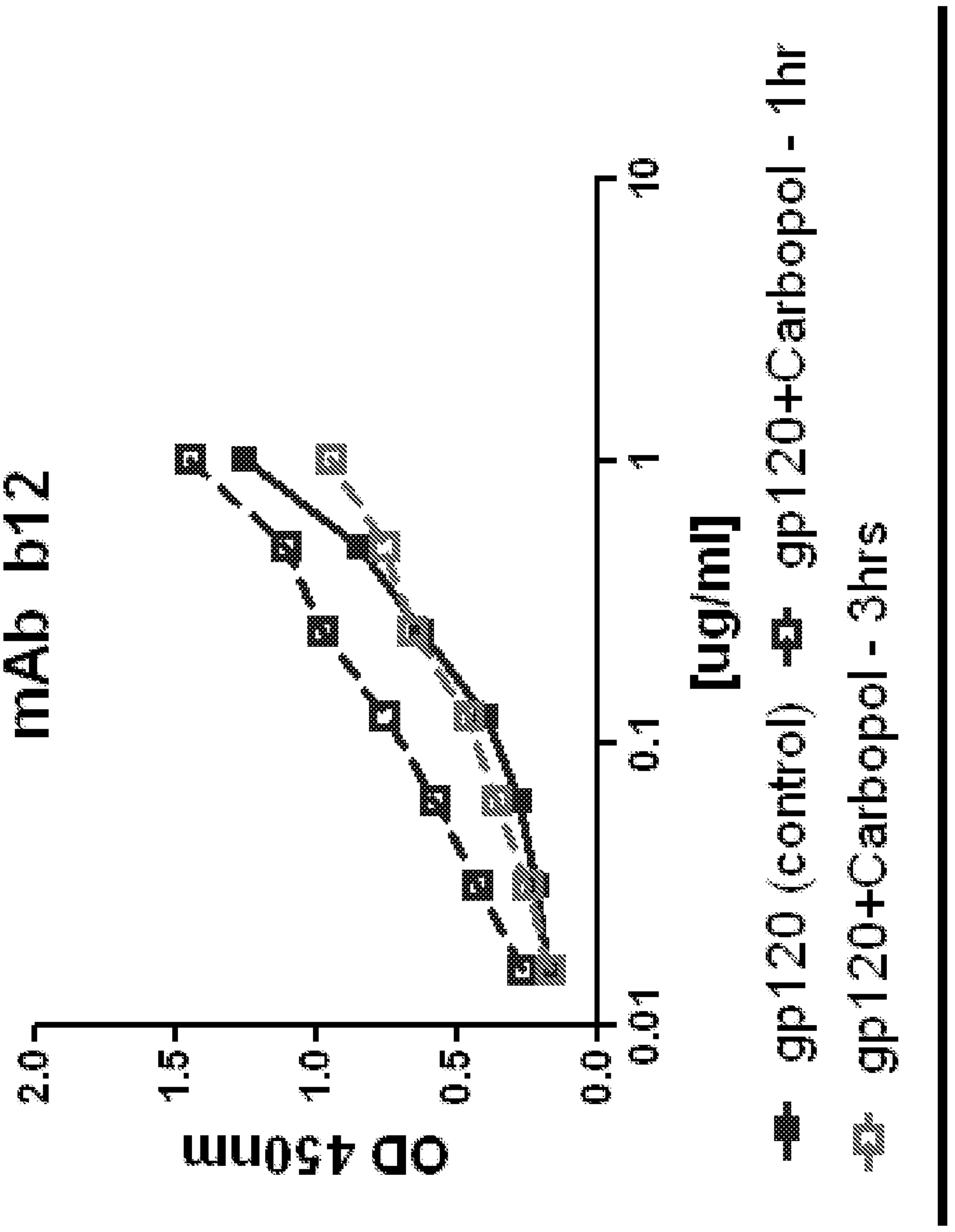
Figure 3C:
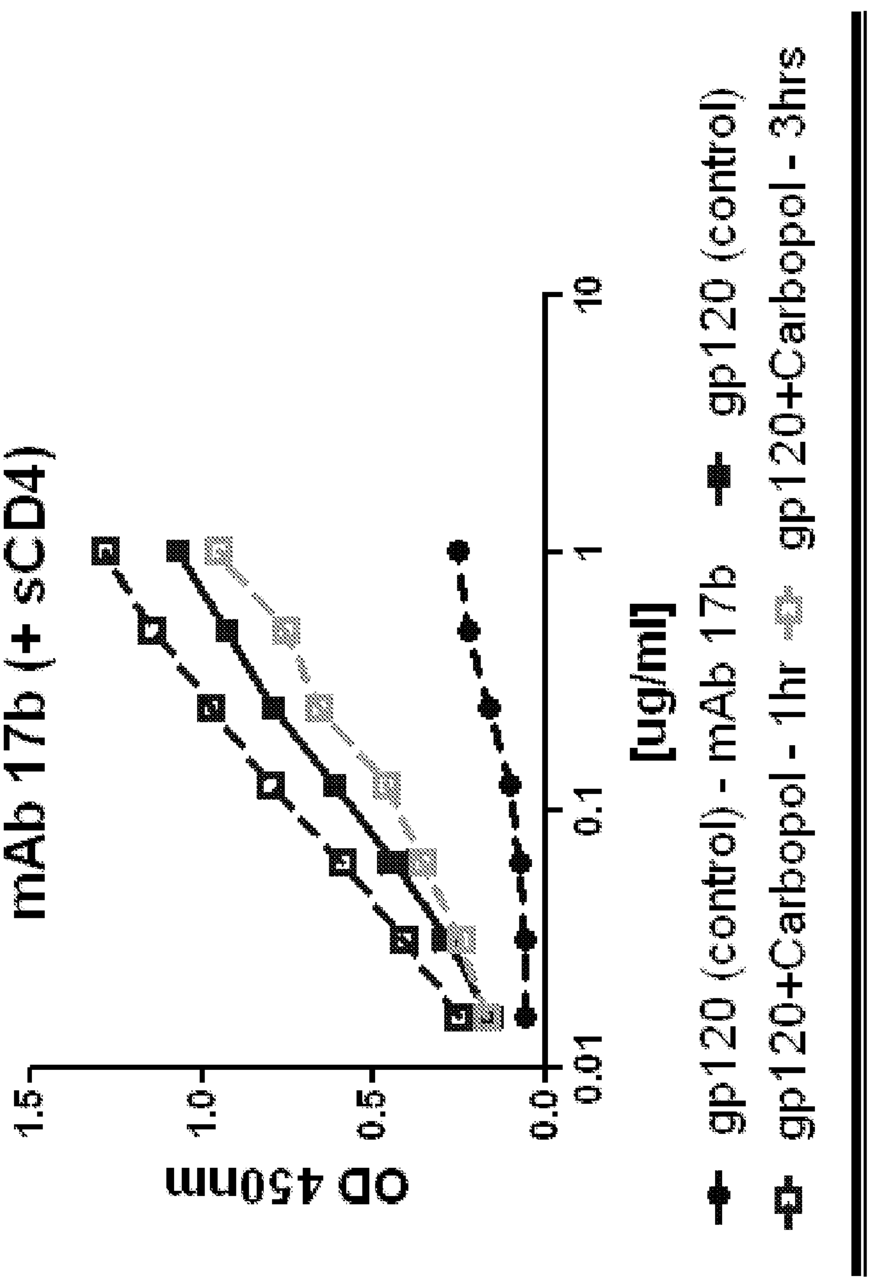

To further verify that the polyanionic carbomers were not interfering with or disrupting important conformational or neutralizing epitopes in the Env polypeptide, the Env polypeptide-polyanionic carbomers (CARBOPOL 971P NF™) complexes were tested for their ability to bind receptor (CD4, here CD4-IgG2 is used as surrogate) and a monoclonal antibody (2G12, glycan-dependent) using capture ELISA. The capture ELISA was performed by coating MAXISORB™ plates with 2 μg/ml of D3724 mAb (in PBS) (100 μl per well), overnight at 4° C. The following day, the surface was blocked with 1% BSA in PBS by incubating at 37° C. for one hour. The plates were then washed three times (PBS+0.01% TWEEN 20™) and 1 μg/ml gp120 either pre-incubated with or without CARBOPOL 971P NF™, in 0.1% BSA+0.01% TRITON X-100™ (dilution buffer) was added to the plates. The plates were incubated at room temperature (RT, 25° C.) for two hours. The plates were washed three times and anti-CD4 IgG2, b12 or 17b, was added in a serial dilution starting at 1 μg/ml and then 2-fold diluted (in dilution buffer) thereafter. In cases where CD4i-induction using 17b mAb was desired, equimolar amount of soluble CD4 (sCD4) was added to gp120. The plates were then incubated at RT for one hour and washed three times. Then anti-human HRP conjugated antibody was added to the reactions at 1:10,000 (in dilution buffer). Following one hour incubation at RT, the plates were washed three times and developed using KPL's TMB substrates. All samples were evaluated in triplicate. A surface containing capture antibody, but no gp120 (but primary antibody, secondary antibody and substrate added to it), was used as control for each specific ligand. The optical density (OD) was determined using a microplate reader (Molecular Devices) at 450 nm. The results are shown in FIGS. 3(A)-(C). The Env proteins with and without CARBOPOL 971P NF™ bound the respective ligands without any significant difference in binding affinity, indicating that the Env polypeptide do not denature or suffer antigenic alteration upon incubation in CARBOPOL 971P NF™ for up to 3 hours, which is sufficient time to form complex before administration for vaccine evaluations. Taken together, these data indicate that the gp140 Env polypeptide was stable in presence of CARBOPOL 971P NF™ preserving critical conserved epitopes involved in receptor and co-receptor binding.

Example 5

Immunogenicity of HIV-1 Subtype B Env Alone (Monovalent) Adjuvanted with CARBOPOL 971P NF™ (in Complex with the Env) or MF59™ or CARBOPOL 971P NF™ (in Complex with the Env)+MF59™ in a DNA Prime-Protein Boost (IM) Regimen This rabbit study is to compare CARBOPOL 971P NF™ (in complex) versus MF59™ versus CARBOPOL 971P NF™ (in complex)+MF59™ using a single (Subtype B SF162) gp140 Env polypeptide as immunogen. To confirm the immunogenicity, rabbits were immunized with the subtype B SF162 Env polypeptides in the complexes. New Zealand white rabbits, five per group, were immunized with 2 DNA primes (1 mg each immunization), followed by 25 μg of SF162 gp140ΔV2 (Env) protein boost with MF59™, CARBOPOL 971P NF™ or CARBOPOL 971P NF™+MF59™. This study was performed to compare the adjuvantation of CARBOPOL 971P NF™ versus MF59™ versus CARBOPOL 971P NF™+MF59™ using Subtype B SF162 gp140 Env polypeptide as (monovalent) immunogen. Four immunizations were administered intramuscularly, in the gluteus, at weeks 0, 4, 12, and 24. The total protein dosage at each immunization was 25 μg. Serum samples were collected prior to first immunization (pre-bleed) and at various time-points post each immunization (2wp2, 2wp3, 2wp4, 4wp4 and 15wp4 bleed-out) and analyzed for binding and neutralization.

Figure 5:
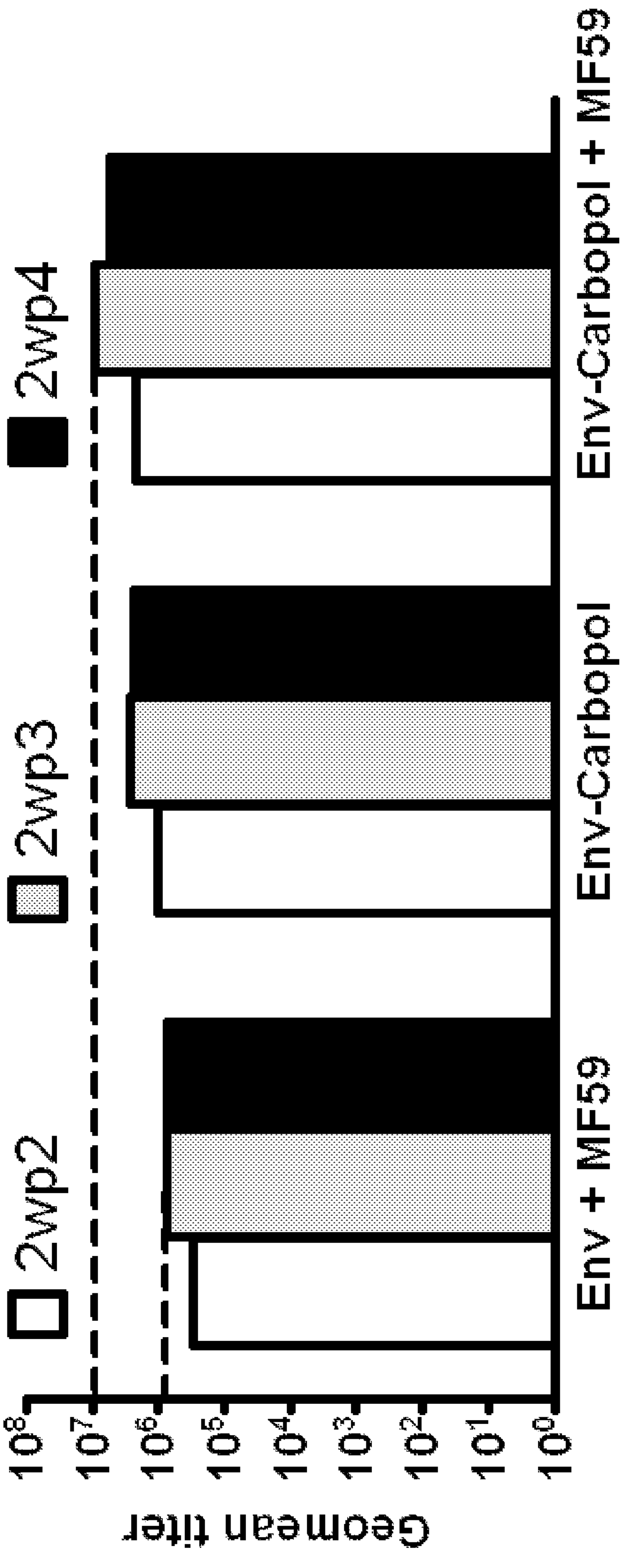
FIG. 5 shows a chart of the antibodies in sera as measured with gp120-binding ELISA (geometric mean titer—y axis) from a rabbit study comparing Env polypeptide (SF162 gp140) adjuvanted with CARBOPOL™ or MF59™ or CARBOPOL™+MF59™. The geometric mean titer at two-weeks post-second immunization (2wp2) is shown with white bars. The geometric mean titer at two-weeks post-third immunization (2wp3) is shown with light gray bars. The geometric mean titer at two-weeks post-fourth immunization (2wp4) is shown with black bars.

As measured using gp120-binding ELISA, Env polypeptide administered with MF59™ gave (geometric mean) titers of $>10^5$ at two-weeks post-second (2wp2) and gave the highest titers of $10^6$ at 2wp3. The response to the Env polypeptide administered with MF59™ did not improve post-fourth immunization. The Env polypeptide complexed to CARBOPOL 971P NF™ produced the highest titers of $>10^6$ at 2wp3. Most significantly, Env polypeptide complexed to CARBOPOL 971P NF™ and adjuvanted with MF59™ gave the highest titers of all (about $10^7$ at 2wp3—see FIG. 5).

Figure 6:
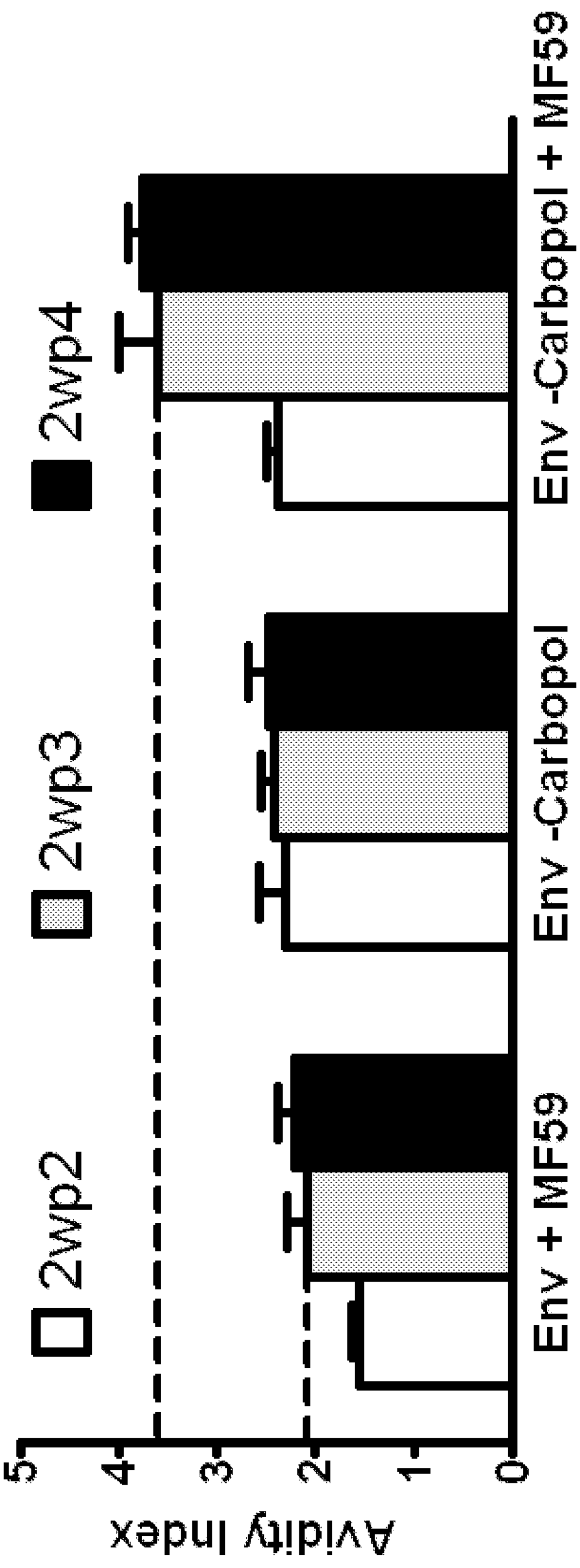
FIG. 6 shows a chart of the avidity of the gp120-specific serum antibodies assessed using ammonium thiocyanate ELISA (avidity index—y axis). The sera are from a rabbit study comparing Env polypeptide (SF162 gp140) adjuvanted with CARBOPOL™ or MF59™ or CARBOPOL™+MF59™. The avidity index at two-weeks post-second immunization (2wp2) is shown with white bars. The avidity index at two-weeks post-third immunization (2wp3) is shown with light gray bars. The avidity index at two-weeks post-fourth immunization (2wp4) is shown with black bars.

To further assess the immune response, the avidity of the gp140-specific serum antibodies produced by the vaccination protocol was assessed using ammonium thiocyanate ELISA (see FIG. 6). The avidity index provides an indication of the maturity of the antibodies produced.

The antibody avidity was similar following three or four immunizations of Env in MF59™ or complexed to CARBOPOL 971P NF™, when sera were evaluated 2-weeks post each immunization. In contrast, the antibody avidity doubled following administration of Env polypeptide complexed to CARBOPOL 971P NF™ and adjuvanted with MF59™ at 2wp3 and 2wp4, in comparison to the two other regimens. This significant difference in improving antibody avidity, including eliciting highly Env-specific binding antibodies, using Env polypeptide complexed to CARBOPOL 971P NF™ and adjuvanted with MF59™ is a noteworthy result and indicates that the CARBOPOL 971P NF™-Env polypeptide complexes and MF59™ work to further potentiate binding antibody response, as observed in this case. This could be due to synergistic effect where CARBOPOL™ works in delivery or controlled release of antigen and partial adjuvantation while MF59™ works towards more potent immune-potentiation.

Figure 7A:
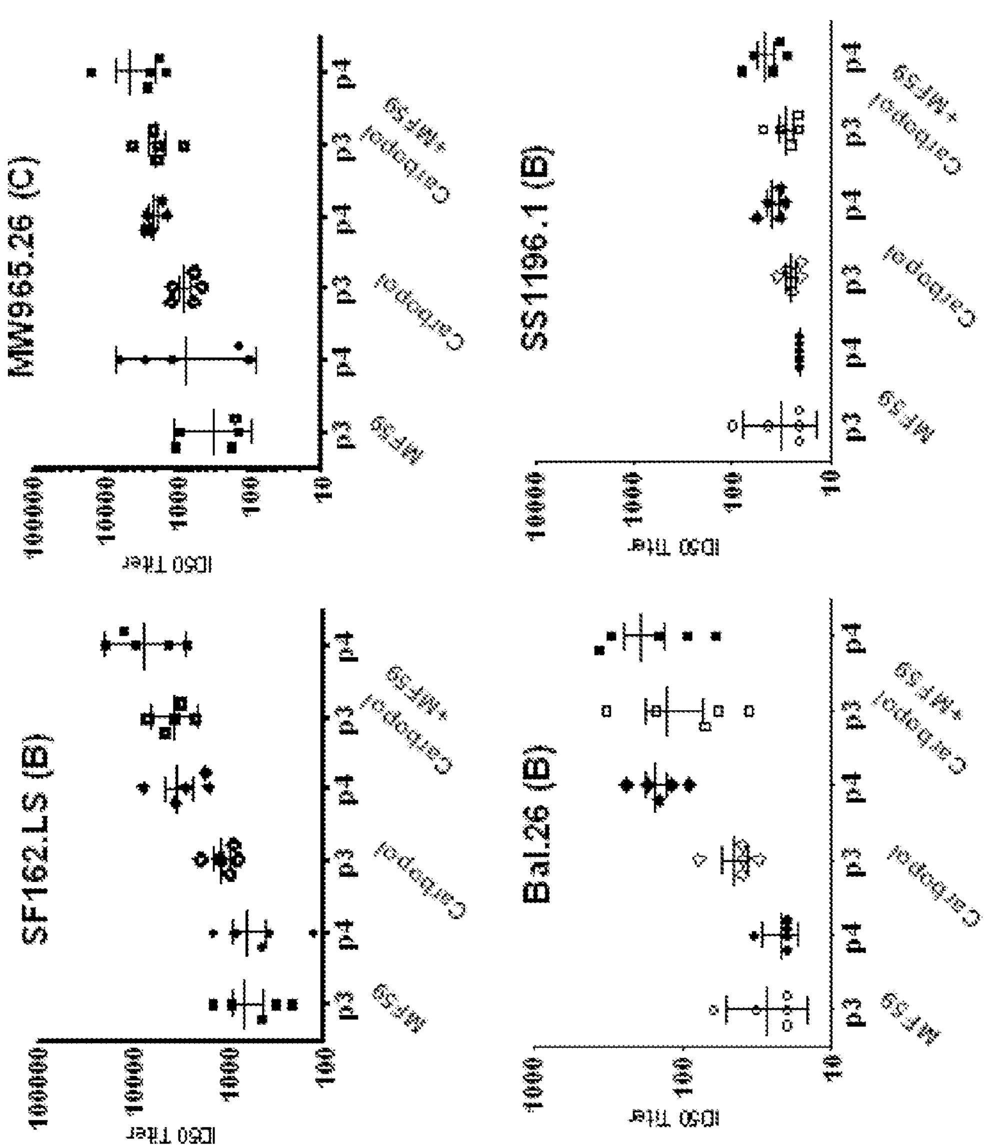
FIGS. 7A-B show results for the neutralization potential of Env-specific antibodies produced from the immunization regimens in a rabbit study comparing Env polypeptide (SF162 gp140) adjuvanted with CARBOPOL™ or MF59™ or CARBOPOL™+MF59™. Each graph shows ID50 titers of antibodies from post-third (p3) and post-fourth (p4) immunization for (a) immunization with Env polypeptides with MF59™, (b) immunization with Env polypeptides-polyanionic carbomer complexes, and (c) immunization with Env polypeptides-polyanionic carbomer complexes with MF59™.
Figure 7B:
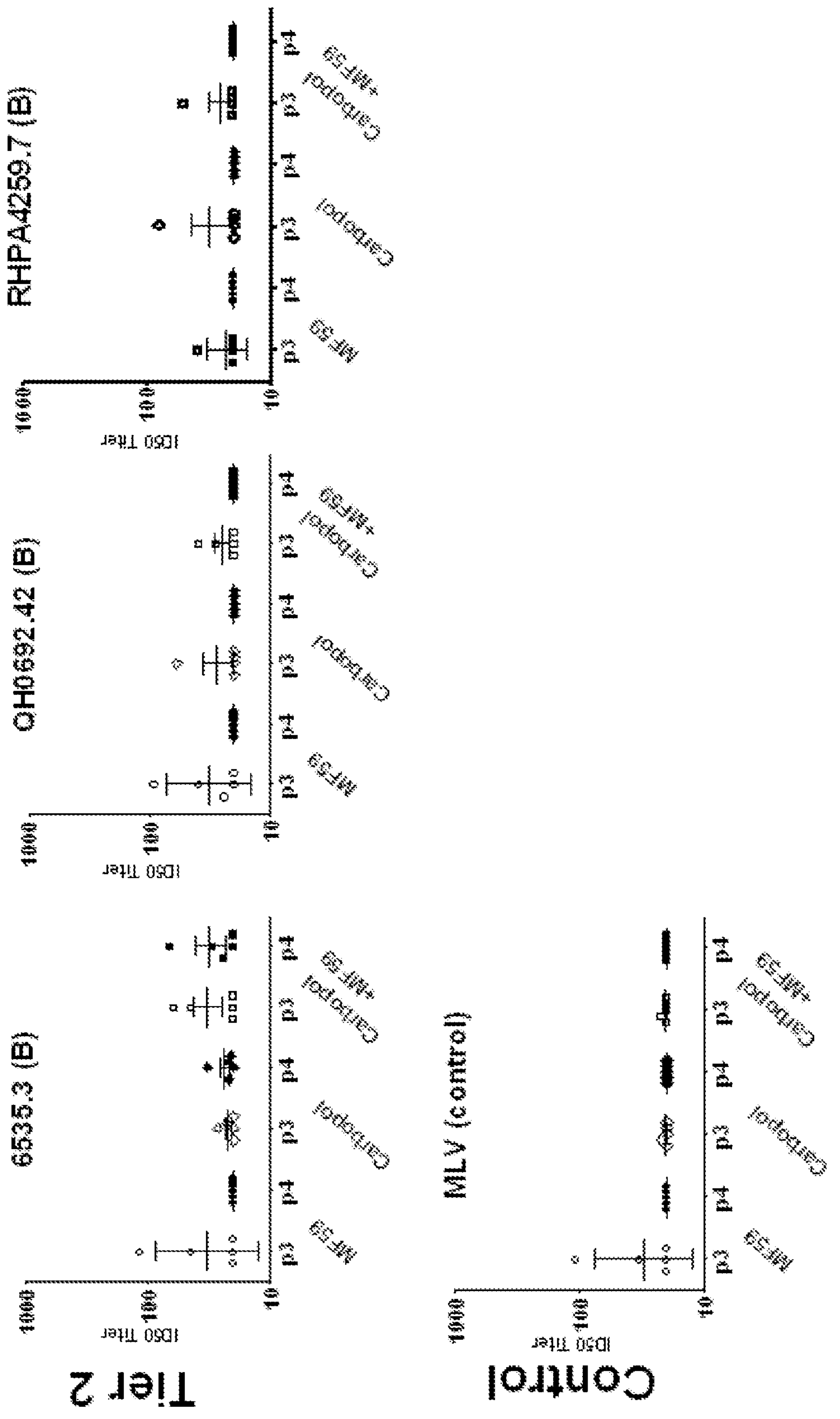

The ability of the Env-specific antibodies generated to neutralize a diverse panel of HIV-1 Env pseudoviruses based on Tiered categorization (See FIGS. 7A and B) was then tested. For most of the pseudovirus neutralization, the 2wp4 (p4) sera were more potent than that from 2wp3 (p3). In comparison to Env administered with MF59™ or complexed with CARBOPOL 971P NF™ alone, Env complexed with CARBOPOL 971P NF™ and adjuvanted with MF59™ was most potent. However, no improvement in breadth of the immune response was observed and only Tier 1A and 1B viruses could be neutralized by the 2wp3/2wp4 vaccine sera (FIG. 7A) from all the comparing groups. MLV neutralization was performed as control (FIG. 7B).

To further assess the 'quality' of humoral immune response elicited post-immunization, the specificity of antibody elicited in the rabbit sera was analyzed using a 'serum mapping' approach described by Y Li et al. (J Virol. 83(2): 1045-59, 2009). Using gp120 mutants (gp120ΔV1V2, gp120ΔV3, gp120D368R—CD4BS mutant, gp120I420R—a CD4i mutant) for differential adsorption of Env-specific antibodies, we found that a majority of the antibodies elicited using the gp140ΔV2 immunogens, either complexed to CARBOPOL 971P NF™, adjuvanted with MF59™, or complexed to CARBOPOL 971P NF™ and adjuvanted with MF59™, were V3-specific. One rabbit in the group immunized with Env adjuvanted with MF59™ elicited CD4BS-antibodies. Other than this single animal, most Env-specific antibodies elicited were primarily directed to the gp120 subunit, and more specifically to the V3-region of the glycoprotein.

In additional immunogenicity experiments, we observed that use of carbopol:Env complex, plus MF59™, with either monovalent (gp120/gp140) Env polypeptide or multivalent (gp120/gp140) Env polypeptide improved the neutralizing breadth and potency of the vaccine (rabbit) sera using both DNA primer-protein boost and protein only regimens. Thus, the improvement in immunogenicity is not dependent upon the state (monomeric or oligomeric) or valency (monovalent or multivalent) of the Env polypeptide.

Example 6

Immunogenicity of HIV-1 Subtype C Env Derived from Different Isolates Alone (Monovalent) or in Combination (Multivalent) Formulated with CARBOPOL 971P NF™ in a DNA Prime-Protein Boost (IM) Regimen This prime-boost study is to compare monovalent gp140 Env polypeptide adjuvanted with MF59™ to multivalent gp140 Env polypeptides adjuvanted with MF59™. This study also compares multivalent gp140 Env polypeptides adjuvanted with MF59™ versus multivalent gp140 Env polypeptides complexed to CARBOPOL™ and adjuvanted with MF59™. The immunogenicity of HIV-1 subtype C gp140 Env derived from different isolates was evaluated in a DNA Prime-Protein boost regimen. The Env polypeptide for the boost immunizations were administered either as monovalent compositions (groups 1-7, and 10) or as multivalent compositions (groups 8 and 9) adjuvanted with MF59™. Group 8 animals were immunized with trivalent gp140 Env polypeptide adjuvanted with MF59™. In comparison, animals in group 9 were immunized with trivalent gp140 Env polypeptide complexed with CARBOPOL 971P NF™ and adjuvanted with MF59™—so this is the CARBOPOL™+ MF59™ group. For the multivalent/trivalent group, 50 μg (8.3+8.3+8.3 μgs of each Env polypeptide) of total Env polypeptide was administered.

TABLE 3

Immunization Study design of DNA prime-protein boost (IM) in rabbits of HIV-1 subtype C gp140 derived from different isolates and formulated with MF59 (TM) (for all monovalent group) and comparison of multivalent Env polypeptides with and without CARBOPOL 971P NF(TM)

| Group | DNA Prime (weeks 0, 4; dose - 1 mg) | Protein Boost (weeks 12, 24, 34; dose - 25 μg) |
|---|---|---|
| 1 | Du422.1 | Du422.1 |
| 2 | Du156.12 | Du156.12 |
| 3 | CAP45 | CAP45 |
| 4 | ZM249M.PL1 | ZM249M.PL1 |
| 5 | HIV-25711-2 | HIV-25711-2 |
| 6 | CAP255 | CAP255 |
| 7 | CAP239 | CAP239 |
| 8* | ZM249M.PL1 + CAP239 + Du422.1 | ZM249M.PL1 + CAP239 + Du422.1 |
| 9* | ZM249M.PL1 + CAP239 + Du422.1 | ZM249M.PL1 + CAP239 + Du422.1 # |
| 10 | TV1 | TV1 |

5 rabbits/group; IM immunizations (DNA and protein)
DNA prime: 1 mg/dose at weeks 0 and 4
Protein boost: 25 μg with MF59/dose at weeks 12, 24, and 34
*Equal composition of each Env in DNA prime and protein boost
Protein boost adjuvanted with MF59(TM) + CARBOPOL 971P NF(TM)

Neutralization breadth after vaccination with HIV-1 subtype C gp140 Env polypeptide formulated in MF59™ only, i.e., without CARBOPOL 971P NF™ (except for group 9) in Rabbits for Tier 1a and Tier 1b as well as for Tier 2 (pseudo-) viruses using sera collected at two weeks post fourth (2wp4) immunization are shown in FIGS. 8A and B. In particular, FIG. 8 shows the results as a heat map showing breadth and potency (in ID50 titers) of serum neutralization of HIV-1 pseudoviruses. The breadth and potency of serum neutralization of HIV-1 pseudoviruses was assessed as follows. Sera were analyzed 2 weeks post 4th immunization. Sera from each rabbit within groups were tested against the tiered (Tier 1a, Tier 1b and Tier 2) virus panel of SF162, MN.3, Ba1.26, Du156.12, Du422.1, ZM249M.PL1, MW965.26, TV1c21 and CAP239 in a single-cycle TZM-b1 pseudovirus assay. Neutralization was assessed using molecularly cloned pseudoviruses and a luciferase reporter gene assay in TZM-b1 cells. Briefly, a total of 200 TCID50 pseudovirus/well were added to diluted sera samples and incubated at 37° C. for 1 hour. Following incubation, 10,000 cells/well in DEAE-dextran-containing media were added and incubated for 48 hrs at 37° C. The final concentration of DEAE-dextran was 10 μg/ml. Single round of infection HIV-1 Env pseudoviruses were prepared by co-transfection of 293T cells with an envelope expression plasmid containing a full-length gp160 env gene along with an env-deficient HIV-1 backbone vector (pSG3Δenv), using TransIT®-LT1 transfection reagent (Mirus Bio Corp., Madison, Wis.). After 48 hrs, the cell culture supernatant containing the pseudovirus was filtered through a 0.45 μm filter. Neutralizing activity was measured as reductions in luciferase gene expression. The percent reduction in relative luminescence units (RLU) was calculated relative to the RLU in the presence of pre-immunization serum. Neutralizing antibody titers against SF162 strain were determined using 3-fold serially diluted sera samples. The breadth of neutralizing antibodies in sera was assessed at a serum dilution of 1:20. The percent neutralization was corrected for non-specific inhibition using the formula described previously with MLV as a control virus.

Potent neutralization of Subtype C Tier 1a MW965.26 pseudovirus, appreciable neutralization of Subtype B Tier 1a pseudoviruses, and poor neutralization of Tier 1b pseudoviruses was observed. The multivalent/trivalent arm (group 8) showed no distinct advantage in neutralizing ID50 titer over single envelope antigens however the CARBOPOL 971P NF™+MF59™ adjuvant arm (group 9) showed enhanced potency.

Figure 9A:
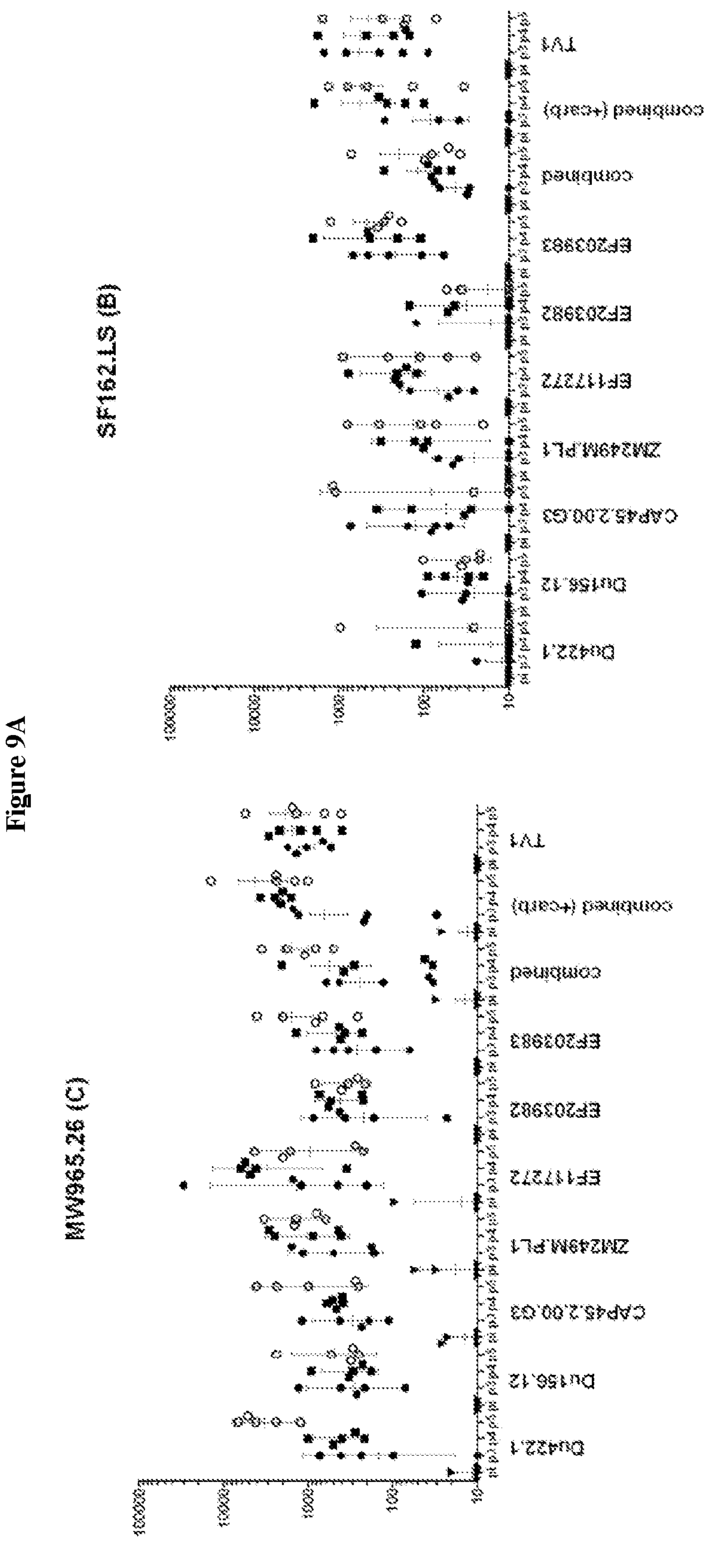
FIGS. 9A-E show neutralization ID50 titers of against various isolates.
Figure 9B:
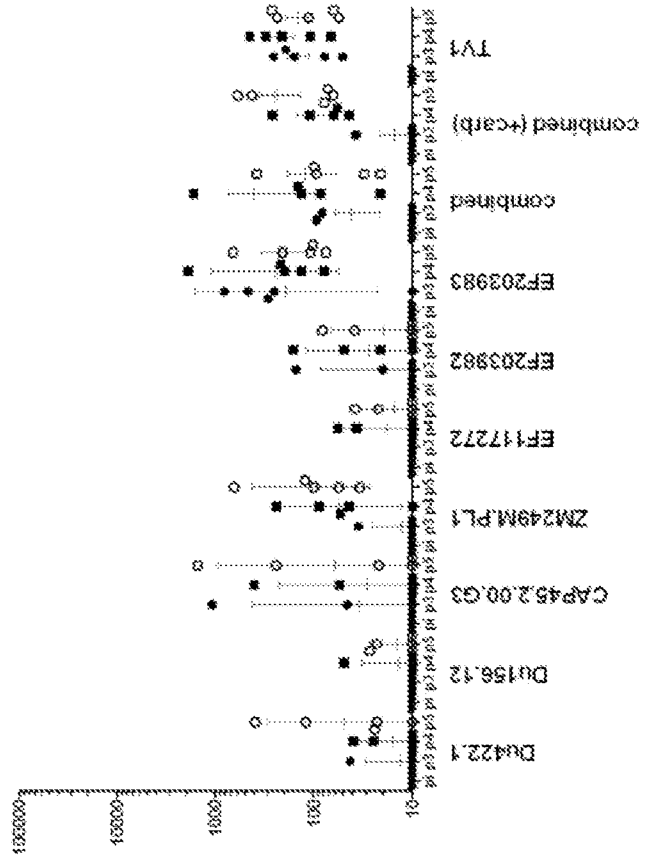
Figure 9C:
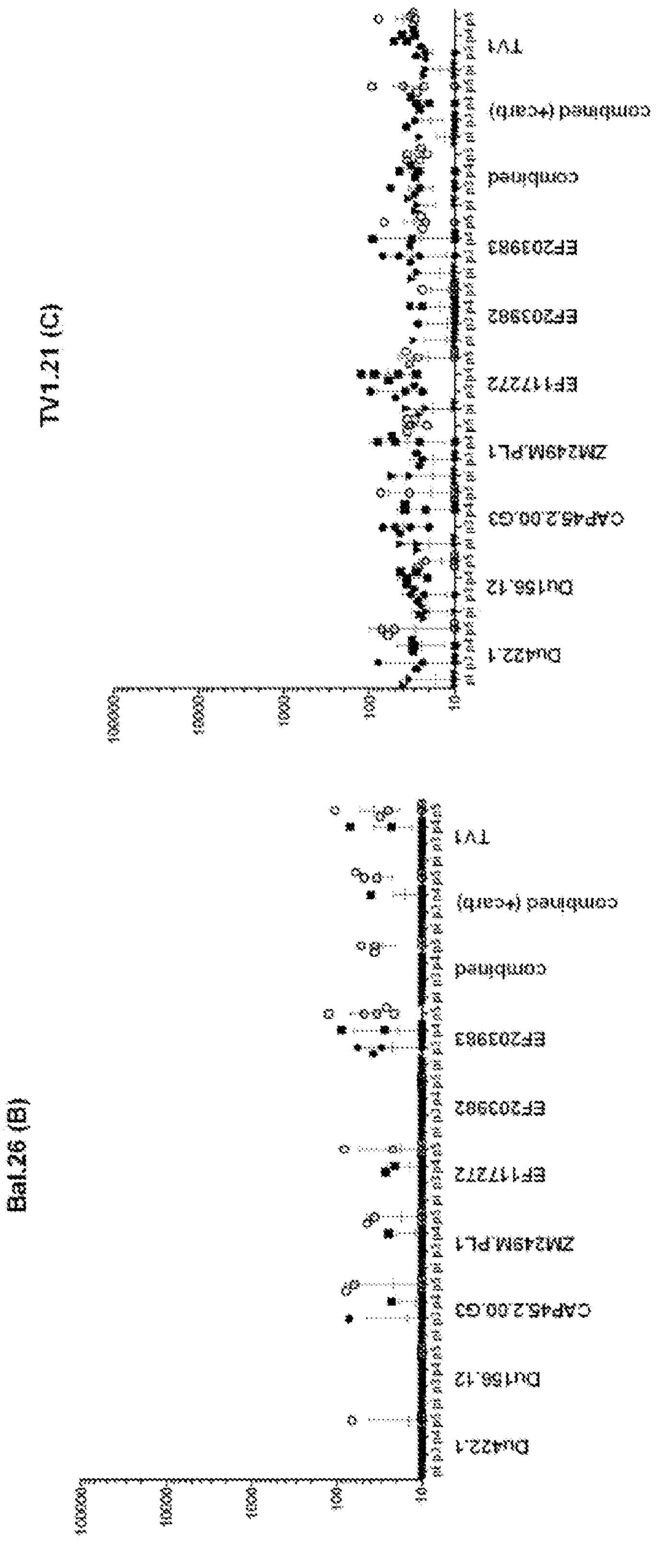
Figure 9D:
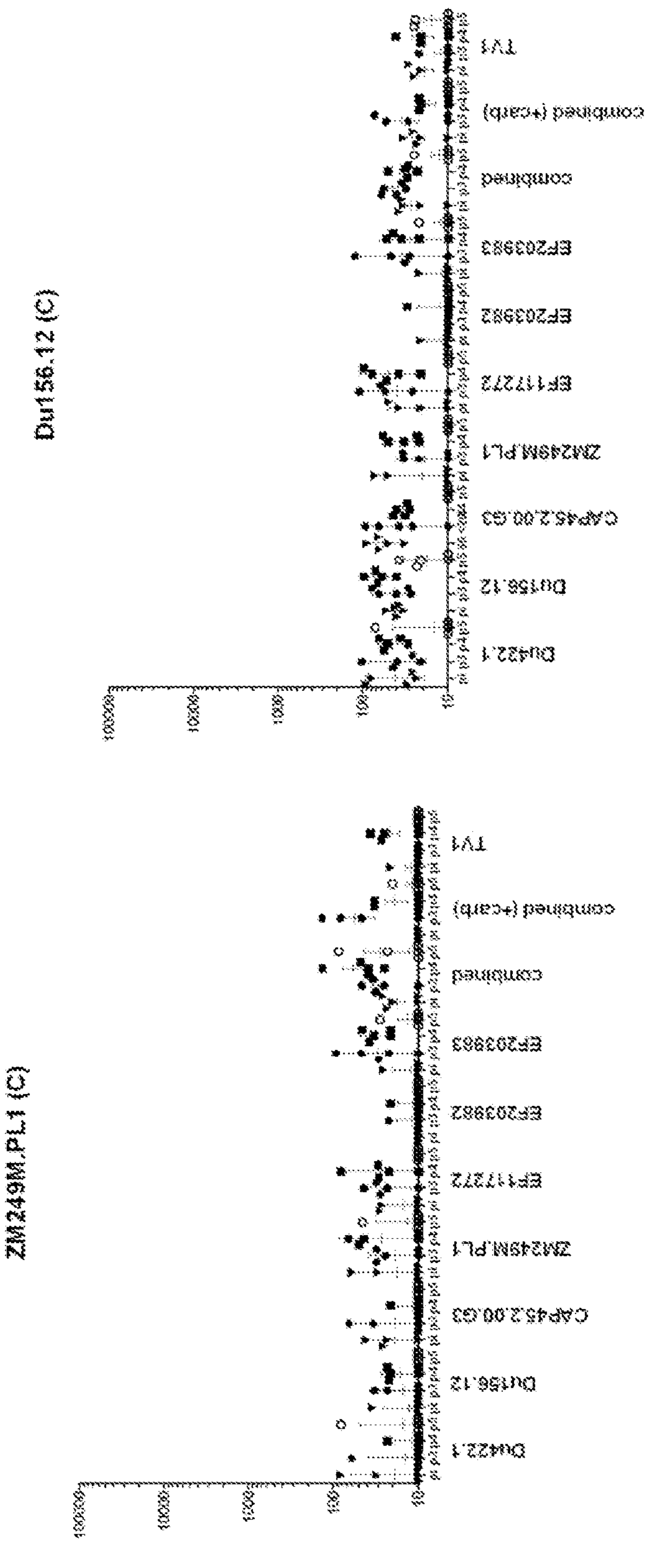
Figure 9E:
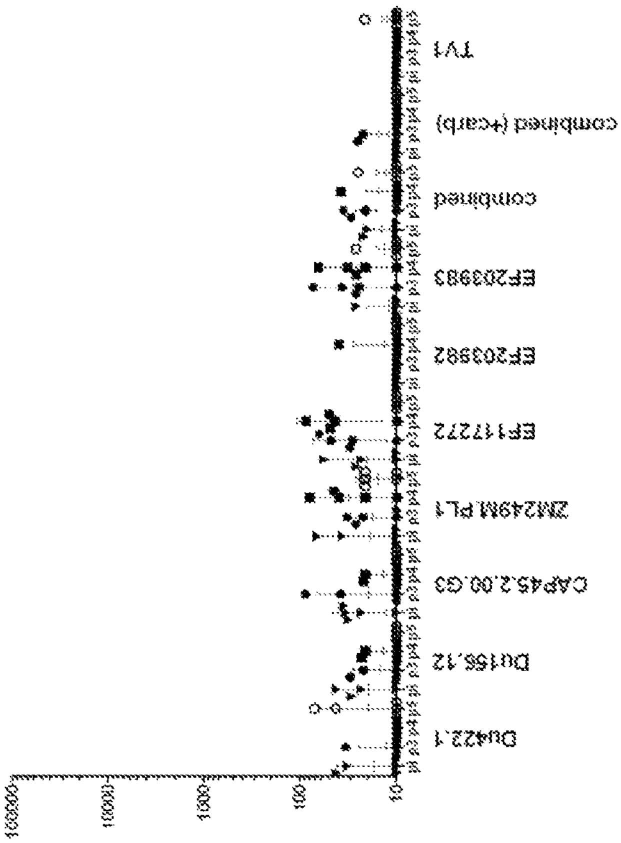

Neutralization ID50 titers of Tier 1 isolates (2wp3 (p3), 2wp4 (p4), & 2wp5 (p5)): The fifth immunization did not improve titers in most cases as shown in FIGS. 9A, B (Tier 1a) and C (Tier 1b) or in no cases for Tier 2, respectively (FIGS. 9D and E).

Figure 10:
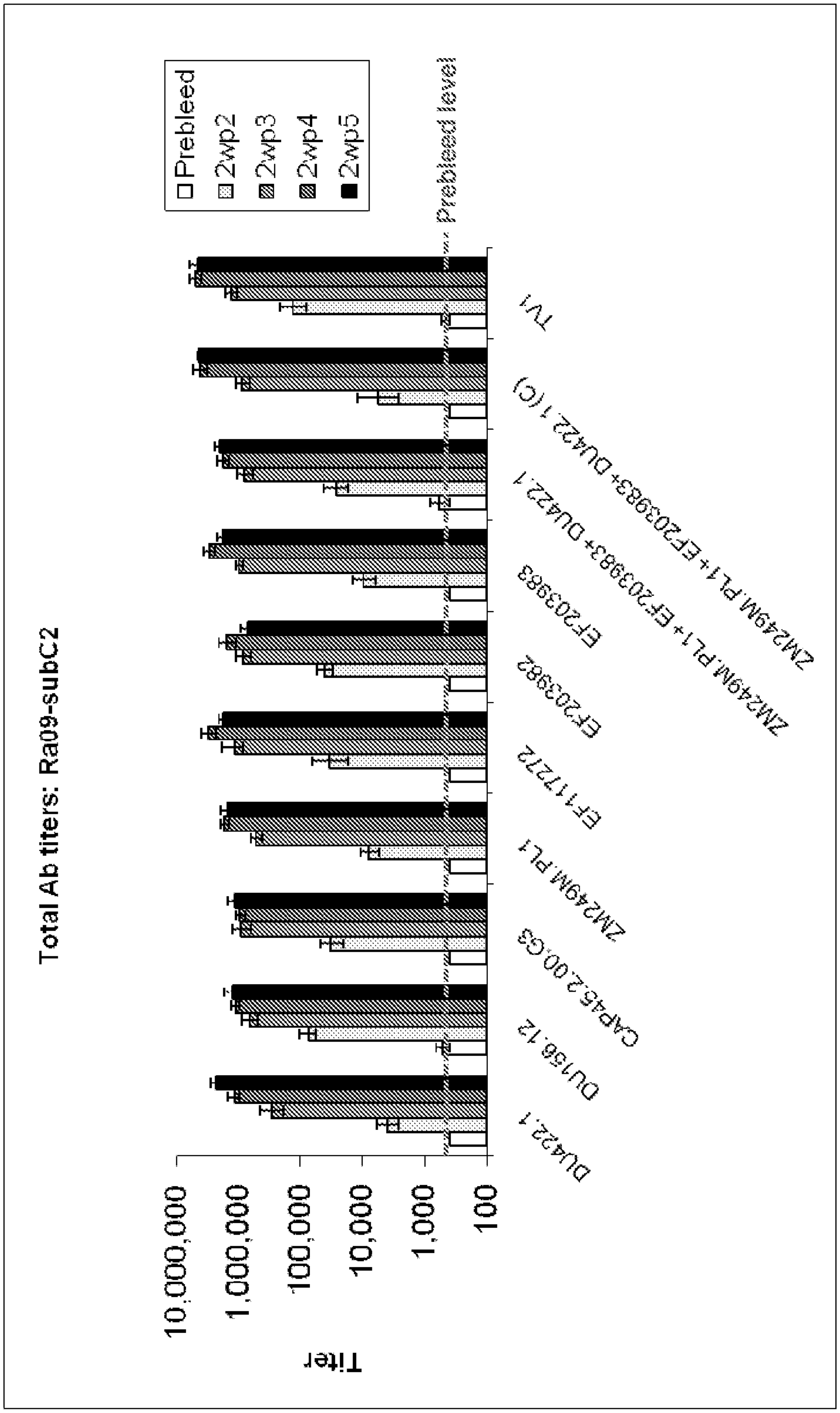
FIG. 10 shows total antibody-binding titers against TV1 gp140 Env polypeptide as measured by gp120-binding ELISA. The background titer for the prebleeds (as control) is also included. The antibody titers were determined by ELISA using TV1 gp140 Env polypeptide as the coating protein. The data values shown represent geometric mean titers (GMT) of five rabbits individually assayed in triplicates per group.

FIG. 10 shows total antibody-binding titers against TV1 gp140 Env polypeptide as measured by gp120-binding ELISA. The background titer for the prebleeds (as control) is also included. The antibody titers were determined by ELISA using TV1 gp140 Env polypeptide as the coating protein. The data values shown represent geometric mean titers (GMT) of five rabbits individually assayed in triplicates per group. All antigens elicited robust antibody geometric mean titers (GMT), with peak GMT for all antigens exceeding $10^6$.

Figure 11:
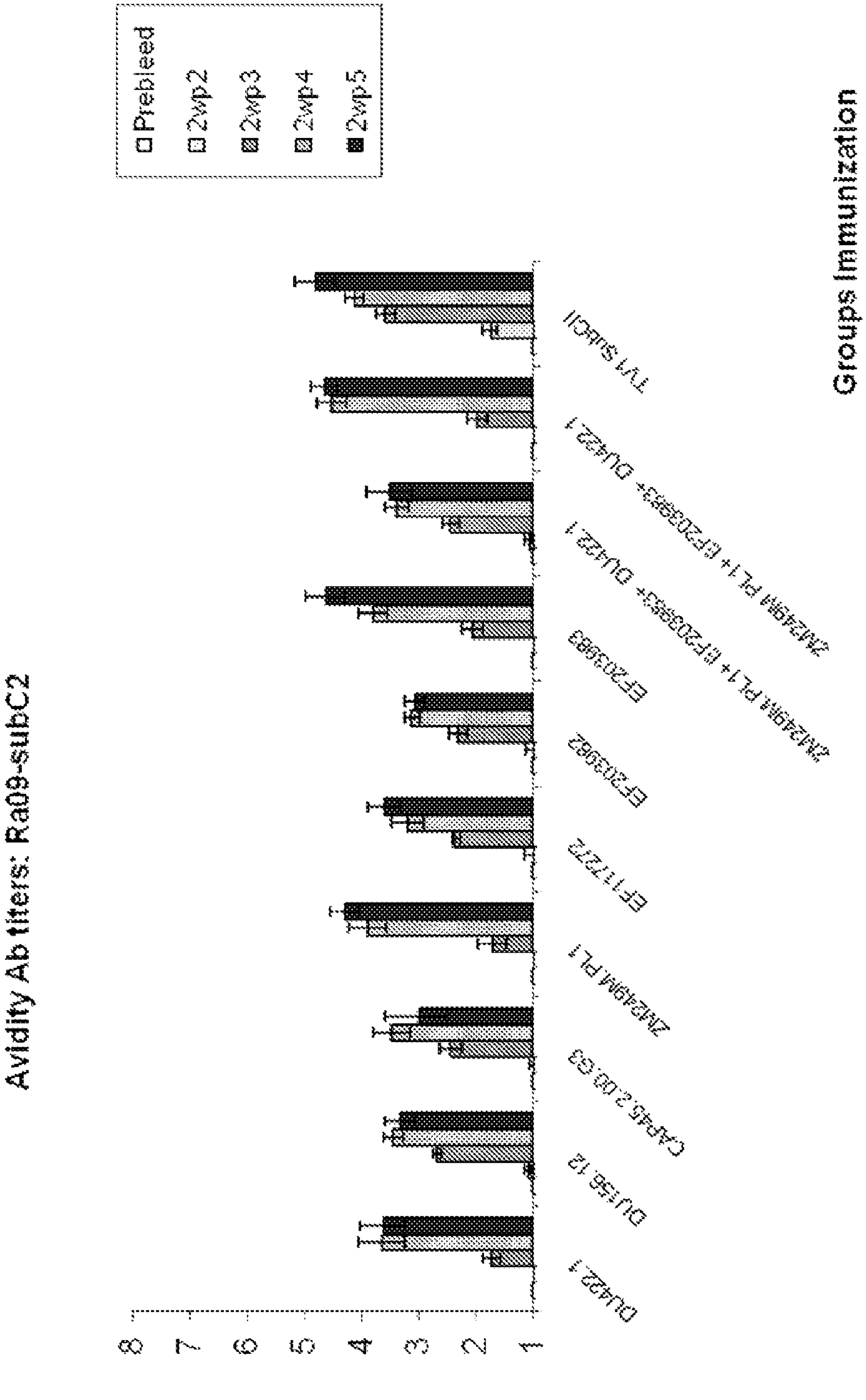
FIG. 11 shows antibody avidity of sera collected from all ten groups of rabbits from Example 6 that were immunized with Env polypeptide, either monovalent or multivalent, adjuvanted with MF59™ (and in one case with MF59™ and CARBOPOL™). The groups are from left to right: Du422.1 gp140, Du156.12 gp140, CAP45 gp140, ZM249M.PL1 gp140, HIV-25711-2 (EF117272) gp140, CAP255 (EF203982) gp140, CAP239 (EF203983) gp140, ZM249M.PL1 gp140+CAP239 (EF203983) gp140+ Du422.1 gp140 (with MF59™ only), ZM249M.PL1 gp140+ CAP239(EF203983) gp140+Du422.1 gp140 (with MF59™ and CARBOPOL™), and TV1 gp140. The avidity for each group is shown (from left to right) in increasing shades of grey for prebleed, two-weeks post second immunization (2wp2), two-weeks post third immunization (2wp3), two-weeks post fourth immunization (2wp4), and two-weeks post fifth immunization (2wp5). Avidity was determined by $NH_4SCN$ displacement ELISA using TV1 gp140 Env polypeptide as the coating antigen as described by I. K. Srivastava et al. (J. Virol. 2002).

The antibody avidity was evaluated for sera collected from all groups (FIG. 11). Avidity was determined by $NH_4SCN$ displacement ELISA using TV1c8.2 rgp140-o as the coating antigen as described by I. K. Srivastava et al. (J. Virol. 2002).

Example 7

Immunogenicity of CARBOPOL 971P NF™:gp140 Env Polypeptide Complexes in Rabbits in Protein Only (IM) Regimen This study, in contrast to studies in Examples 5 and 6, is a protein only study. Examples 5 and 6 show that in both monovalent and multivalent Env polypeptide immunizations in DNA prime-protein boost regimen that CARBOPOL 971P NF™+MF59™ was more effective. This study demonstrates that CARBOPOL 971P NF™+MF59™ was equally effective in protein-only regimen and there is no difference in multivalent immunizations when either co-administered or given sequentially.

Immunization of rabbits with HIV-1 subtype C gp140 Env polypeptide formulated with CARBOPOL 971P NF™+ MF59™ (see Table 4). 25 μg of each individual gp140 Env polypeptide from the isolates listed in Table 4 (all groups except 8) was administered per rabbit. For group 8, 6.25 μg of gp140 Env polypeptide from each strain was combined to give a final dose of 25 μg gp140 Env polypeptide. For each group, five New Zealand White rabbits were used in this immunogenicity study. Env polypeptide were administered in complex with CARBOPOL 971P NF™ adjuvanted with MF59™. Serum samples were collected prior to first immunization (pre-bleed) and two weeks following each immunization.

TABLE 4

Immunization study design of HIV-1 subtype C gp140Env formulated with CARBOPOL 971P NF(TM) + MF59(TM) in Rabbits

| Group | Protein Only (weeks 0. 4, 12, 24; dose - 25 μg) |
|---|---|
| 1 | Du156.12 gp140 |
| 2 | Du422.1 gp140 |
| 3 | ZM249M.PL1 gp140 |
| 4 | CAP239 gp140 |
| 5 | TV1 gp140 |
| 6 | TV1 gp140 ΔV2 |
| 7 | SF162 gp140 ΔV2 |
| 8* | ZM249M.PL1 + CAP239 + Du422.1 + TV1 gp140 |
| 9# | CAP239 gp140/Du422.1 gp140/ZM249M.PL1 gp140/TV1 gp140 |

Protein: 25 μg with MF59 and CARBOPOL 971P NF(TM)/dose at weeks 0, 4, 12 and 24
*Equal composition of each Env polypeptide (6.25 μg each)
#Sequential immunization: 25 μg single Env polypeptide immunization
5 rabbits/group; IM immunizations (protein only)

The neutralization breadth (in ID50 titers) was determined after vaccination with HIV-1 subtype C gp140Env formulated with CARBOPOL 971P NF™+MF59™ for all groups with sera collected at 2wp3 (see FIGS. 12A and B). Sera were tested against the HIV-1 subtype C Tier 1a, b and Tier 2 pseudovirus panels in a single-cycle TMZ-b1 pseudovirus assay, as described above. As shown in FIG. 12, 2wp3 sera readily neutralized Tier 1a viruses, but mostly failed to neutralize Tier 1b or Tier 2 viruses. Multivalent or sequential immunization of gp140 Env polypeptides did not improve the overall immune response.

The neutralization breadth (in ID50 titers) was determined after vaccination with HIV-1 subtype C gp140 Env polypeptide formulated with CARBOPOL 971P NF™+MF59™ for all groups with sera collected at 2wp4 (see FIGS. 13A, B and C). Sera were tested against an extended HIV-1 subtype B and C virus panel in a single-cycle TMZ-b1 pseudovirus assay, as described above. As observed, at 2wp4, serum was more potent and neutralized majority of the Tier 1a and Tier 2a viruses (although with lower ID50 titers). Some low neutralization of Tier 2 viruses was also observed. Overall, 2wp4 sera provided better neutralization than 2wp3 sera (compare FIGS. 12 and 13), emphasizing the need for a secondary protein boost.

Figure 14A:
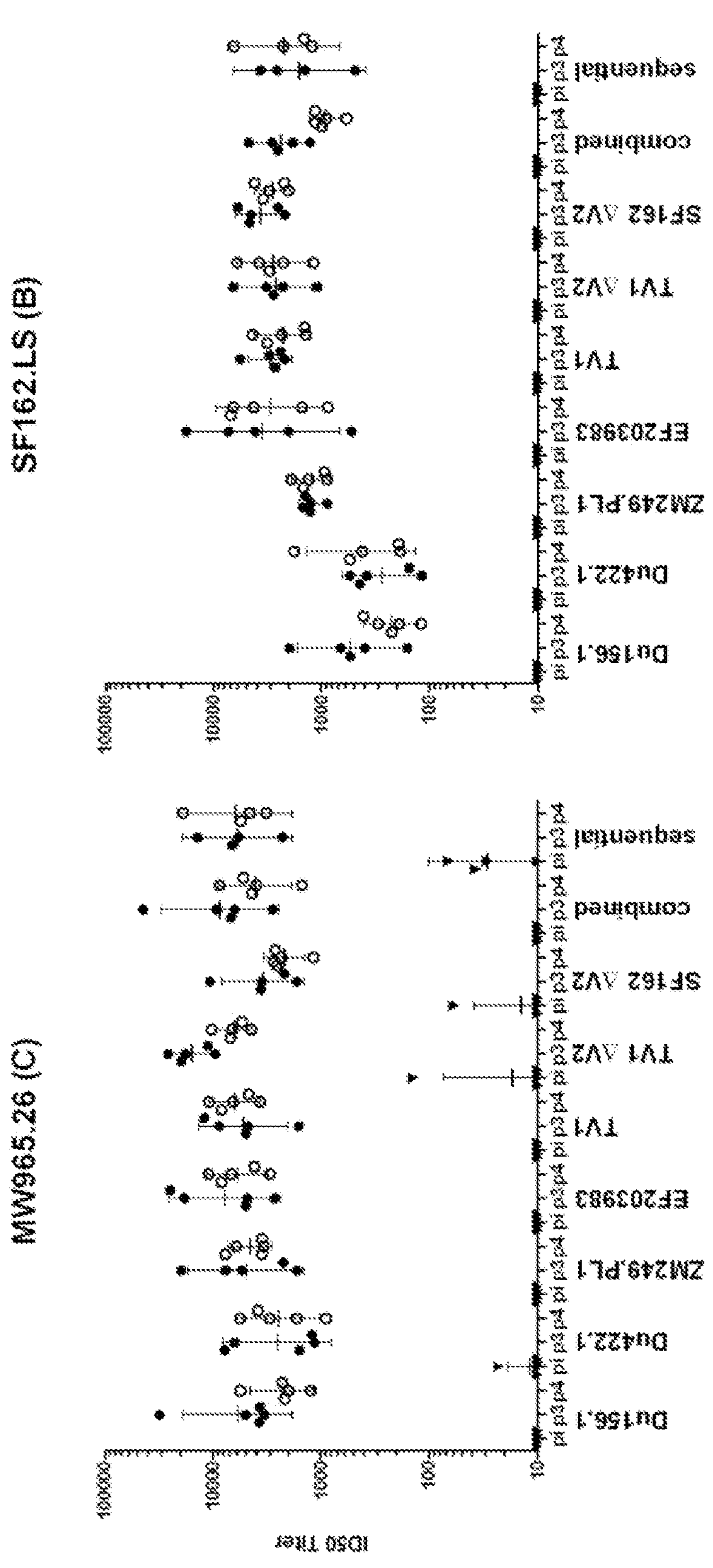
FIGS. 14A-E shows ID50 neutralization titers of sera obtained two weeks post third immunization (p3) and two weeks post fourth (p4) immunization, as determined using a HIV-1 pseudovirus assay.
Figure 14B:
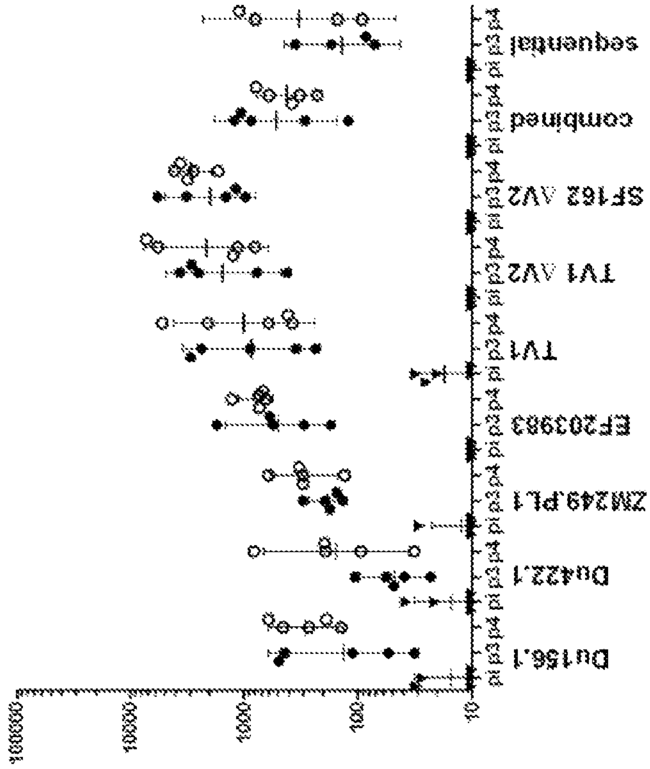
Figure 14C:
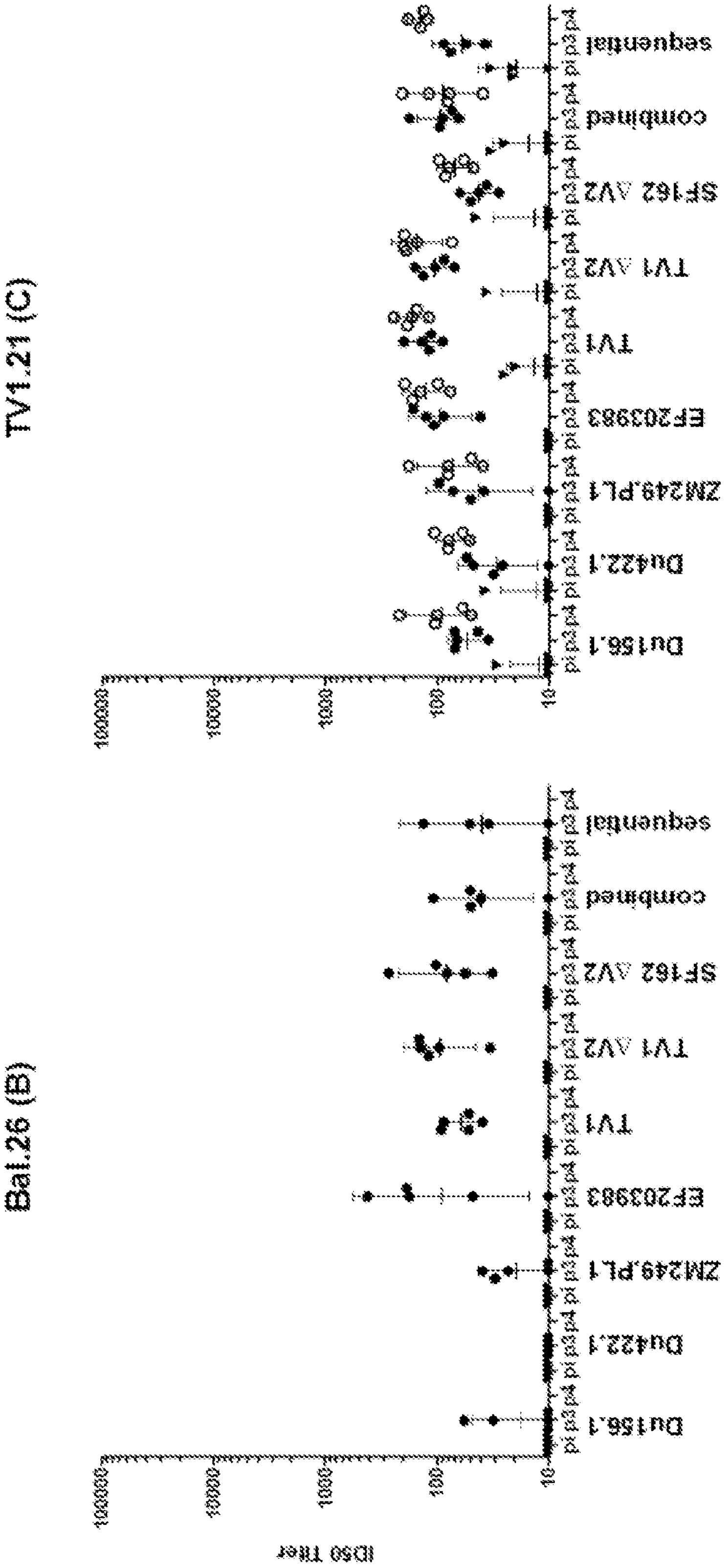
Figure 14D:
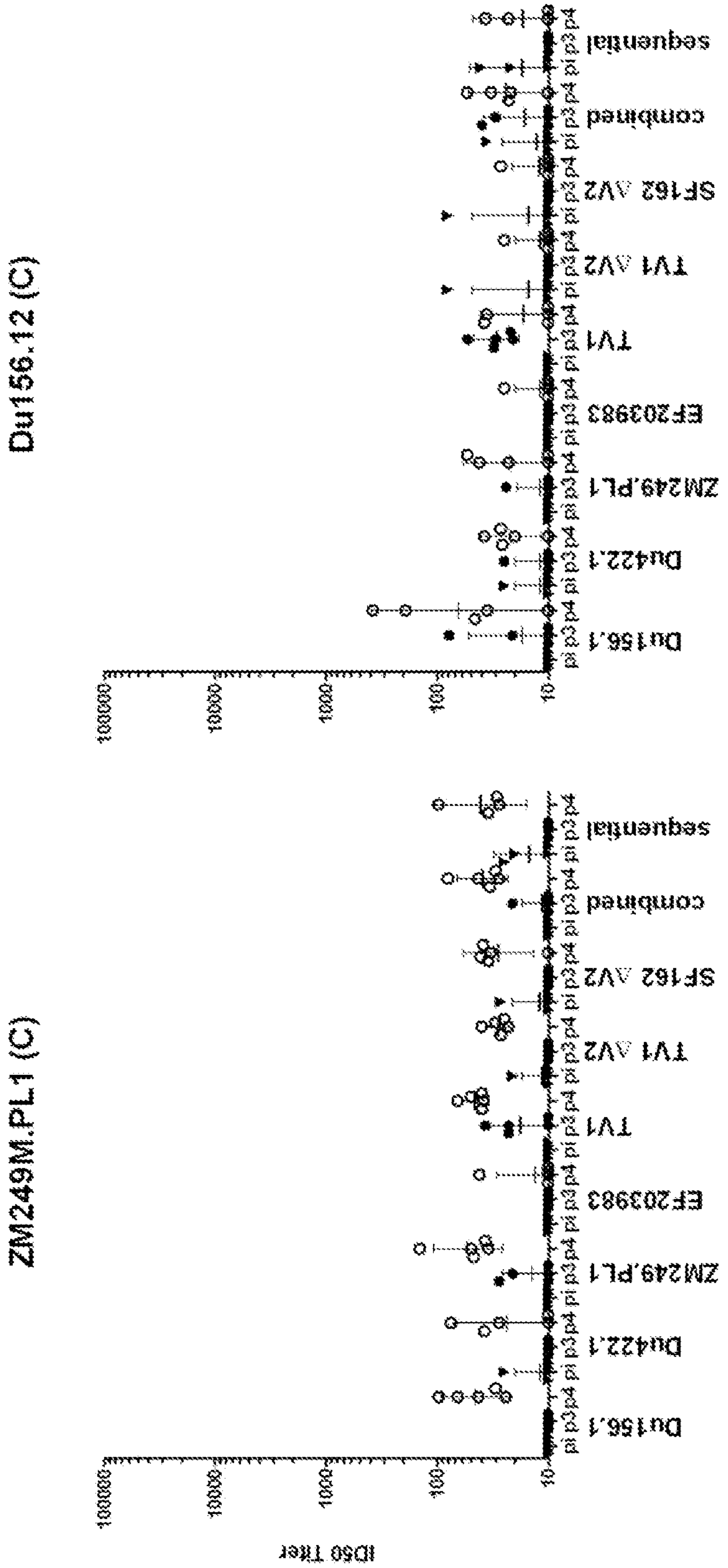
Figure 14E:
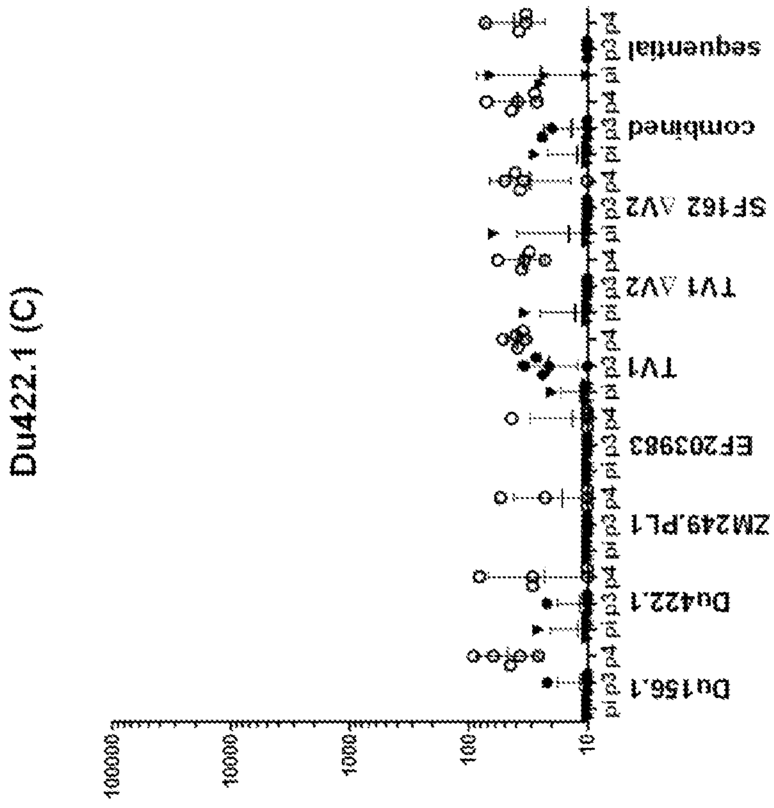

Potent neutralization of Tier 1 isolates post $3^{rd}$ and $4^{th}$ immunization (Tier 1a: FIGS. 14A-B; Tier 1b: FIG. 14C). The fourth immunization increased titers against Tier 1b TV1.21 virus. Tier 2: FIGS. 14D-E in a single-cycle TMZ-b1 pseudovirus assay, as described above.

Figure 15:
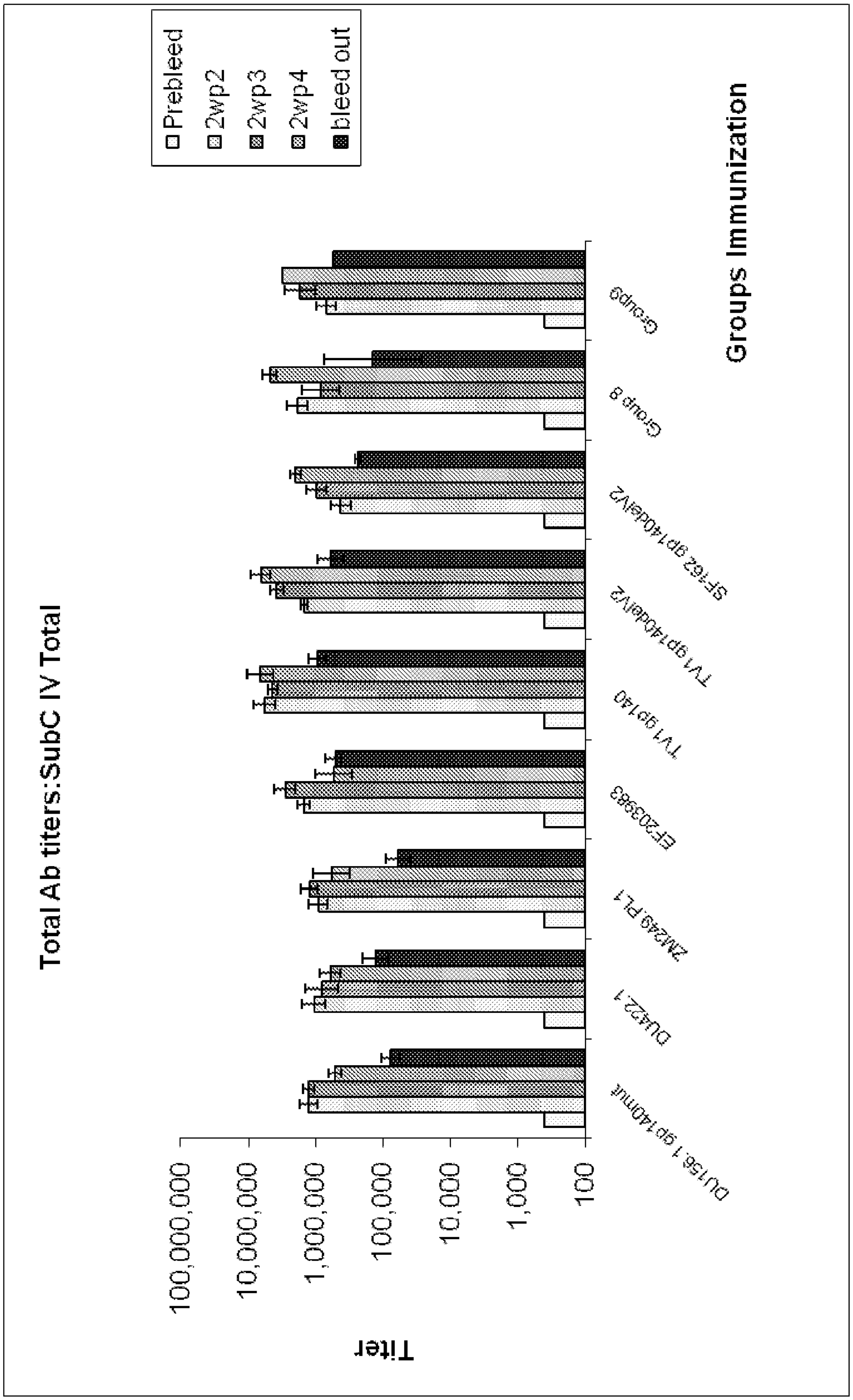
FIG. 15 shows binding-antibody titers for rabbit sera collected from all nine groups measured with gp120-binding ELISA (geometric mean titer—y axis). The groups are from left to right: The groups are from left to right: Du156.12 gp140, Du422.1 gp140, ZM249M.PL1 gp140, CAP239 gp140, TV1 gp140, TV1 gp140ΔV2, SF162 gp140ΔV2, ZM249M.PL1 gp140+CAP239 gp140+Du422.1 gp140+ TV1 gp140 (group 8, multivalent administration), and CAP239 gp140/Du422.1 gp140/ZM249M.PL1 gp140/TV1 gp140 (group 9, sequential administration). The geometric mean titer for each group is shown (from left to right) in increasing shades of grey for prebleed, two-weeks post second immunization (2wp2), two-weeks post third immunization (2wp3), two-weeks post fourth immunization (2wp4), and bleed out.

Evaluation of total antibody titers was performed by ELISA using TV1 gp140 Env polypeptide as the coating antigen as described by I. K. Srivastava et al. (J. Virol. 2002). (FIG. 15—Group 8 (multivalent): ZM249M.PL1+CAP239+Du422.1+TV1 gp140; Group 9 (sequential): CAP239 gp140/Du422.1 gp140/ZM249M.PL1 gp140/TV1 gp140).

Figure 16:
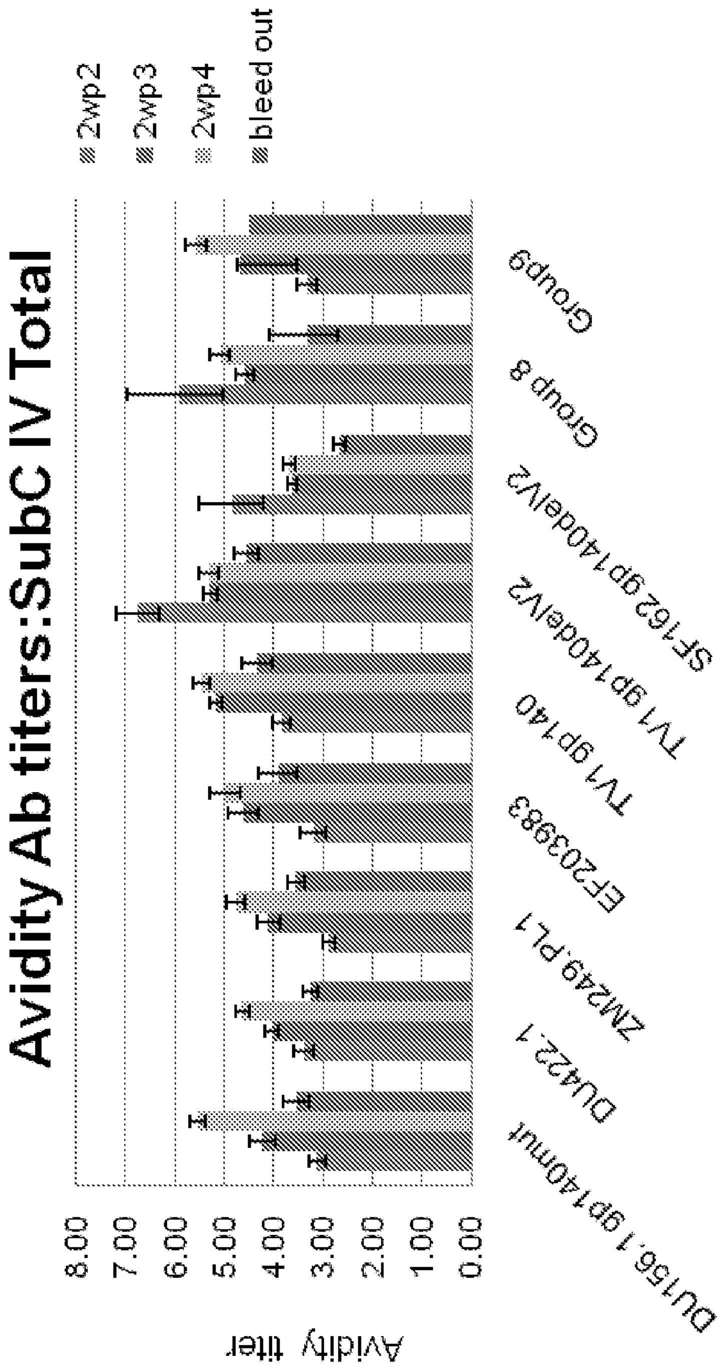
FIG. 16 shows antibody avidity of rabbit sera collected from all nine groups. The groups are from left to right: Du156.12 gp140, Du422.1 gp140, ZM249M.PL1 gp140, CAP239 gp140, TV1 gp140, TV1 gp140ΔV2, SF162 gp140ΔV2, ZM249M.PL1+CAP239+Du422.1+TV1 gp140 (group 8), and CAP239 gp140/Du422.1 gp140/ ZM249M.PL1 gp140/TV1 gp140 (group 9). The avidity index for each group is shown (from left to right): two-weeks post second immunization (2wp2), two-weeks post third immunization (2wp3), two-weeks post fourth immunization (2wp4), and bleed out. Avidity was determined by NH4SCN displacement ELISA using TV1 gp140 Env polypeptide as the coating antigen as described by I. K. Srivastava et al. (J. Virol. 2002).
Figure 17A:
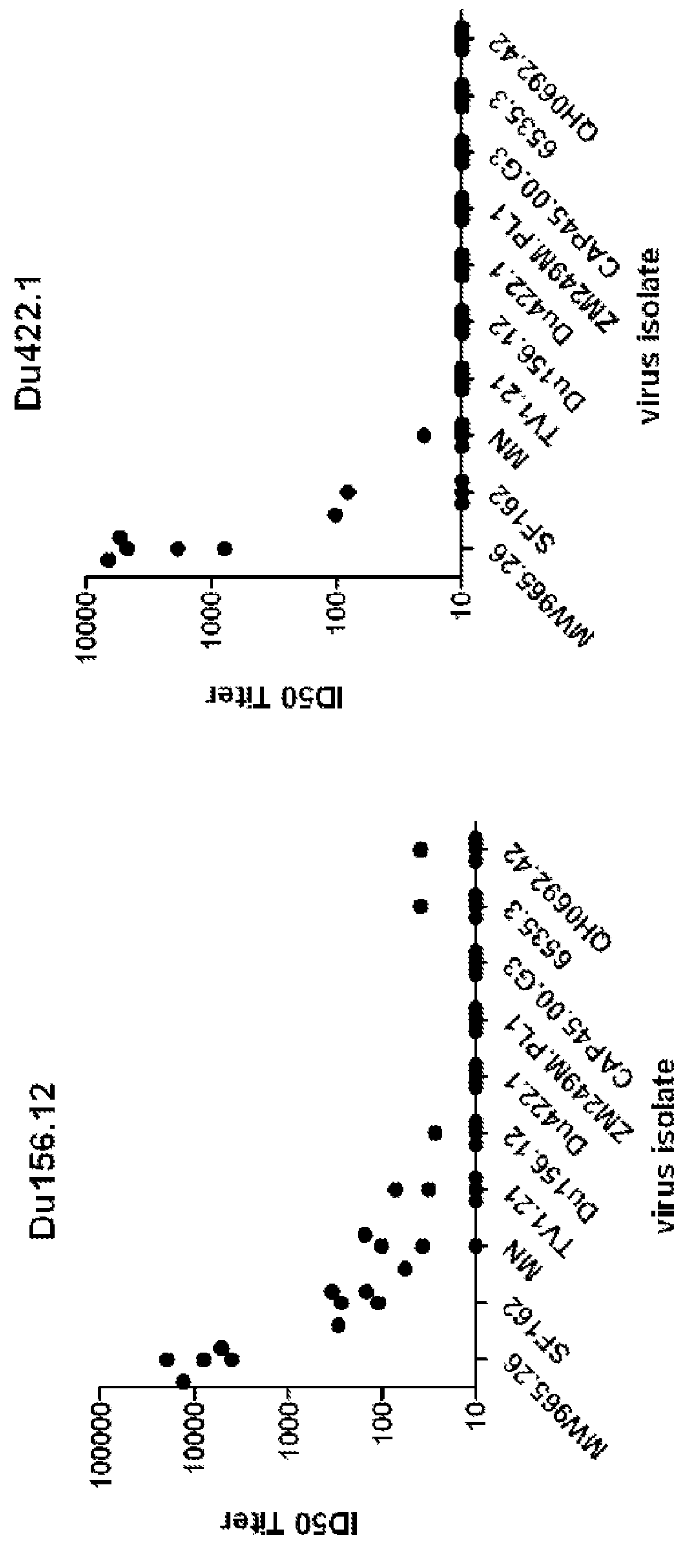
Figure 17B:
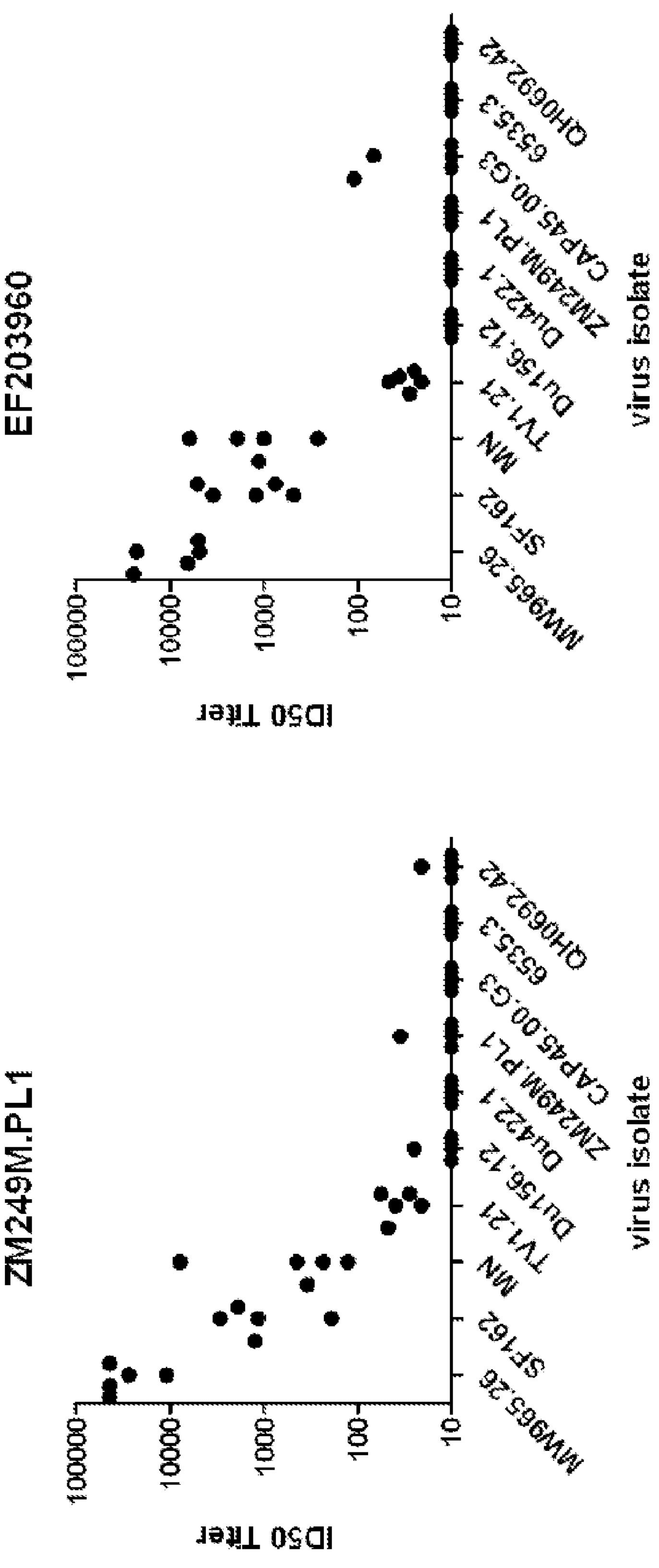
Figure 17D:
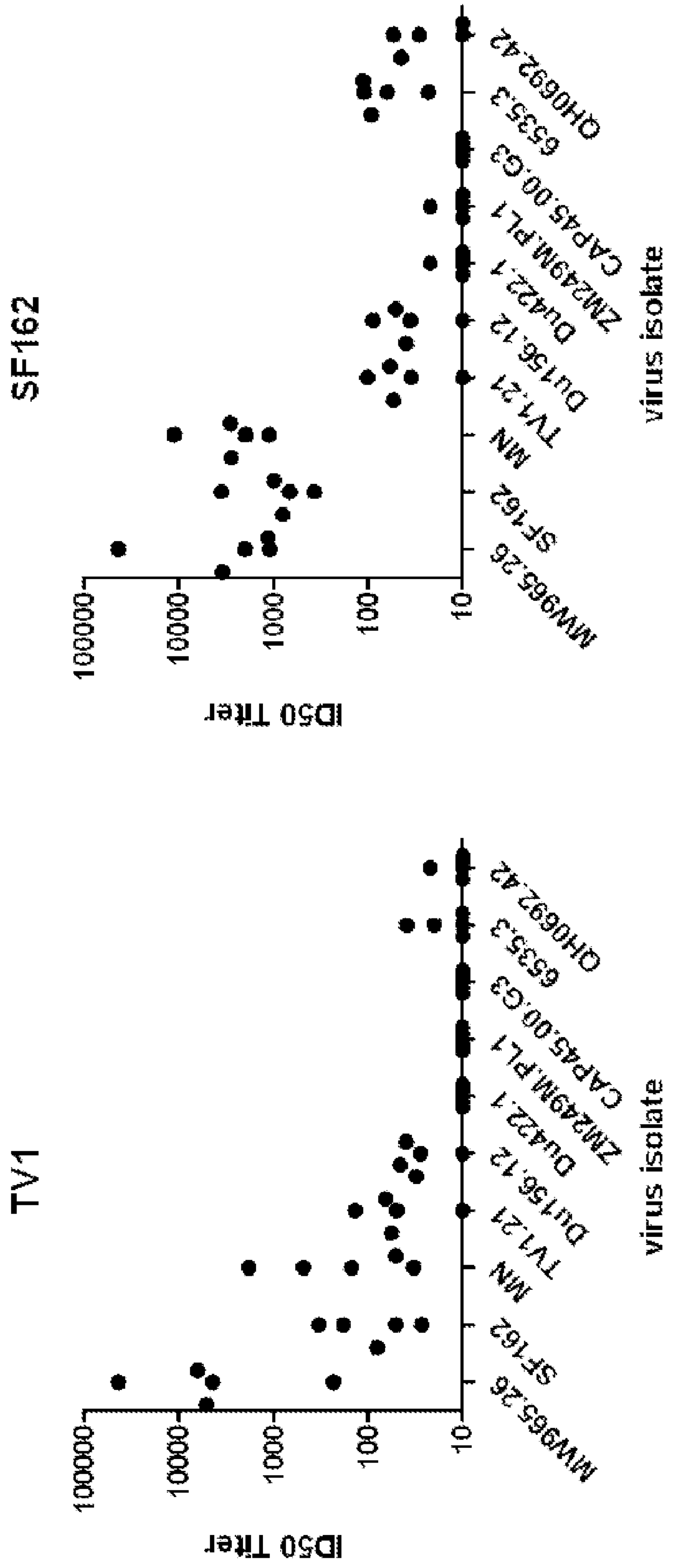
Figure 17E:
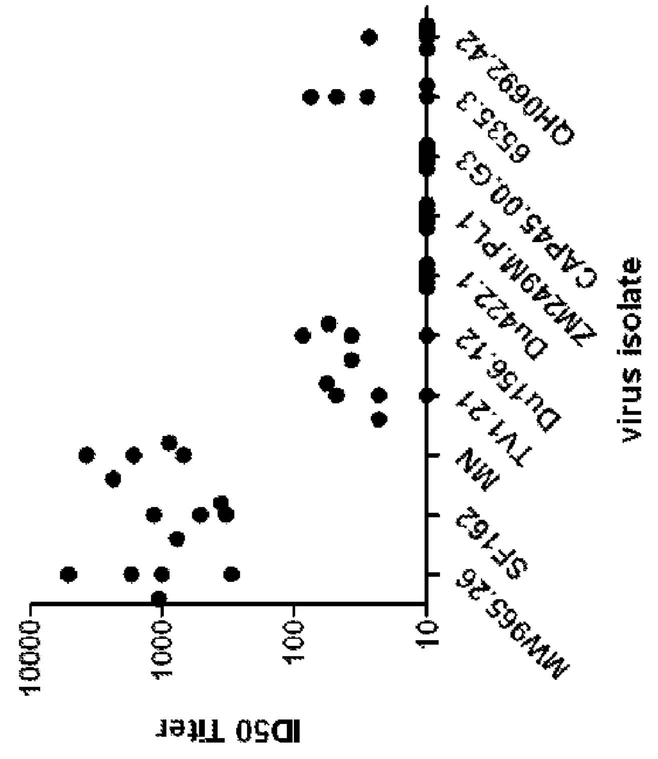
Figure 17E:
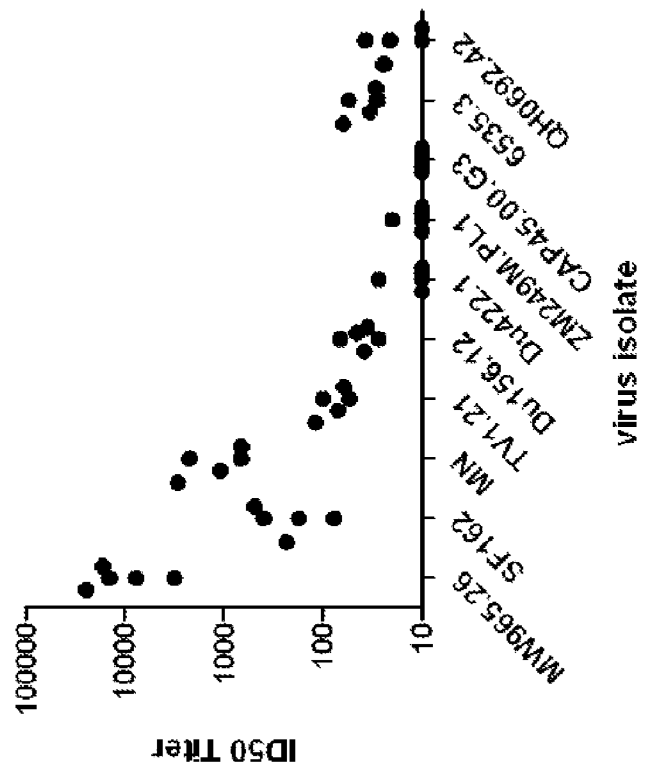
Figure 17F:
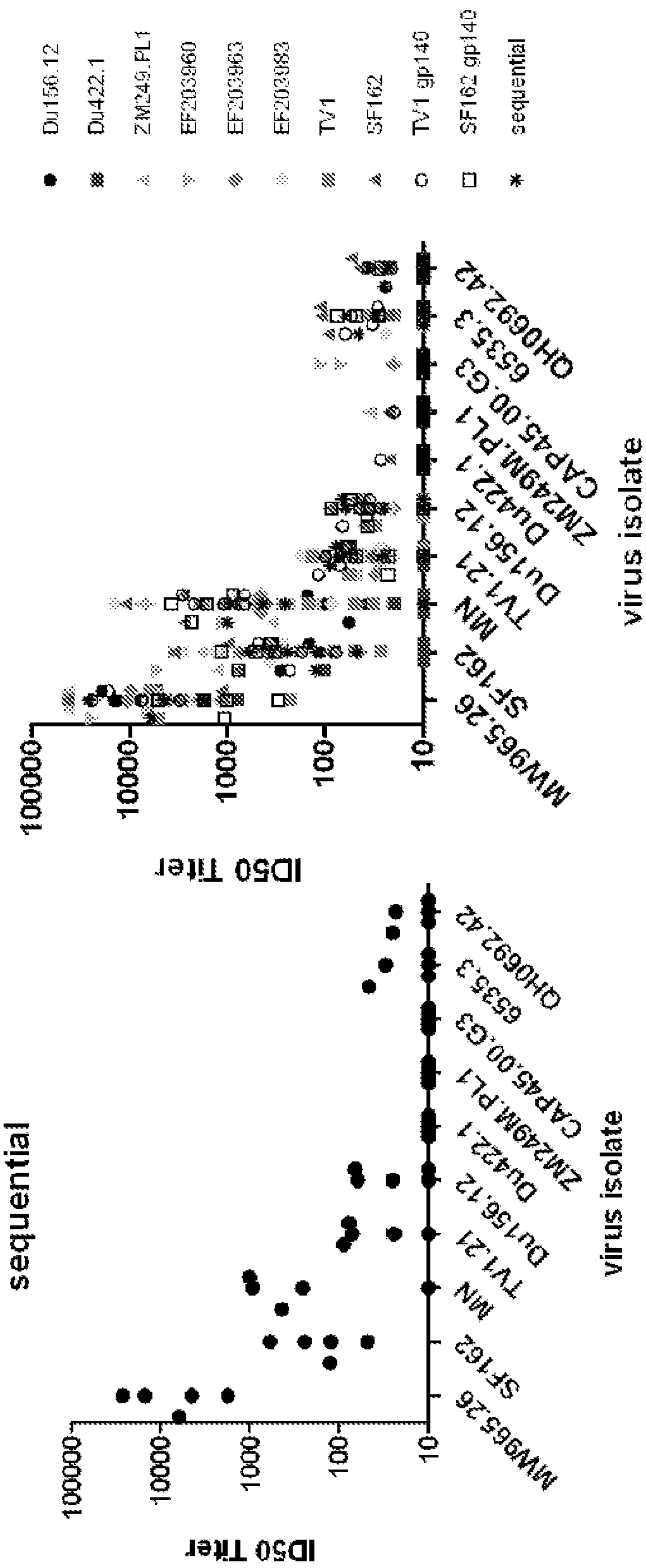
Figure 20A:
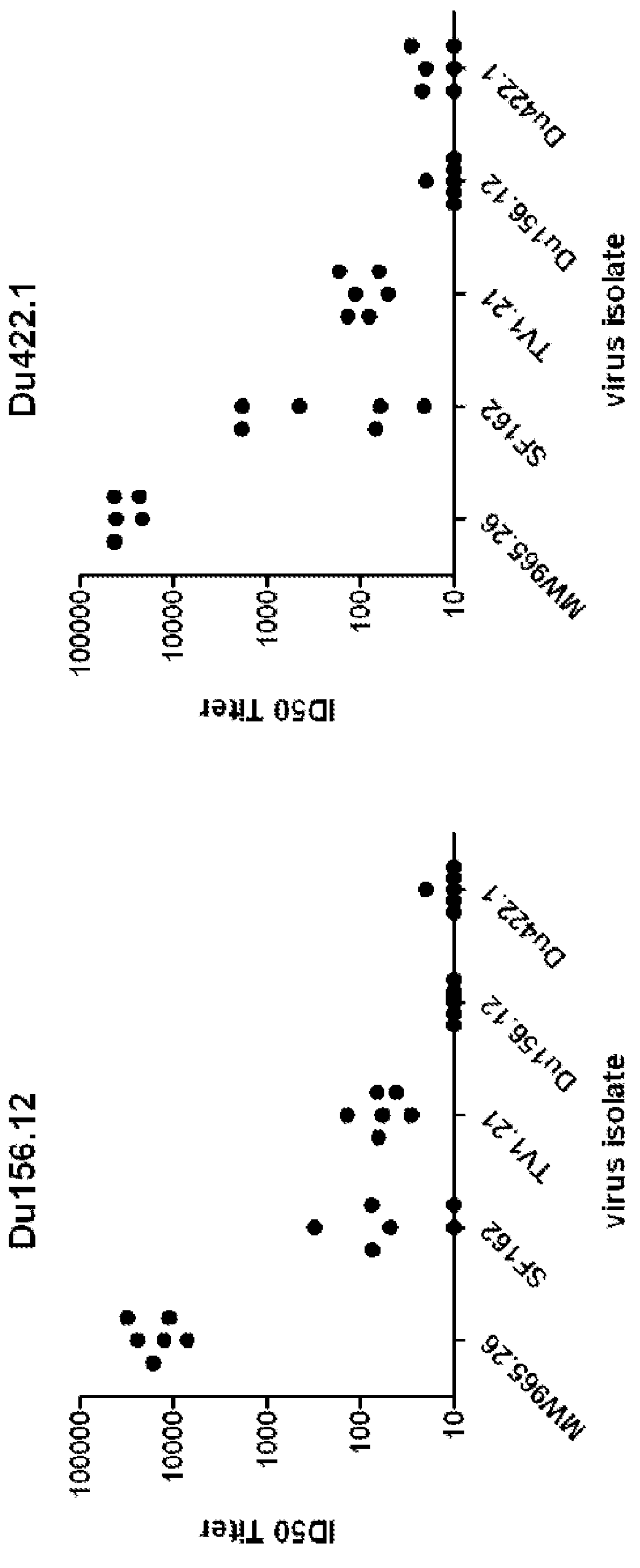
Figure 20B:
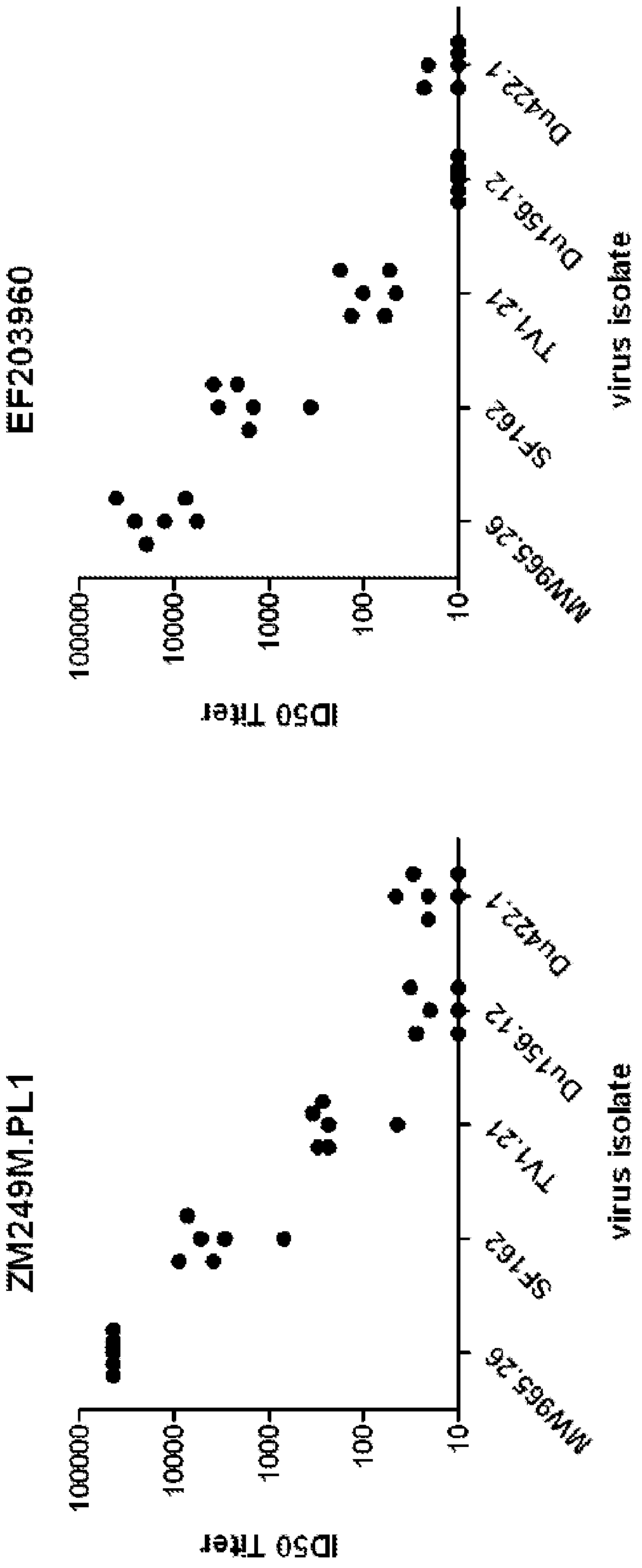
Figure 20C:
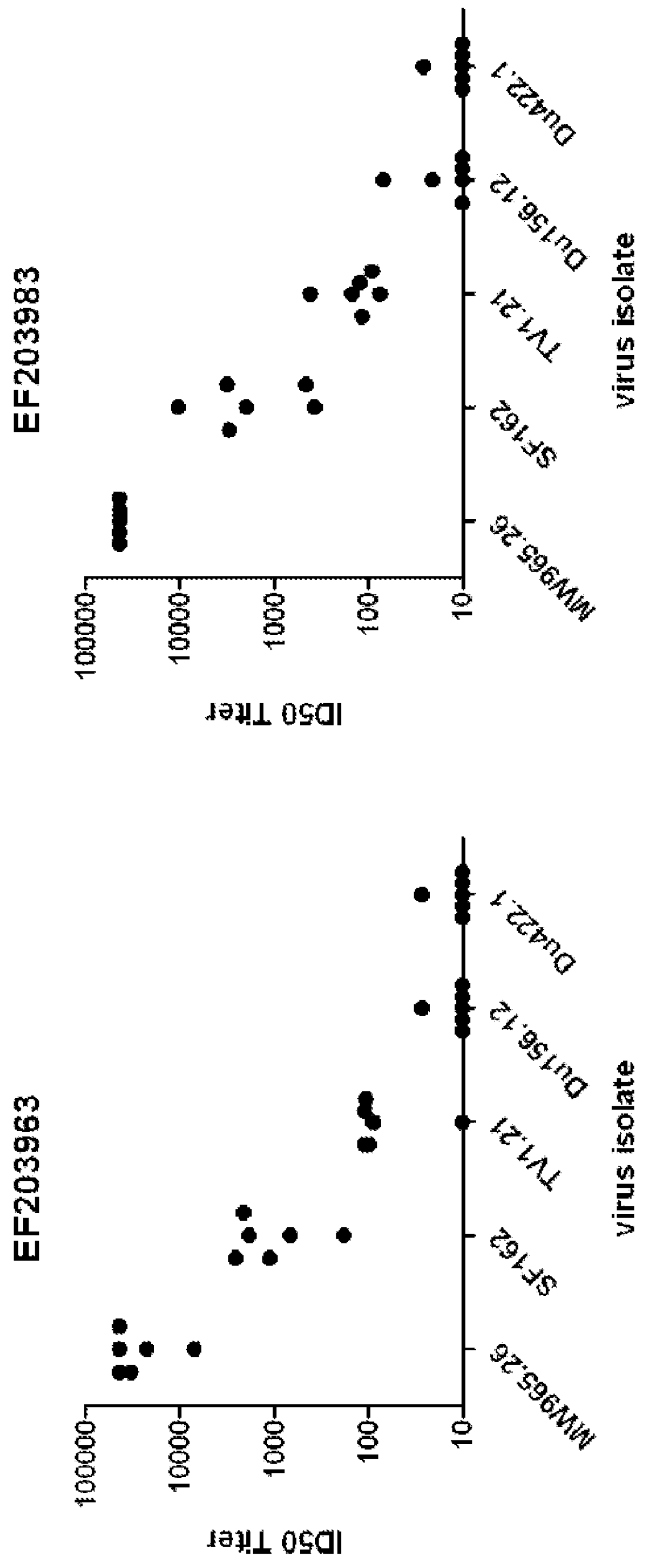
Figure 20D:
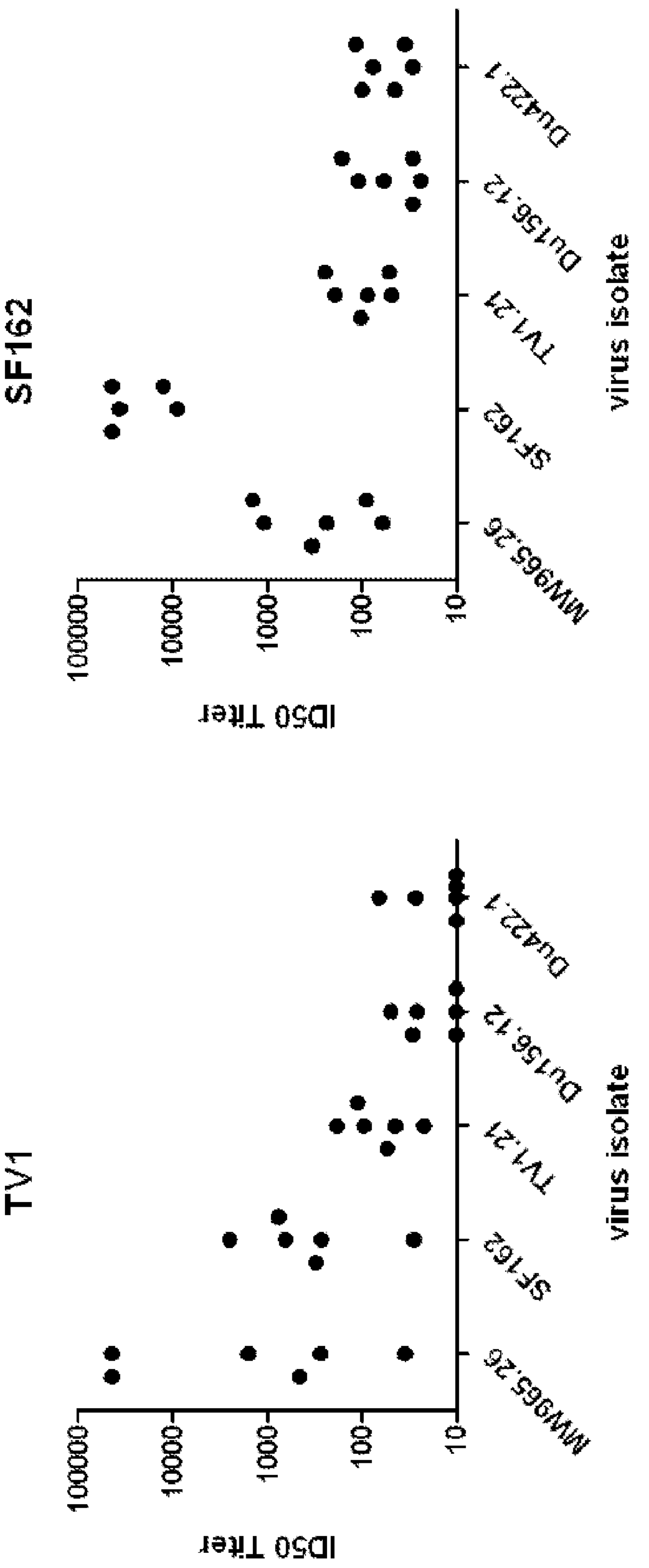
Figure 20F:
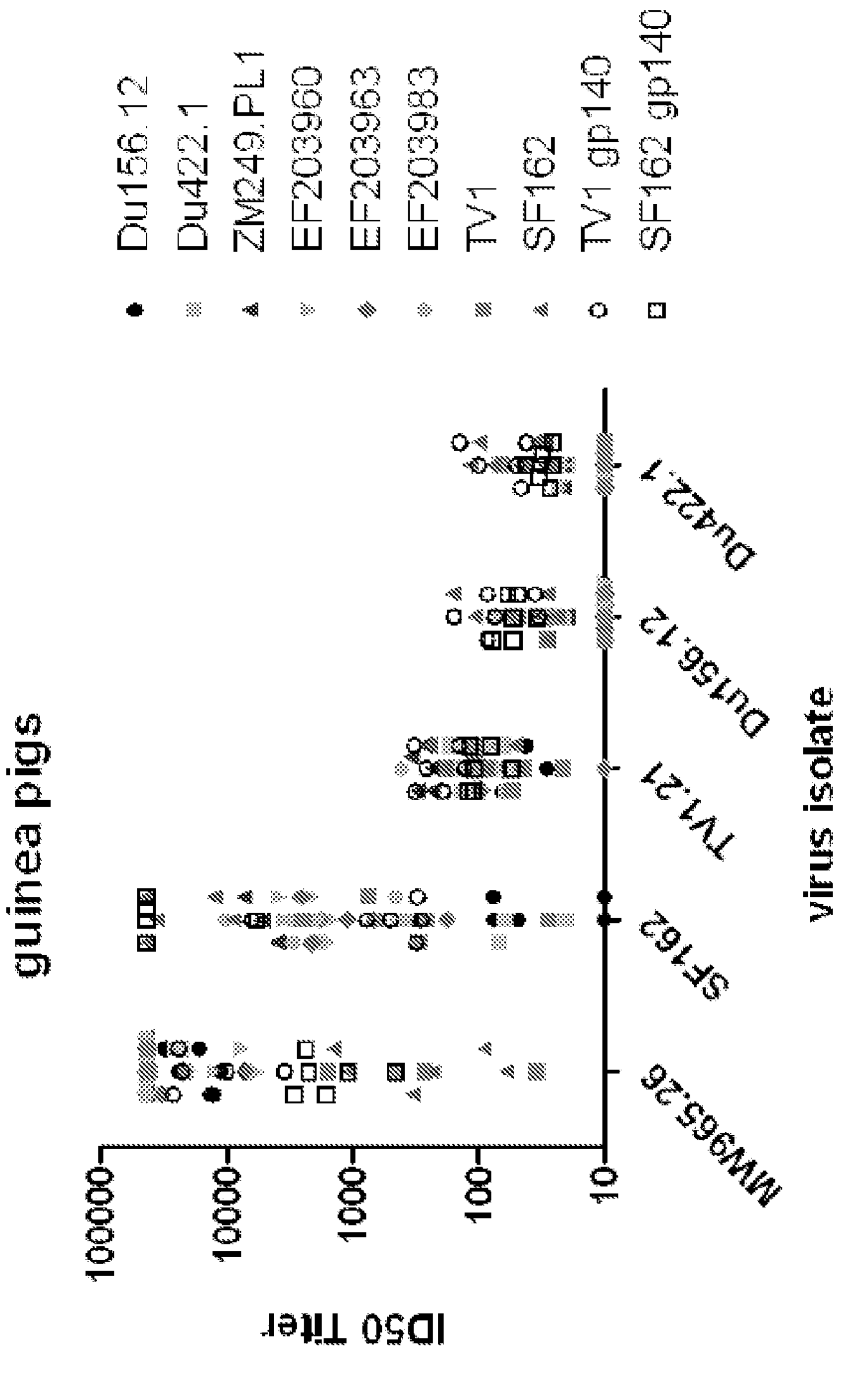
Figure 24A:
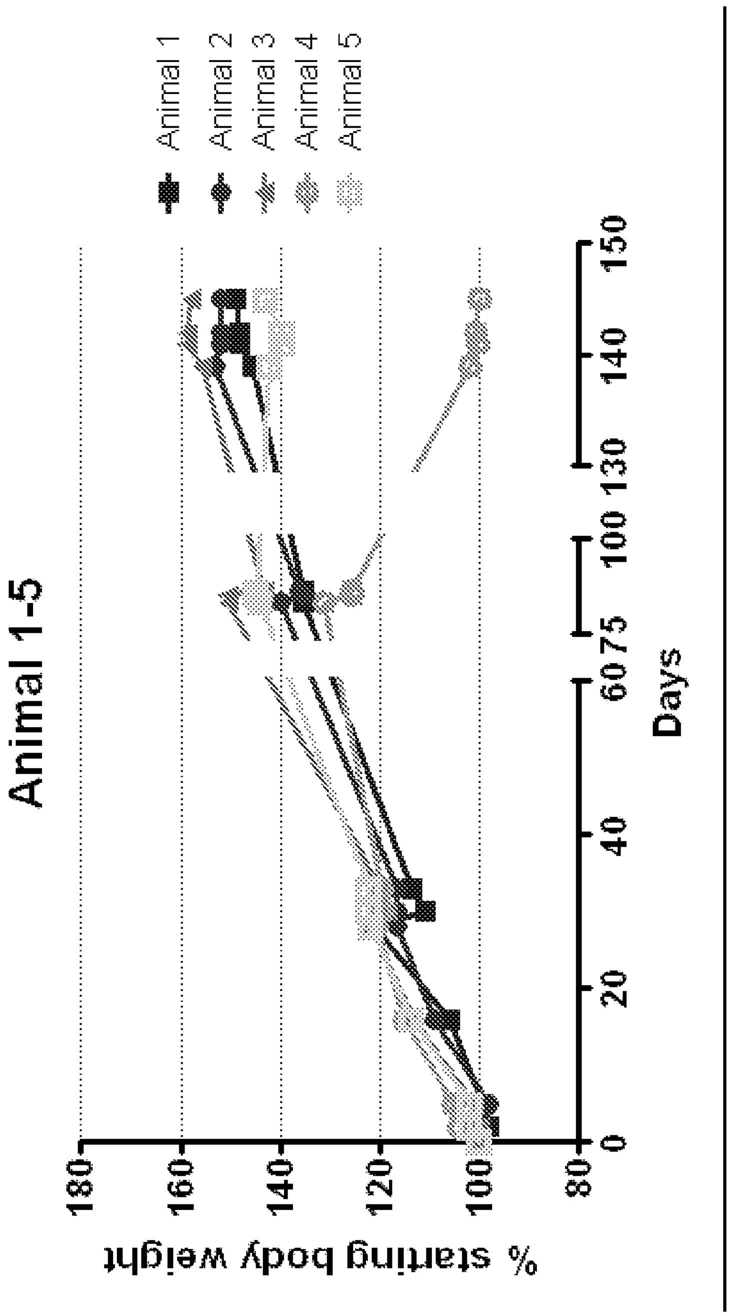
FIGS. 24A-K show the body weights (y axis) of fifty five rabbits immunized with gp120 Env polypeptide, adjuvanted with MF59™+CARBOPOL 971™, at various time points after the immunization began (y axis).
Figure 24B:
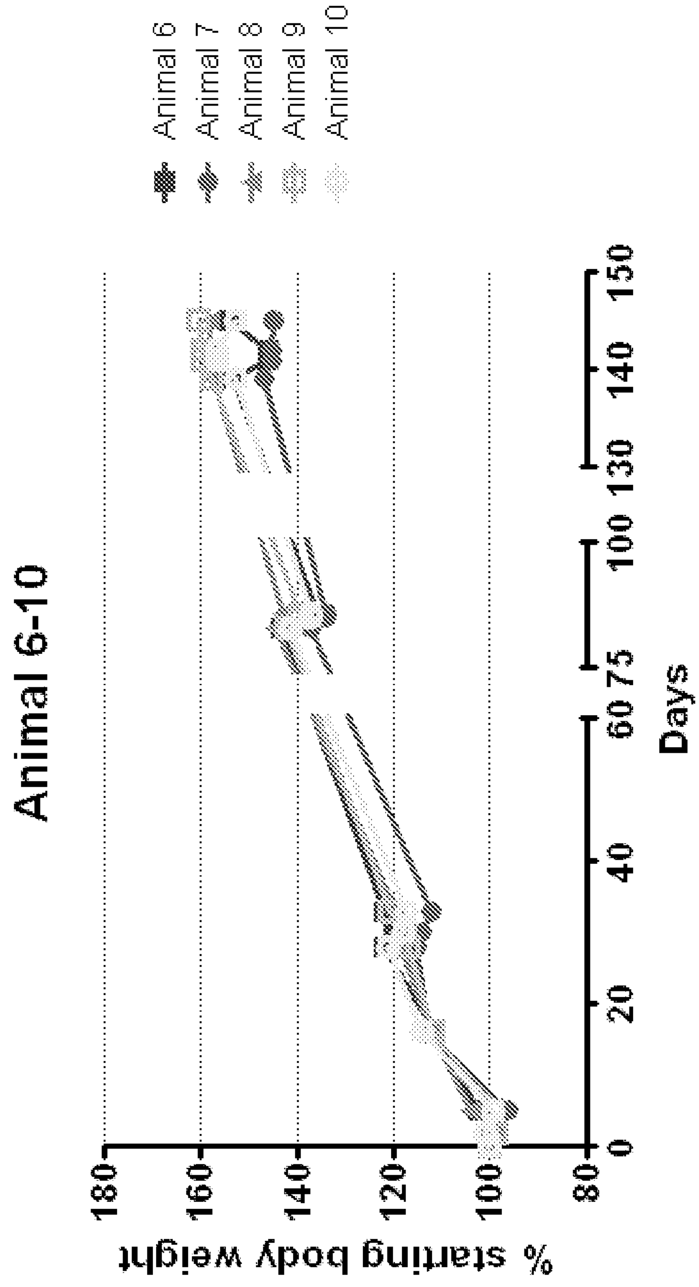
Figure 24C:
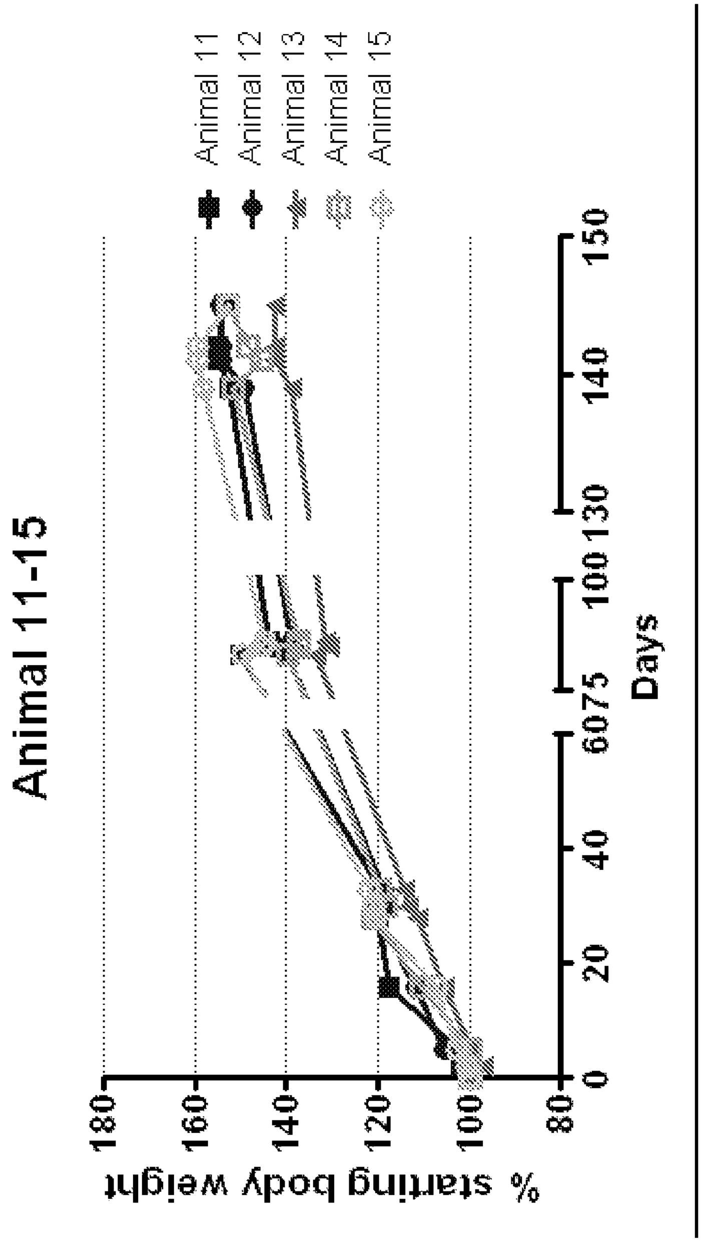
Figure 24D:
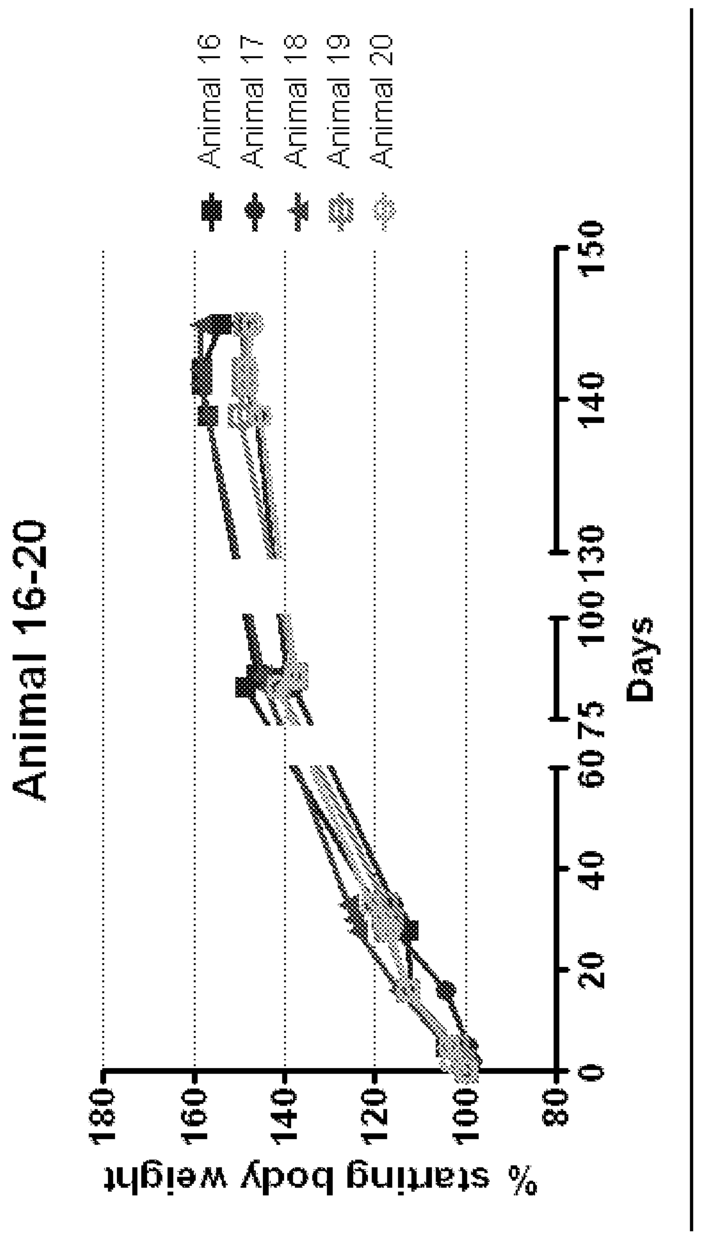
Figure 24E:
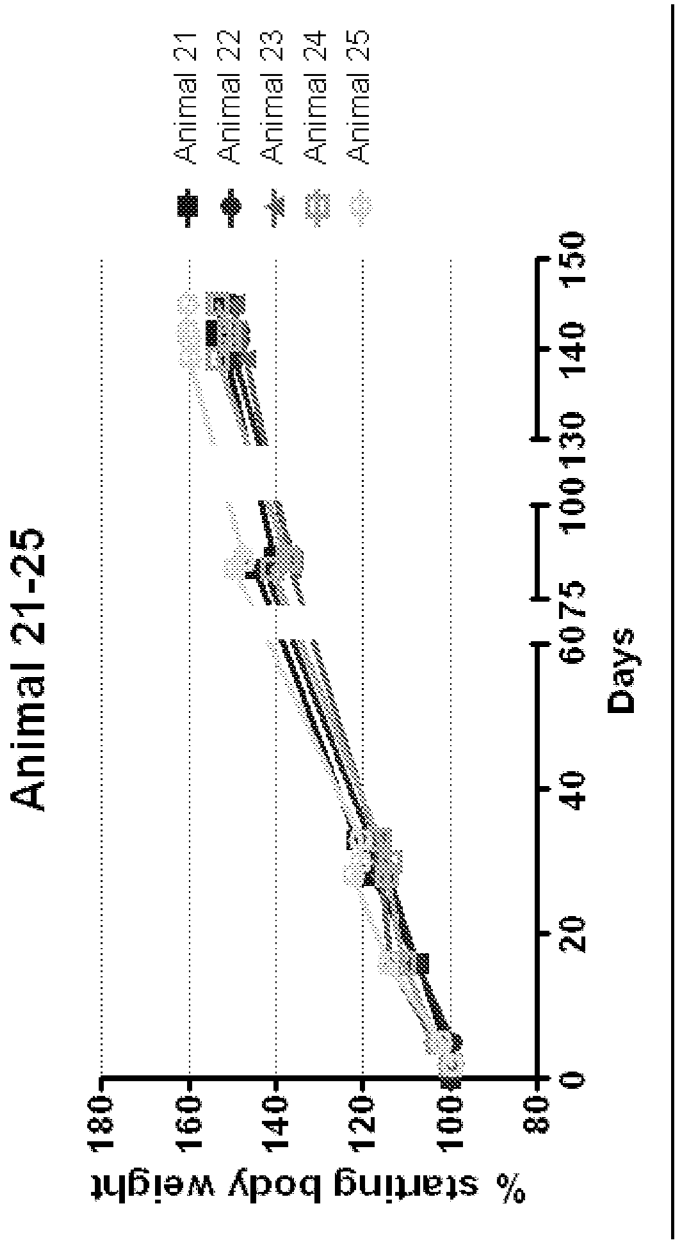
Figure 24F:
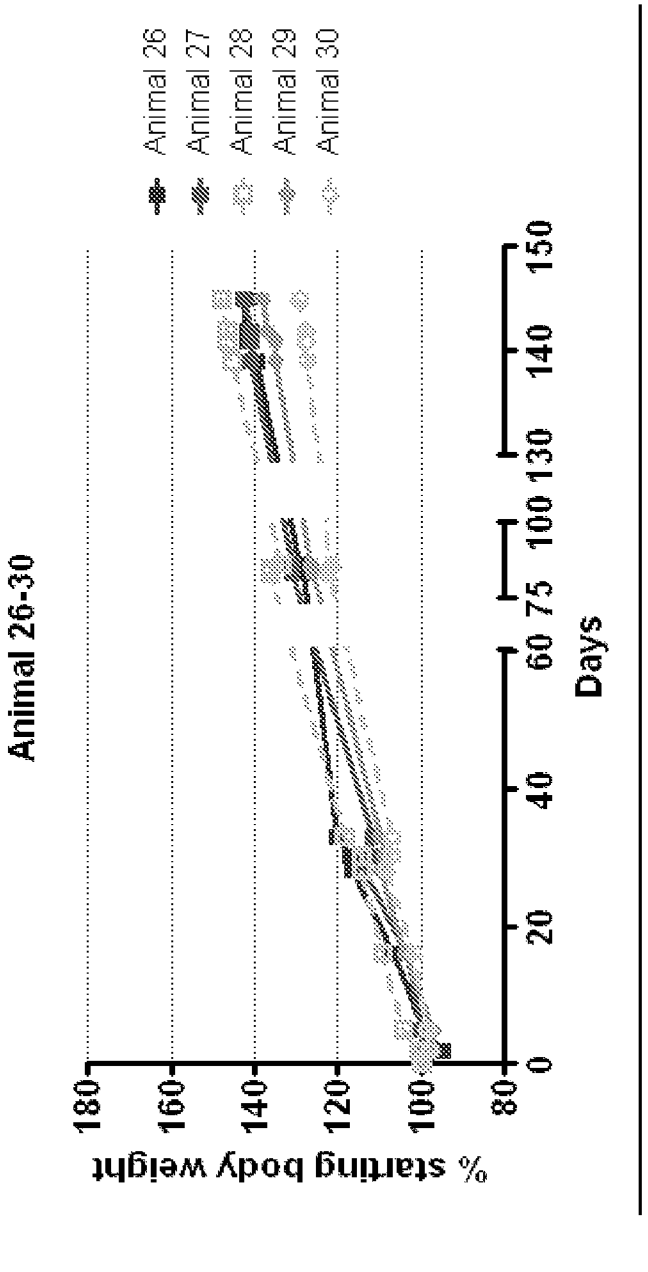
Figure 24G:
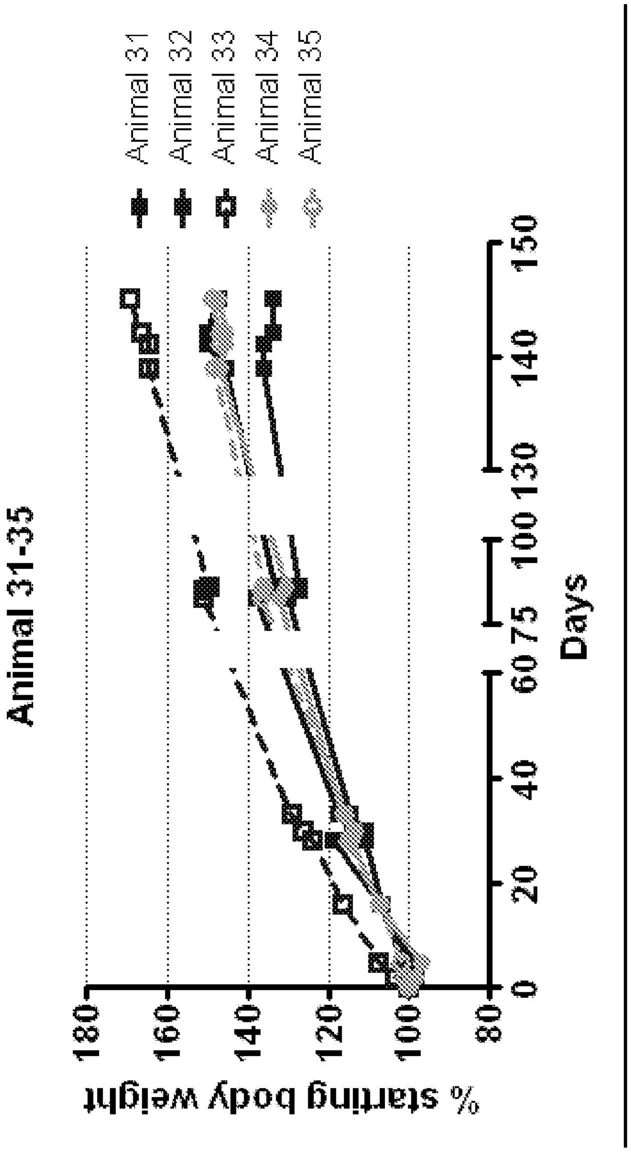
Figure 24H:
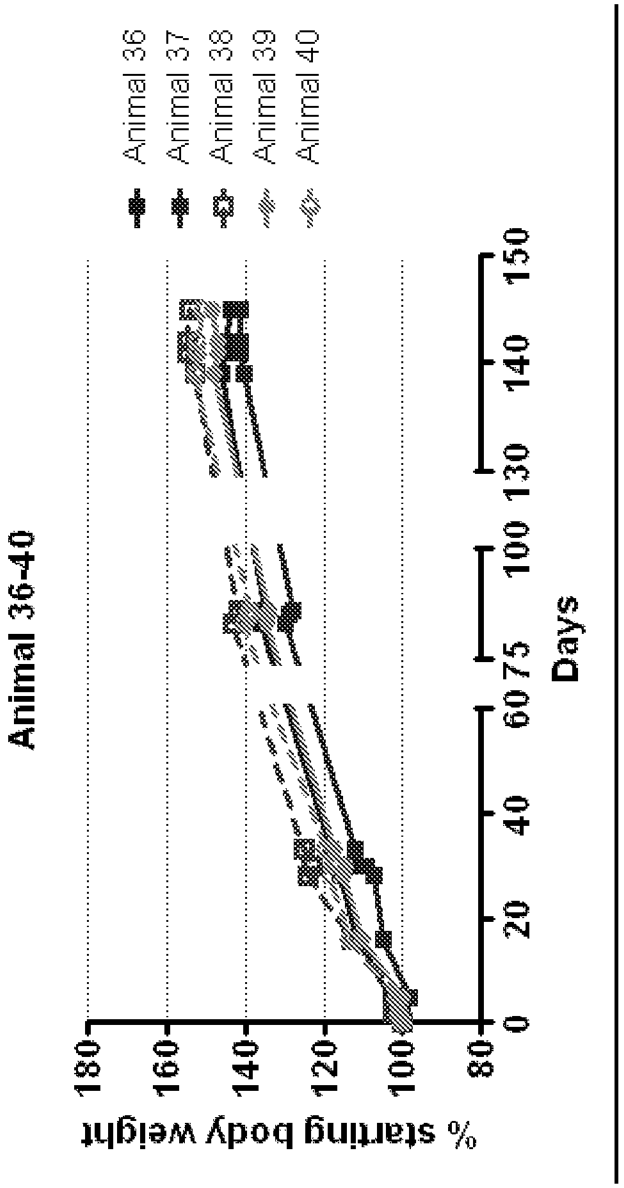
Figure 24I:
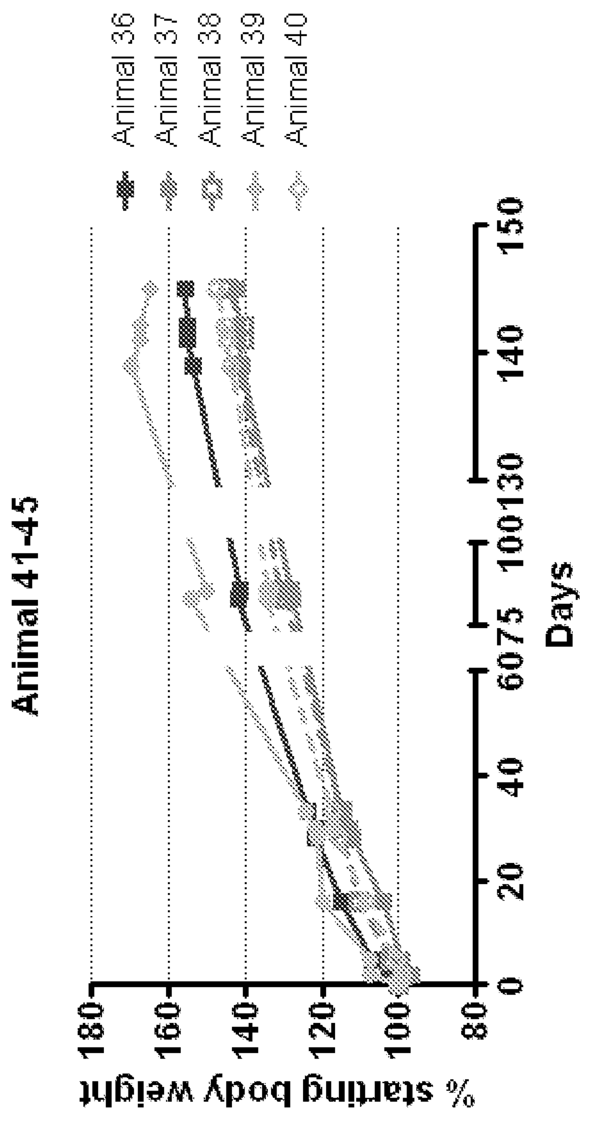
Figure 24J:
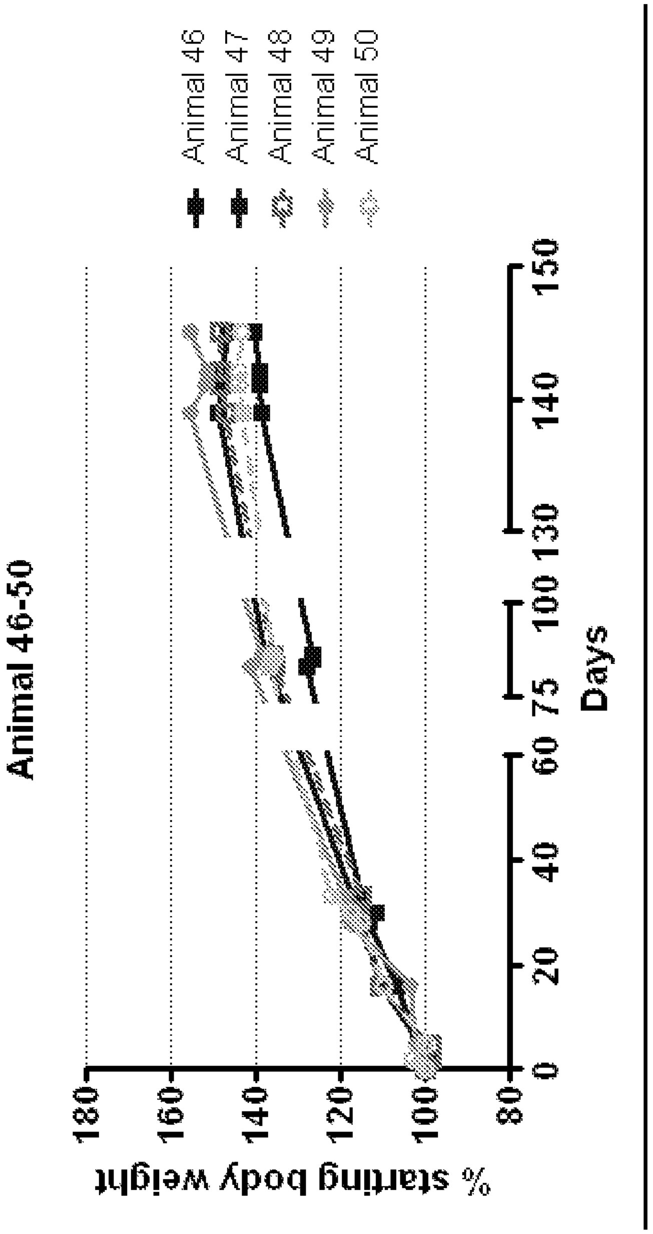
Figure 24K:
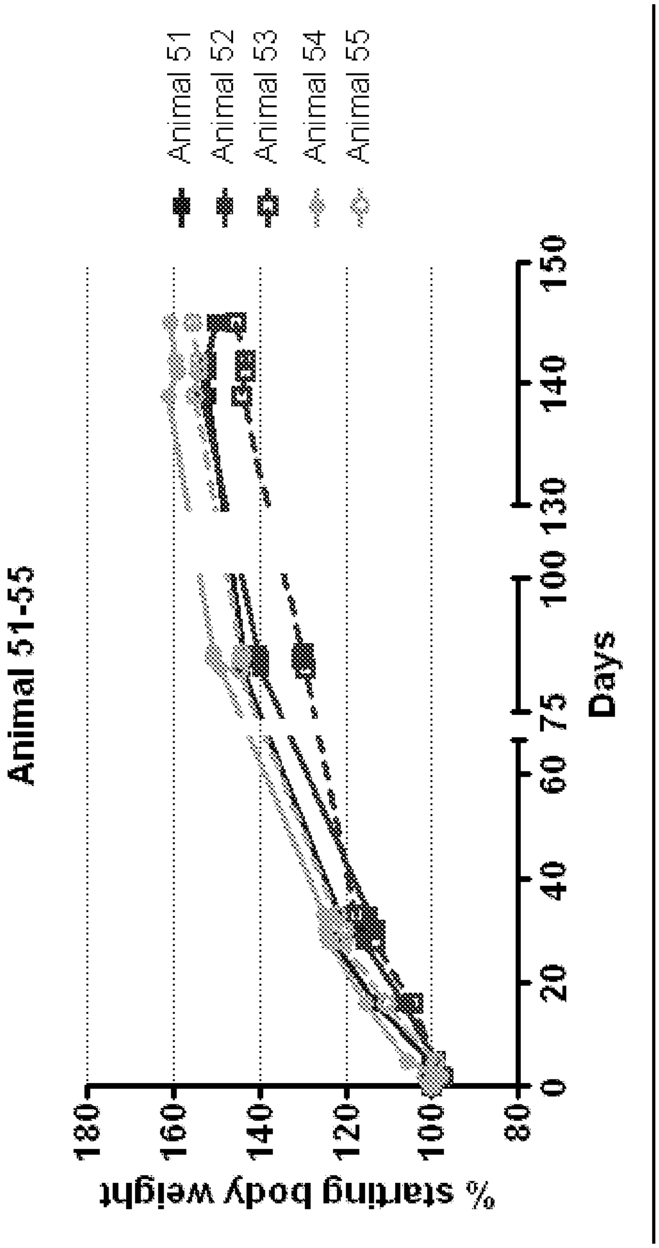

The avidity of the antibodies was determined as described above. (FIG. 16—Group 8 (multivalent): ZM249M.PL1+CAP239+Du422.1+TV1 gp140; Group 9 (sequential): CAP239 gp140/Du422.1 gp140/ZM249M.PL1 gp140/TV1 gp140).

Example 8

Evaluate Effect of DNA Prime-Protein Boost Versus Protein Only Immunizations with CARBOPOL 971P NF™:Env Complexes Adjuvanted with MF59™

To confirm whether the improvement in the immunogenicity required a DNA prime, data from the previously shown immunization experiments using 2 DNA-prime followed by 3 protein-boost (see Table 3) or 4 protein boosts (see Table 4) immunizations of the CARBOPOL 971P NF™:Env complexes adjuvanted with MF59™ were further analyzed. A number of different gp140 Env polypeptides generated from subtype C isolates were tested. All gp140 isolates tested showed an improvement in the immunogenicity (See Table 5—(2wp2—2-weeks after second protein boost and after two DNA primes; 2wp4—2-weeks after fourth protein boost but no DNA prime). ≥60% of the animals exhibited >90% neutralization potency against a Subtype C pseudovirus, MW965.1. The priming via DNA or other vector could be beneficial for eliciting key immune response such as T-cell response (not measured here). However, from just the antibody-response, the effect of improved neutralization is not dependent upon DNA priming. Further, the improved immunogenicity is not limited to the SF162 isolate or even Subtype B isolates.

Significantly, when comparing average viral inhibition of pseudoviruses, between MF59™ without CARBOPOL™) and MF59™ with CARBOPOL 971P NF™, we observed that in each case MF59™ with CARBOPOL 971P NF™ generated better functional response than MF59™ only group.

TABLE 5

Neutralization Potency of Env polypeptides adjuvanted with MF59 (TM) against Subtype C isolates

| | No CARBOPOL(TM) | | CARBOPOL 971P NF(TM) | |
|---|---|---|---|---|
| Isolates (Gp140) | Sera >90% inhibition. (2wp4) | Average inhibition (%) | Sera >90% inhibition (2wp2) | Average inhibition (%) |
| Du156.12 | 1/5 | 72 | 4/5 | 92 |
| Du422.1 | 1/5 | 76 | 4/5 | 88 |
| ZM249.PL1 | 1/5 | 81 | 3/5 | 90 |
| CAP239 | 1/5 | 79 | 3/5 | 90 |
| TV1 | 1/5 | 85 | 3/5 | 89 |
| | | | 2/5 (ΔV2) | 88 |
| ZM249.PL1 + CAP239 + Du422.1 | 1/5 | 81 | 4/5 | 92 |

Example 9

Immunogenicity of CARBOPOL 971P NF™:Env gp120 Polypeptide Complexes Adjuvanted with MF59™ in Rabbits As opposed to other studies described above, where predominantly gp140 Env polypeptides were used, here we use gp120 Env polypeptide to evaluate if the improved response, when using CARBOPOL 971P NF™+MF59™, was broadly applicable to all Env constructs regardless of oligomerization state, size, etc. Immunization of rabbits with HIV-1 subtype C gp120 Env polypeptide formulated with CARBOPOL 971P NF™ and MF59™ (see Table 6). For each group shown in Table 6, five New Zealand White rabbits were used in the immunogenicity study. Rabbits were immunized with 25 μg of gp120 protein formulated in Carbopol™ and MF59. For the final group, group 11, gp120 proteins from four different strains were combined, 6.25 μg each, totaling 25 μg of gp120 protein per dose. Protein only vaccinations were administered on weeks 0, 4, 12 and 24. Serum samples were collected prior to immunization (pre-bleed) and 2 weeks following 2nd (2wp2), 3rd (2wp3) and 4th (2wp4) immunization. Final serum was collected 4 weeks after final immunization (4wp4).

TABLE 6

Immunization study design of HIV-1 subtype C gp120 Env polypeptide adjuvanted with CARBOPOL 971P NF(TM) + MF59(TM) in a protein only study (IM) in Rabbits

| Group | Protein Only (weeks 0, 4, 12, 24; dose - 25 μg) |
|---|---|
| 1 | Du156.12 gp120 |
| 2 | Du422.1 gp120 |
| 3 | ZM249M.PL1 gp120 |
| 4 | CAP45 gp120 |
| 5 | CAP84 gp120 |
| 6 | CAP239 gp120 |
| 7 | TV1 gp120 |
| 8 | SF162 gp120 |
| 9 | TV1 gp140 |
| 10 | SF162 gp140 |
| 11# | 1. CAP239; 2. Du422.1; 3. ZM249; 4. TV1 (all gp120) |

5 rabbits/group; IM immunizations

Protein: 25 μg with MF59(TM) and CARBOPOL 971P NF(TM)/dose at weeks 0, 4, 12 and 24

#Sequential immunization: 25 μg single Env/immunization

Immunization in Rabbits with Subtype C CARBOPOL 971P NF™:Env gp120 complexes adjuvanted with MF59™. Neutralization breadth (ID50 titers) determined with sera collected at 2wp3 (FIGS. 17A-F) in a single-cycle TMZ-b1 pseudovirus assay, as described above.

Immunization in Rabbits with Subtype C CARBOPOL 971P NF™:Env gp120 complexes adjuvanted with MF59™. Neutralization (ID50 titers) was determined with sera collected at 2wp3 against Tier 1a and Tier 2 HIV-1 subtype C pseudovirus panels (FIGS. 18A-B) in a single-cycle TMZ-b1 pseudovirus assay, as described above.

As described above, mAb competition ELISA was conducted against immobilized TV1 gp140 Env polypeptide with pooled sera (1:100 dilution) collected 2 weeks post $4^{th}$ immunization with subtype C gp120 (week 22) (FIG. 19), to dissect antibody specificity against Env.

Example 10

Immunogenicity of CARBOPOL 971P NF™:Env gp120 Polypeptide Complexes Adjuvanted with MF59™ in Protein Only (IM) Study in Guinea Pigs Immunization of Guinea pigs with HIV-1 subtype C gp120 Env polypeptide formulated with CARBOPOL 971P NF™+ MF59™ (see Table 7): Guinea-pigs were immunized with 25 μg of gp120 protein formulated in Carbopol™ and MF59™. Protein only vaccinations were administered on weeks 0, 4, 12 and 24. Serum samples were collected prior to immunization (pre-bleed) and 2 weeks following $2^{nd}$ (2wp2), $3^{rd}$ (2wp3) and $4^{th}$ (2wp4) immunization. Final sera were collected 4 weeks after final immunization (4wp4).

TABLE 7

Immunization schedule of HIV-1 subtype C gp120 Env formulated with CARBOPOL 971P NF(TM) in Guinea pigs

| Group | Protein Only (weeks 0, 4, 12, 24; dose - 25 μg) |
|---|---|
| 1 | Du156.12 gp120 |
| 2 | Du422.1 gp120 |
| 3 | ZM249M.PL1 gp120 |
| 4 | CAP45 gp120 |
| 5 | CAP84 gp120 |
| 6 | CAP239 gp120 |
| 7 | TV1 gp120 |
| 8 | SF162 gp120 |
| 9 | TV1 gp140 |
| 10 | SF162 gp140 |

5 Guinea pigs/group; IM immunizations

Protein: 25 μg with MF59(TM) and CARBOPOL 971P NF(TM)/dose at weeks 0, 4, 12 and 24

Neutralization breadth (ID50 titers) was determined with sera collected at 2wp3 (FIGS. 20A-F) in a single-cycle TMZ-b1 pseudovirus assay, as described above. Neutralization (ID50 titers) was determined with sera collected at 2wp3 against Tier 1a and Tier 2 HIV-1 subtype C virus panels (FIG. 21) in a single-cycle TMZ-b1 pseudovirus assay, as described above.

As described above, mAb competition ELISA was conducted against immobilized TV1 gp140 Env polypeptide with pooled sera (1:500 dilution) collected 2 weeks post $3^{rd}$ (FIG. 22; week 14) or 2 weeks post $4^{th}$ (FIG. 23; week 26) immunization with subtype C gp120), to assess antibody specificity against Env.

Example 11

Evaluate Adverse Reactions with CARBOPOL 971™:Env Complexes Adjuvanted with MF59™ after Injection in Rabbits Rabbits were observed for overall reactogenicity and for any obvious health problems against CARBOPOL 971™ after immunization (See Table 8). MF59™ has been used in multiple species, including humans, and found to be safe. Therefore, the goal was to determine if CARBOPOL 971P NF™ in combination with MF59™ causes any adverse reactivity. Since MF59™ does not cause any such reactivity, any observed reactogenicity would likely be due to CARBOPOL 971P NF™. However, no immediate local reactogenicity post injection was observed at the injection site. Development of small edema and erythema was detected within 1-2 hours following each injection, which disappeared after 24 hours. As shown in FIGS. 24A-K, no significant loss of body weight occurred immediately after the first vaccination and all animals from the three groups shown in FIGS. 24A-K continued to gain weight for more than 140 days during the course of the study. Rabbits were monitored for body-weight one day before immunization, 24, 48 and 72 hours post-vaccination (see FIG. 24). Local reactivity and obvious health problems were monitored at 24, 48 and 72 hours post-vaccination. All observations were recorded in a log-notebook. Overall, no obvious health problems (NOHP) were observed in rabbits vaccinated with CARBOPOL 971™:Env polypeptide adjuvanted with MF59™; also no significant loss of body-weight post-immunization was observed. This indicates that administration of CARBOPOL 971™ was safe in rabbits under the present settings.

TABLE 8

| Rabbit study: Animals observed for loss of body-weight and any obvious health problems during or after immunization of gp120 with Carbopol and MF59 | | |
|---|---|---|
| Group | Env Protein | Animals |
| 1 | Du156.12 gp120 | 1-5 |
| 2 | Du422.1 gp120 | 6-10 |
| 3 | ZM249M.PL1 gp120 | 11-15 |
| 4 | CAP45 gp120 | 16-20 |
| 5 | CAP84 gp120 | 21-25 |
| 6 | CAP239 gp120 | 26-30 |
| 7 | TV1 gp120 | 31-35 |
| 8 | SF162 gp120 | 36-40 |
| 9 | TV1 gp140 | 41-45 |
| 10 | SF162 gp140 | 46-50 |
| 11# | 1. CAP239; 2. Du422.1; 3. ZM249; 4. TV1 (all gp120) | 51-55 |

What we claim is:

1. An immunogenic composition comprising a human immunodeficiency virus envelope (Env) polypeptide complexed to a polyanionic carbomer polymer.

2. The method of claim 1, wherein the polyanionic carbomer polymer is adsorbed to the human immunodeficiency virus envelope (Env) polypeptide.

3. An immunogenic composition comprising an Env polypeptide complexed to a polyanionic carbomer polymer, wherein the concentration of the polyanionic carbomer polymer is between about 0.01% (w/v) and about 0.5% (w/v).

4. The immunogenic composition of claim 1, wherein the concentration of the polyanionic carbomer polymer is between about 0.01% (w/v) and about 0.5% (w/v).

5. The immunogenic composition of claim 1, wherein the polyanionic polymer was cross-linked with allyl penta erythritol and polymerized in ethyl acetate.

6. The immunogenic composition of claim 1, wherein the Env polypeptide comprises a polypeptide selected from the group consisting of a glycoprotein 160 (gp160) Env polypeptide, a polypeptide derived from a gp160 Env polypeptide, a glycoprotein 140 (gp140) Env polypeptide, a polypeptide derived from a gp140 Env polypeptide, a glycoprotein 120 (gp120) Env polypeptide, and a polypeptide derived from a gp120 Env polypeptide.

7. The immunogenic composition of claim 1, wherein the Env polypeptide is an HIV Env polypeptide and the composition further comprises a second Env polypeptide selected from a different HIV subtype as the Env polypeptide wherein the Env polypeptide and the second Env polypeptide are derived from an HIV subtype B strain and an HIV subtype C strain or vice-versa.

8. The immunogenic composition of claim 1 further comprising an adjuvant which is an oil-in-water emulsion.

9. A method of generating an immunogenic composition comprising an Env polypeptide complexed to a polyanionic carbomer polymer, the method comprising:

(a) contacting the polyanionic carbomer polymer with the Env polypeptide under conditions where the pH is below the pI of the Env polypeptide in a solution;

(b) incubating the polyanionic carbomer polymer with the Env polypeptide together to allow the Env polypeptide to form a complex with the polyanionic carbomer polymer.

10. The method of claim 9, wherein the pH is between 3 and 5.

11. The method of claim 9, wherein the pH is between 3 and 4.

12. The method of claim 9, wherein the concentration of the polyanionic carbomer polymer after contacting step (a) is between about 0.01% (w/v) and about 0.5% (w/v).

13. The method of claim 9, wherein the polyanionic carbomer polymer was cross-linked with allyl penta erythritol and polymerized in ethyl.

14. The method of claim 9, wherein the Env polypeptide comprises a polypeptide selected from the group consisting of a gp160 Env polypeptide, a polypeptide derived from a gp160 Env polypeptide, a gp140 Env polypeptide, a polypeptide derived from a gp140 Env polypeptide, a gp120 Env polypeptide, and a polypeptide derived from a gp120 Env polypeptide.

15. The method of claim 9, wherein the Env polypeptide is an HIV Env polypeptide and the composition further comprises a second HIV Env polypeptide selected from a different HIV subtype as the Env polypeptide wherein the Env polypeptide and the second Env polypeptide are derived from an HIV subtype B strain and an HIV subtype C strain or vice-versa.

16. The method of claim 9, further comprising adding an adjuvant, which is an oil-in-water emulsion adjuvant, to the solution.

17. A method of generating an immune response in a subject, comprising administering to said subject an immunogenic composition comprising an Env polypeptide complexed to a polyanionic carbomer polymer, thereby generating the immune response to the Env polypeptide.

18. The method of claim 17, wherein the immunogenic composition is administered intramuscularly, intramucosally, intranasally, subcutaneously, intradermally, transdermally, orally or intravenously.

19. The method of claim 17, wherein the immunogenic composition is administered by injection.

20. The method of claim 17, wherein the concentration of the polyanionic carbomer polymer is between about 0.01% (w/v) and about 0.5% (w/v).

* * * * *